(12) United States Patent
Schriemer et al.

(10) Patent No.: US 10,857,214 B2
(45) Date of Patent: *Dec. 8, 2020

(54) COMPOSITIONS AND METHODS FOR TREATING GLUTEN INTOLERANCE AND DISORDERS ARISING THEREFROM

(71) Applicant: Codexis, Inc., Redwood City, CA (US)

(72) Inventors: David C. Schriemer, Chestermere (CA); Martial Rey, Paris (FR)

(73) Assignee: CODEXIS, INC., Redwood City, CA (US)

( * ) Notice: Subject to any disclaimer, the term of this patent is extended or adjusted under 35 U.S.C. 154(b) by 611 days.

This patent is subject to a terminal disclaimer.

(21) Appl. No.: 15/382,560

(22) Filed: Dec. 16, 2016

(65) Prior Publication Data
US 2017/0232077 A1 Aug. 17, 2017

Related U.S. Application Data

(60) Provisional application No. 62/268,445, filed on Dec. 16, 2015.

(51) Int. Cl.
| | |
|---|---|
| *A61K 38/48* | (2006.01) |
| *C12N 9/50* | (2006.01) |
| *A61P 1/14* | (2006.01) |
| *A61K 9/00* | (2006.01) |
| *A61K 45/06* | (2006.01) |

(52) U.S. Cl.
CPC .......... *A61K 38/488* (2013.01); *A61K 9/0053* (2013.01); *A61K 38/48* (2013.01); *A61K 45/06* (2013.01); *A61P 1/14* (2018.01); *C12N 9/63* (2013.01); *C12Y 304/23012* (2013.01)

(58) Field of Classification Search
CPC ..... C12N 9/50; C12N 9/63; A61P 1/00; A61P 1/14; A61K 9/0053; A61K 38/48; A61K 45/06; A61K 38/488; C12Y 304/23012; C12Y 304/23

See application file for complete search history.

(56) References Cited

U.S. PATENT DOCUMENTS

| | | | |
|---|---|---|---|
| 5,618,564 | A | 4/1997 | Kimura et al. |
| 6,190,905 | B1 | 2/2001 | Dalboege et al. |
| 7,303,871 | B2 | 12/2007 | Hausch et al. |

(Continued)

FOREIGN PATENT DOCUMENTS

| | | |
|---|---|---|
| EP | 2090662 A2 | 8/2009 |
| JP | H1149697 A | 2/1999 |

(Continued)

OTHER PUBLICATIONS

Clarindo et al. "Dermatitis herpetiformis: pathophysiology, clinical presentation, diagnosis and treatment" An Bras Dermatol. 2014; 89(6):865-77 (Year: 2014).*

(Continued)

*Primary Examiner* — Thane Underdahl
(74) *Attorney, Agent, or Firm* — Mintz, Levin, Cohn, Ferris, Glovsky and Popeo, P.C.

(57) ABSTRACT

The invention described herein relates to methods and compositions for treatment of one or more symptoms of gluten intolerance and related conditions (e.g., celiac disease and gluten sensitivity) by administration of a pharmaceutical composition comprising one or more Nepenthes enzymes.

14 Claims, 19 Drawing Sheets

Specification includes a Sequence Listing.

(56) References Cited

U.S. PATENT DOCUMENTS

| | | |
|---|---|---|
| 7,320,788 B2 | 1/2008 | Shan et al. |
| 7,628,985 B2 | 12/2009 | Shan et al. |
| 7,910,541 B2 | 3/2011 | Hausch et al. |
| 7,943,312 B2 | 5/2011 | Hausch et al. |
| 8,119,125 B2 | 2/2012 | Gass |
| 8,143,210 B2 | 3/2012 | Shan et al. |
| 8,148,105 B2 | 4/2012 | Vora et al. |
| 9,005,610 B2 | 4/2015 | Schriemer et al. |
| 9,498,520 B2 | 11/2016 | Jolly et al. |
| 9,598,684 B2 | 3/2017 | Helmerhorst et al. |
| 9,745,565 B2 | 8/2017 | Schriemer |
| 9,993,531 B2 | 6/2018 | Siegel et al. |
| 2005/0107786 A1 | 5/2005 | Canady |
| 2005/0249719 A1 | 11/2005 | Shan et al. |
| 2006/0095096 A1 | 5/2006 | DeBenedictis et al. |
| 2008/0115411 A1 | 5/2008 | Ramsey |
| 2008/0115428 A1 | 5/2008 | Schlam et al. |
| 2010/0011456 A1 | 1/2010 | Mathur et al. |
| 2010/0021752 A1 | 1/2010 | Okamura et al. |
| 2010/0042203 A1 | 2/2010 | Cottone, Jr. et al. |
| 2010/0322912 A1 | 12/2010 | Khosla et al. |
| 2011/0097266 A1 | 4/2011 | Maecke et al. |
| 2012/0156253 A1 | 6/2012 | Shan et al. |
| 2012/0225050 A1 | 9/2012 | Knight et al. |
| 2013/0045195 A1 | 2/2013 | Kumar |
| 2014/0140980 A1 | 5/2014 | Schriemer |
| 2014/0186330 A1* | 7/2014 | Schriemer ............ A61K 38/488 424/94.66 |
| 2015/0265686 A1 | 9/2015 | Schriemer |
| 2015/0290301 A1 | 10/2015 | Schriemer et al. |
| 2015/0352195 A1 | 12/2015 | Berner et al. |

FOREIGN PATENT DOCUMENTS

| | | |
|---|---|---|
| JP | 2004248654 A | 9/2004 |
| WO | WO-2014138927 A1 | 9/2014 |
| WO | WO-2015192211 A1 | 12/2015 |

OTHER PUBLICATIONS

USPTO sequence search of SEQ ID No. 1 "Result 1", 2pgs performed Jul. 12, 2019 (Year: 2019).*
Freeman, "Pearls and pitfalls in the diagnosis of adult celiac disease", Canadian Journal of Gastroenterology. Mar. 2008, vol. 22, No. 3, pp. 273-280, see especially Abstract.
Gottlieb et al., "Development of drugs for celiac disease: review of endpoints for Phase 2 and 3 trials", Gastroenterology Report, vol. 3, No. 2, pp. 91-102 (Feb. 26, 2015).
PCT International Search Report and Written Opinion for Application No. PCT/US2016/067392 dated Jun. 20, 2017. (15 pages).
Rey et al., "Addressing proteolytic efficiency in enzymatic degradation therapy for celiac disease," Scientific Reports, vol. 6, (Aug. 2, 2016) p. 30980 (entire document) (13 pages).
Adlassnig W., et al., "Traps of carnivorous pitcher plants as a habitat: composition of the fluid, biodiversity and mutualistic activities," 2011. Annals of Botany. 107: 181-194.
Amagase, et al., "Acid Protease in Nepenthes," The Journal of Biochemistry, (1969), 66(4):431-439.
Athauda, et al., "Enzymic and structural characterization of nepenthesin, a unique member of a novel subfamily of aspartic proteinases," Biochemical Journal (2004) 381(1):295-306.
Bennett, et al., "Discovery and Characterization of the Laulimalide-Microtubule Binding Mode by Mass Shift Perturbation Mapping," Chemistry & Biology, (2010), 17:725-734.
Bethune, et al., "Oral enzyme therapy for celiac sprue," Methods Enzymol., (2012), 502:241-271.
Blonder, et al., "Proteomic investigation of natural killer cell microsomes using gas-phase fractionation by mass spectrometry," Biochimica et Biophysica Acta, (2004), 1698:87-95.
Chen, Jiongjiong, et al., "Aspartic proteases gene family in rice: gene structure and expression, predicted protein features and phylogenetic relation." Gene 442.1 (2009): 108-118.
Chung, et al., "Aspartic Proteinases are Expressed in Pitchers of the Carnivorous Plant Nepenthes Alata Blanco," Planta, Springer Verlag, DE, vol. 214, No. 5, (Mar. 1, 2002), p. 661-667.
Clabots, et al., "Acquisition of Clostridium difficile by Hospitalized Patients: Evidence for Colonized New Admissions as a Source of Infection," J. Infectious Diseases, (1992), 166:561-567.
Dunker, et al., "Intrinsically disordered protein," J. Molecular Graphics and Modelling, (2001), 19:26-59.
GenBank AB114914.1. GenBank 2004. p. 1-2 (2004).
GenBank AB114915.1. GenBank 2004. p. 1-2 (2004).
GenBank AFV26025.1. GenBank 2012. p. 1-2 (2012).
Gleba, Y., et al., "Viral Vectors for the Expression of Proteins in Plants," Current Opinion in Biotechnology, 18:134-141. (2007).
Good NE., et al., "Hydrogen Ion Buffers for Biological Research," 1966. Biochemistry. vol. 5, No. 2. p. 467-477.
Hammel, et al., "XLF Regulates Filament Architecture of the XRCC4.Ligase IV Complex," Structure, (2010), 18:1431-1442.
Hamuro, et al., "Specificity of immobilized porcine pepsin in H/D exchange compatible conditions," Rapid Commun. Mass Spectrom., (2008), 22:1041-1046.
Hatano, et al., "Proteome analysis of pitcher fluid of the carnivorous plant *Nepenthes alata*," Journal of Proteome Research (2008), 7(2):809-816.
Hatano, et al., "Proteomic analysis of secreted protein induced by a component of prey in pitcher fluid of the carnivorous plan Nepenthes alata," JPROT, (2012), 1-9.
Jentsch, J., "Enzymes from carnivorius plants (*Nepenthes*). Isolation of the protease nepenthacin," FEBS Letters, (1972), 21(3):273-276.
Junop, et al., "Crystal structure of the Xrcc4 DNA repair protein and implications for end joining," The EMBO Journal, (2000), 19(22):5962-5970.
Kadek, et al., "Expression and characterization of plant aspartic protease nepenthesin-1 from Nepenthes gracilis," Protein Expression and Purification, vol. 95, (Dec. 21, 2013), p. 121-128.
Kubota, et al., "Stability Profiles of Nepenthesin in Urea and Guanidine Hydrochloride: Comparison with Porcine Pepsin A," Biosci. Biotechnol. Biochem., (2010), 74(11):2323-2326.
Lahdeaho, et al., "Recent advances in the development of new treatment for celiac disease," Expert Opin. Biol. Ther. (Early Online) 1-12, 2012.
Mazorra-Manzano, et al., "Structure-function characterization of the recombinant aspartic proteinase A1 from *Arabidopsis thaliana*," Photchem., (2010), 71(5-6):515-523.
Mitea, et al., "Efficient degradation of gluten by a prolyl endoprotease in a gastrointestinal model: implications for coeliac disease," Gut, (2008), 57:25-32.
Rey, et al., "Nepenthesin from Monkey Cups for Hydrogen/Deuterium Exchange Mass Spectrometry," Molecular & Cellular Proteomics, vol. 12, No. 2, (Nov. 29, 2012), p. 464-472.
Schendel, PF., "Expression of proteins in *Escherichia coli*," Current Protocols in Molecular Biology, 16.1.1-16.1.3, (1998).
Shan, et al., "Structural basis for gluten intolerance in celiac sprue", Science, (2002), 297:2275-2279.
Slysz, et al., "Hydra: software for tailored processing of H/D exchange daa from MS or tandem MS analyses," BMC Bioinformatics, (2009), 10:162, 1-14.
Stepniak, et al., "Highly efficient gluten degradation with a newly identiifed prolyl endoprotease: implications for celiac disease," AJP Gastrointest Liver Physiol, (2006), 291:G621-G629.
Takahashi, et al., "Nepenthesin, a unique member of a novel subfamily of aspartic proteinases: Enzy matic and structural characteristics," Current Protein & Peptide Science (2005) 6(6):513-525.
Takashai, Kenji, "Nepenthesin," Handbook of Proteolytic Enzymes, vols. 1 and 2, 3rd edition (Nov. 9, 2012), p. 125-128.
Tang, et al., "Preliminary study on the activities of protease in digestive juice of pitcher plant", Genomics and Applied Biology, 2010, 29(2): 293-297. Abstract Only.
Tökés, Zoltán A., et al., "Digestive enzymes secreted by the carnivorous plant *Nepenthes macferlanei* L." Planta 119.1 (1974): 39-46.
Vines, "On the Digestive Ferment of Nepenthes," Journal of Anatomy and Physiology, (1876) 11(Pt 1):124-127.

(56) References Cited

OTHER PUBLICATIONS

Warwood, et al., "Guanidination chemistry for qualitative and quantitative proteomics," Rapid Commun. Mass Spectrom., (2006), 20:3245-3256.
Woychik, J. H., et al., "Wheat gluten proteins, amino acid composition of proteins in wheat gluten." Journal of agricultural and food chemistry 9.4 (1961): 307-310.
Freeman, Hugh J. "Pearls and pitfalls in the diagnosis of adult celiac disease." *Canadian Journal of Gastroenterology and Hepatology* 22.3 (2008): 273-280.
Gottlieb, Klaus, et al. "Development of drugs for celiac disease: review of endpoints for Phase 2 and 3 trials." *Gastroenterology report* 3.2 (2015): 91-102.
Schrader, et al., Neprosin, a selective prolyl endoprotease for bottom-up proteomics and histone mapping, Molecular & Cellular Proteomics, Jun. 2017, pp. 1162-1171.

\* cited by examiner

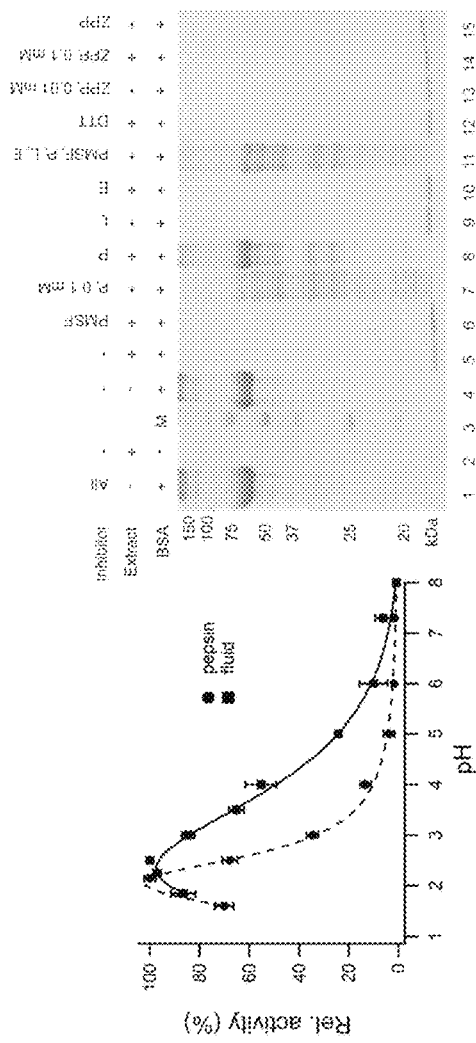
FIGURE 2A
FIGURE 2B
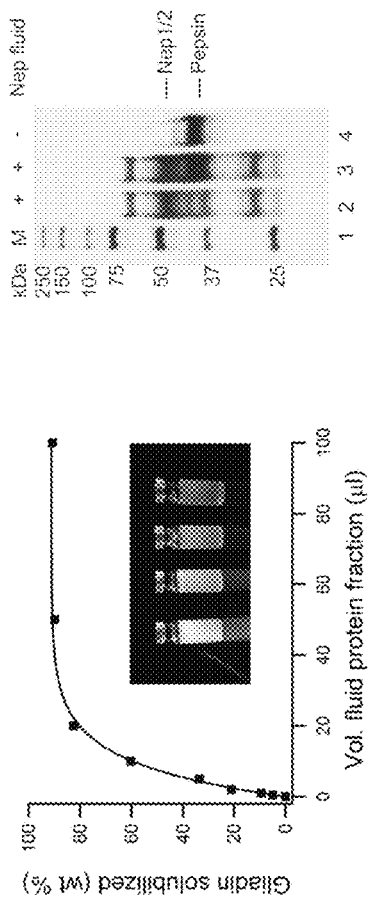
FIGURE 2C
FIGURE 2D

| Domain organization | # Sequences | SP? No | SP? Yes |
|---|---|---|---|
| I  [DUF4183][DUF2382] | 731 (58%), Npr1 | 191 (15%)* | 540 (43%) |
| II [DUF2382] | 429 (34%)* | 305 (24%) | 124 (10%) |
| III Others | 100 (8%)* | 52 (4%) | 48 (4%) |

*These groups contain considerable numbers of sequences that were incomplete or fragmented.

FIGURE 6

| Protease family | Name | Species | # amino acids | Identity (%)[a] | Substrate specificity | Domain organization[b] |
|---|---|---|---|---|---|---|
| DUF239 | Neprosin (Npr1) | Nepenthes ventrata | 380 | 100 | Pro-X | |
| | DUF4409-DUF239 | Brassica napus | 402 | 47 | | |
| S9A | Prolyl oligopeptidase (POP) | Pyrococcus furiosus | 616 | <20 | C-terminal Pro-X oligopeptides | |
| | | Myxococcus xanthus | 692 | <20 | | |
| | | Flavobacterium meningosepticum | 705 | <20 | | |
| | | Sphingomonas capsulata | 723 | <20 | | |
| S28 | Prolyl endoprotease (PEP) | Aspergillus niger | 526 | <20 | Pro-X | |
| S9B | Dipeptidyl-peptidase IV (DPP-IV) | Aspergillus oryzae | 771 | <20 | N-terminal Pro-X dipeptide | |
| M24B | Aminopeptidase P (APP) | Sus scrofa | 673 | <20 | N-terminal X-Pro dipeptide | |

[a] identity referenced to the sequence of neprosin
[b] domain organization from Pfam, with active site residue highlighted
[c] association of this entry to Pro-X functionality is speculative

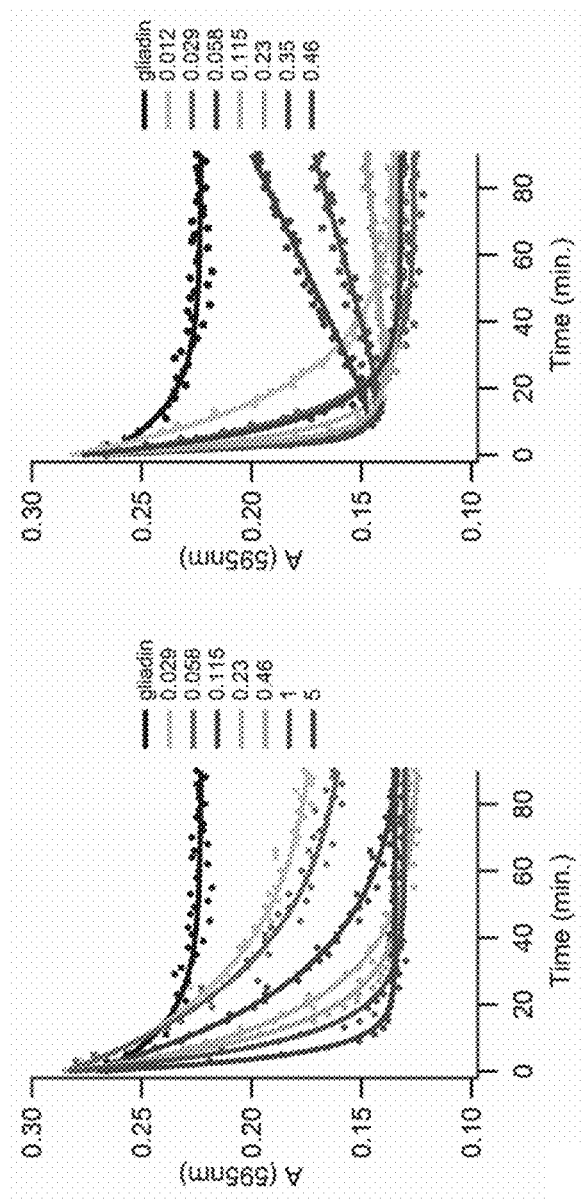

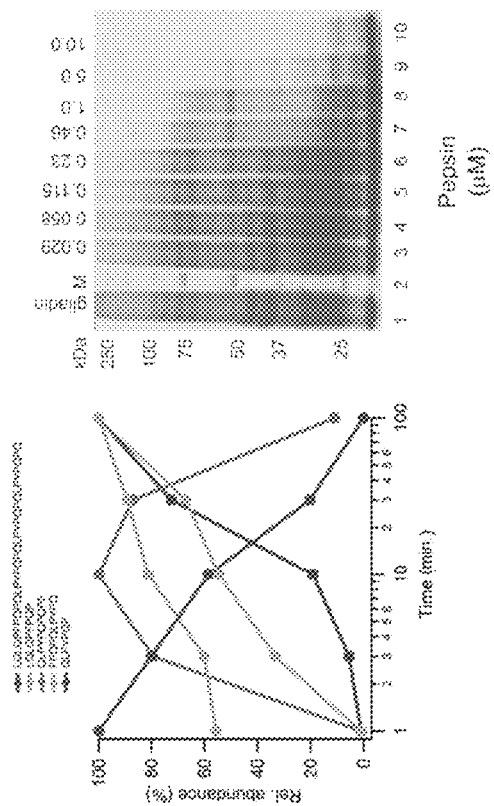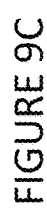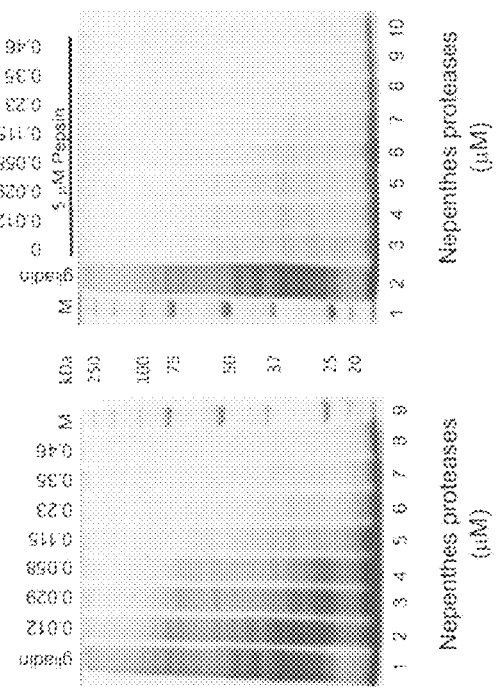

COMPOSITIONS AND METHODS FOR TREATING GLUTEN INTOLERANCE AND DISORDERS ARISING THEREFROM

CROSS REFERENCE TO RELATED APPLICATIONS

The present application claims priority to U.S. Provisional Application No. 62/268,445, filed Dec. 16, 2015, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 26, 2017, is named 107572-0351_SL.txt and is 78,356 bytes in size.

FIELD OF THE INVENTION

Provided herein are compositions and methods for the treatment of gluten intolerance and related conditions, such as celiac disease or gluten sensitivity. Food protein antigens include difficult to digest proline rich foods such as proteins found in wheat, barley, rye, etc. that contain gluten. Gluten, in particular, is partially hydrolyzed in the gastrointestinal tract and can lead to inflammatory response and clinical symptoms. The compositions and methods of this invention provide for reduced amounts of such food protein antigens in the intestine which, in turn, reduces the symptoms of gluten intolerance and celiac disease.

BACKGROUND OF THE INVENTION

Several diseases are mediated by reactions to antigenic food proteins in susceptible individuals. For example, ingestion of wheat, barley, and rye, which contain antigenic food proteins (e.g., gluten) may cause abnormal autoimmune responses, such as celiac disease, wheat allergy and dermatitis herpetiformis, in gluten intolerant individuals. Gluten is a mixture of glutamine- and proline-rich glutenin and prolamin protein molecules.

Celiac disease is an autoimmune disorder affecting the small intestine. Most of the individuals having the abnormal autoimmune responses characteristic of celiac disease express the human leukocyte antigen (HLA) DQ2 or DQ8 molecules. Clinically, celiac disease is detectable, in part, through the quantitation of antibodies specific for gluten and tissue transglutaminase (tTG). The autoimmune responses result in the development of small intestinal mucosal villous atrophy with crypt hyperplasia and mucosal inflammation. Symptoms of celiac disease can vary from individual to individual, and may include one or more of fatigue, chronic diarrhea, constipation, malabsorption of nutrients, weight loss, abdominal distension, anemia, as well as a substantially enhanced risk for the development of osteoporosis and intestinal malignancies (lymphoma and carcinoma).

Symptoms of the disease are caused by a reaction to gluten proteins, and may also include other storage proteins in the grain products consumed (e.g. serpins, purinins). These proteins/prolamins have high levels of proline (15%) and glutamine (35%), in sequence combinations that render them partially resistant to complete proteolysis by gastric enzymes. The sequences convey poor overall digestion kinetics, generating peptides 30-40 amino acid residues in length that resist further digestion by intestinal exo- and endoproteases. A fraction of these products, primarily from α and γ-gliadin, have affinity for human leukocyte antigen (HLA) DQ2 and DQ8, which are MHC class II molecules associated with over 90% of CD patients. The peptides are large enough to span multiple antigenic regions, and present glutamine residues for enzymatic deamidation in the intestine. The inflammatory response is significantly amplified by this deamidation, as HLA affinity is increased by the conversion of glutamine to glutamate.

Type I diabetes is a risk factor for celiac disease. Autism is also associated with celiac disease, and a gluten-free diet may help alleviate some symptoms of autism. Similarly, it is believed that some people with attention deficit hyperactivity disorder exhibit fewer symptoms when gluten is removed from their diets. Other conditions that may benefit from elimination of dietary gluten include rheumatoid arthritis and fibromyalgia.

Treatment for gluten intolerance, especially celiac disease, commonly involves a lifelong, strict gluten-free diet. However, gluten-free diet is inconvenient, restrictive, and gluten is difficult to avoid. Therefore, effective alternative treatments of gluten intolerance and celiac disease are needed

SUMMARY OF THE INVENTION

This invention relates to the discovery that administration of a pharmaceutical composition comprising one or more *Nepenthes* enzymes as described herein results in a decrease in symptoms arising from immune response to the food antigens, including gluten intolerance and celiac disease. In particular, administration of the composition at a ratio of between 1000:1 and 15000:1 (total protein to enzyme) is believed to be sufficient to reduce antigenicity of the proteins (in particular gluten peptides) while maintaining safety and tolerability of the composition.

The toxic properties of gluten proteins (e.g., gliadins and glutenins) are believed to be largely due to proline- and glutamine-rich peptides that are produced during incomplete degradation of the proteins by human digestive enzymes (including pepsin). Gastric and pancreatic endoproteases are unable to cleave these toxic or immunogenic peptide byproducts of incomplete degradation, at least in part due to the fact that such enzymes lack specificity for proline and/or glutamine. These peptides are believed to cause numerous intestinal symptoms in sensitive individuals, including intraepithelial lymphocytosis, villous atrophy, and/or inflammation. Other proteins present in wheat may also be implicated in the autoimmune response, including serpins, purinins, alpha-amylase/protease inhibitois, globulins, and farinins.

T cells are a first responder to antigenic insult (i.e., presence of toxic food peptides) in a sensitive individual. T cells react quickly to antigen insult and cause inflammation and, in some cases, degradation of the intestine. A reduction in T cells in the intestine thus indicates a decreased immune response, and is a potential indicator of reduced or eliminated symptoms associated with immunogenic food (e.g., gluten) consumption in sensitive individuals.

Without being bound by theory, it is believed that contacting gluten (or other antigenic protein) with a pharmaceutical composition as described herein breaks down the protein into small polypeptide fragments that reduces or eliminates an immune response (i.e., are not toxic or are less toxic).

It is contemplated that a pharmaceutical composition as described herein can be used to degrade dietary proteins, particularly proline- and/or glutamine-rich proteins that are not effectively degraded by digestive tract enzymes. It is further contemplated that such degradation would increase absorption of the proteins and/or decrease immunogenicity. Such a result may have beneficial effects on the symptoms of intestinal diseases and disorders (e.g., celiac disease, gluten intolerance, irritable bowel syndrome, colitis, Crohn's disease, food allergies and the like). In one embodiment, administration of the pharmaceutical composition improves nutrient absorption.

Enzyme supplementation of the GI tract has emerged as a possible therapy to blunt the immune response to antigenic peptides, including those resulting from digestion of gluten, by reducing peptide size in the key antigenic regions that trigger inflammation. A small number of candidates have been tested for such purposes, mostly involving prolyl endoproteases (PEPs) or prolyl oligopeptidases (POPs). Two options in advanced testing are AN-PEP, a prolyl endoprotease from *Aspergillus niger*, and ALV003, a combination of a POP from *Sphingomonas* capsulate and a glutamine-targeting cysteine endoprotease.

However, the complexity of the total protein load in a typical meal should define the supplementation strategy and the appropriate dosage. Food products such as dairy, red meat and fish contain proteins with high levels of proline, and will increase the substrate load for therapies dependent solely upon prolyl endoproteases. For example, proline is the most abundant amino acid in beta-casein, at roughly the same fractional level as gliadin. A cheese sandwich would contribute not only 1.6 g of gliadin but also 1.8 g of beta casein, doubling the substrate load for PEP-based therapies. Total protein is therefore a safer measure of substrate load when considering enzyme-based gluten detoxification therapies as an alternative to a gluten free diet; average total protein consumption is estimated at between 20 g and 75 g per day, preferably about 50 g per day. Achieving efficacy at a reasonable dosage remains an obstacle to replacing a gluten free diet as the therapy of choice for celiac disease. The above-mentioned enzyme supplementation candidates appear best suited to supplementing a gluten free diet in situations of limited consumption.

The pitcher secretions of *Nepenthes*, a carnivorous pitcher plant commonly known as monkey cups in tropical regions, include a number of proteases. Concentrated *Nepenthes* pitcher fluid has high specificity for proline- and glutamine-rich gluten peptides. U.S. Patent Application Publication Nos. 2014/0186330 and 2014/0140980, incorporated herein by reference in their entireties, describe the activity and specificity of concentrated *Nepenthes* pitcher fluid and recombinant *Nepenthes* enzymes. The pitcher fluid is acidic, and the enzymes therein are generally most active at acidic pH.

Nepenthesin (EC 3.4.23.12) is an aspartic protease that can be isolated or concentrated from *Nepenthes* pitcher secretions, as well as a variety of other plant sources. Tókés et al., Digestive Enzymes Secreted by the Carnivorous Plant *Nepenthes macferlanei* L., Planta (Berl.) 119, 39-46 (1974). It has been found that the activity of nepenthesin is higher than that of pepsin (EC 3.4.23.1), an enzyme present in the stomach of humans that is partly responsible for degrading food proteins into peptides. Nepenthesin has two known isotypes: nepenthesin I (known to have two variants: nepenthesin Ia and nepenthesin Ib) and nepenthesin II.

A novel prolyl endopeptidase, neprosin, possesses a high proteolytic activity for cleaving proline-rich proteins and oligopeptides (such as gluten proteins). Neprosin can be isolated or concentrated from the pitcher secretions of *Nepenthes*, is active at a broad pH range, and is especially active at low pH (e.g., about 3 to 5). The neprosin protein sequence is not homologous to any other known protein in the genomic databases. Neprosin can efficiently cleave peptides on the carboxy (C)-terminal side of proline. This cleavage appears to be highly specific. Neprosin has been described in U.S. Patent Publication No. 2016/0022785, which is incorporated herein by reference in its entirety.

Neprosin, nepenthesin I, and nepenthesin II, alone or in combination, are able to cleave toxic food peptides into smaller, non-toxic peptides at a high protein-to-enzyme ratio. Because the enzymes are active at a broad acidic pH range, digestion by the enzymes can initiate in the acidic environment of the stomach.

In one embodiment, intestinal inflammation is characterized by infiltration and/or proliferation of IELs in the intestine. Accordingly, in one aspect, this invention is directed to a method for attenuating or preventing intestinal inflammation due to the presence of peptidic food antigen(s) in the intestine of a mammal, which method comprises administering to the mammal an effective amount of a pharmaceutical composition comprising at least one *Nepenthes* enzyme. In one embodiment, the amount of the pharmaceutical composition is effective to attenuate or prevent intestinal inflammation due to the presence of the peptidic food antigen(s). In one embodiment, the intestinal inflammation is due to incomplete digestion of a potentially antigenic food protein by endogenous gastric and/or intestinal enzymes.

In one aspect, this invention is directed to a method for attenuating or preventing intraepithelial lymphocytosis due to the presence of peptidic food antigen(s) in an intestine of a mammal, which method comprises administering to the mammal an effective amount of a pharmaceutical composition comprising at least one *Nepenthes* enzyme. In one embodiment, the amount of the pharmaceutical composition is effective to inhibit intraepithelial lymphocytosis in the intestine.

In one embodiment, the composition is administered to the mammal prior to ingestion of a potentially antigenic food or protein. In one embodiment, the composition is administered to the mammal with ingestion of a potentially antigenic food or protein. In one embodiment, the composition is administered to the mammal after ingestion of a potentially antigenic food. In one embodiment, the composition is administered to the mammal irrespective of consumption of a potentially antigenic food or protein. In one embodiment, the potentially antigenic protein is gluten. In one embodiment, the potentially antigenic protein is one or more wheat proteins.

In one embodiment, the effective amount of the pharmaceutical composition is between about 1 mg and about 1 g. In one embodiment, the effective amount of the pharmaceutical composition depends on the amount of potentially antigenic protein consumed. Preferably, the composition is administered at a total protein to enzyme ratio of between 100:1 and 15000:1.

In one embodiment, the *Nepenthes* enzyme is concentrated, isolated, or extracted from the pitcher fluid of a *Nepenthes* plant. In one embodiment, the *Nepenthes* enzyme comprises recombinant nepenthesin I, recombinant nepenthesin II, recombinant neprosin, a variant thereof, or a mixture thereof.

In one embodiment, the variant thereof comprises a protein, the amino acid sequence of which has at least 85% sequence homology to the amino acid sequence selected from the group consisting of SEQ ID NO.:1, SEQ ID NO.: 5, SEQ ID NO.: 6, SEQ ID NO.: 7, SEQ ID NO.: 8, SEQ ID NO.: 9, SEQ ID NO.: 20, and SEQ ID NO.: 21. In one embodiment, the variant thereof comprises a protein, the amino acid sequence of which has at least 85% sequence homology to the amino acid encoded by the cDNA selected from the group consisting of SEQ ID NO.:2, SEQ ID NO.:4, and SEQ ID NO.:14.

In one embodiment, the food is a liquid. In one aspect, the food is a solid. In a preferred embodiment, the pharmaceutical composition is orally administered.

In one embodiment, the pharmaceutical composition is administered irrespective of whether the patient has ingested (e.g., knowingly ingested) a food containing a potentially immunogenic protein. In one embodiment, the pharmaceutical composition is administered on an as-needed basis, e.g., before, during, and/or after a meal that might be contaminated by a potentially immunogenic protein, or in which the potentially immunogenic protein content is unknown. In one embodiment, the pharmaceutical composition is administered on a regular basis. In one embodiment, the pharmaceutical composition is administered at least one time per day. In one embodiment, the pharmaceutical composition is administered two, three, four, or more times per day. In one embodiment, the pharmaceutical composition is administered in conjunction with (e.g., before, during, or after) each meal and/or snack. In one embodiment, the pharmaceutical composition is included as part of a sustained release formulation where there is a continuous release of enzyme(s) to allow for intermittent snacking, etc. without regard to the antigenic protein content of the food.

In one embodiment, the pharmaceutical composition is maintained in an aqueous system at about pH 2 wherein the free amino groups of said enzyme are charged. In one embodiment, the composition is maintained at neutral pH prior to contact with acids in the stomach. In one embodiment, the pharmaceutical composition comprises a pharmaceutically acceptable buffer, such that the pH of the composition remains at pH 5 or 6 upon contact with acids in the stomach.

In one embodiment, the effective amount of pharmaceutical composition is between about 1 mg and about 1 g. Preferably, the effective amount of pharmaceutical composition is between about 1 mg and about 10 mg. More preferably, the effective amount of pharmaceutical composition is less than about 5 mg per day.

In one embodiment, the effective amount of pharmaceutical composition is between about 1 mg and about 1 g per 1 g substrate (e.g., gluten or other potentially immunogenic protein, or total protein). In one embodiment, the effective amount of pharmaceutical composition is between about 1 mg and about 20 mg per 50 grams total daily protein. In a preferred embodiment, the effective amount of pharmaceutical composition is between about 1 mg and about 10 mg per 50 grams total daily protein.

In one embodiment, the pharmaceutical composition comprises more than one of nepenthesin I, nepenthesin II, neprosin, or a variant thereof.

In one embodiment, the mammal is a human. In one aspect, the human suffers from gluten sensitivity or celiac disease. In one aspect, it is contemplated that intestinal antigen protein sensitivity correlates, directly or indirectly, with attention deficit hyperactivity disorder, autism, rheumatoid arthritis, fibromyalgia, and/or dermatitis herpetiformis. It is further contemplated that removing such antigenic intestinal proteins from the intestine using compositions of this invention will have a positive effect on attention deficit hyperactivity disorder, autism, rheumatoid arthritis, fibromyalgia, and/or dermatitis herpetiformis. In a preferred embodiment, the human suffers from celiac disease.

In one aspect, this invention is directed to a pharmaceutical composition comprising an effective amount of nepenthesin I, nepenthesin II, neprosin, variant thereof, or a mixture thereof to reduce toxic peptide content of ingested protein that travels to the intestine. In a preferred embodiment, the pharmaceutical composition comprises neprosin or a variant and/or salt thereof. In a further preferred embodiment, the pharmaceutical composition further comprises at least one additional *Nepenthes* enzyme. In one embodiment, the additional *Nepenthes* enzyme comprises nepenthesin I, nepenthesin II, a variant thereof, and/or a salt thereof.

Without being bound by theory, it is believed that nepenthesin I, nepenthesin II, and neprosin are less active or substantially inactive at neutral to basic pH. This can be important where there is a potential for undesirable digestion by the enzyme(s). For example, where the pharmaceutical composition is administered orally, buffering of the composition to pH 5, pH 6, pH 6.5, or greater may result in a less active form of the enzyme(s) such that the oral mucosa, esophageal mucosa, and other cells that may come into contact with the composition will not be digested by the enzyme(s) therein. Likewise, when the composition is added to a food, the buffered enzyme(s) will be unable to (or less able to) digest the food before it is consumed. In such situations, introduction of the composition to the acidic environment of the stomach will result in a decrease in the pH and activation of enzyme(s).

In one embodiment, the pharmaceutical composition is buffered to about pH 5, pH 6, or pH 6.5 or higher. In a preferred embodiment, the composition is buffered to about pH 5 to about pH 8.5. In one embodiment, the composition is in liquid form. In one embodiment, the composition is in solid form. In one embodiment, the pH of the composition is adjusted in liquid form and the composition is dried to form a solid.

In one embodiment, the pharmaceutical composition comprises one or more additional proteases. In one embodiment, the one or more additional protease is an aspartic protease, a serine protease, a threonine protease, a cysteine protease, a glutamic acid protease, or a metalloprotease. In one embodiment, the pharmaceutical composition comprises one or more additional exoproteases, such as, leucine aminopeptidases and carboxypeptidases. In one embodiment, the one or more additional protease is trypsin. In a preferred embodiment, the one or more additional protease is active at acidic pH (e.g., pH 2-6).

In one aspect, the invention is directed to a formulation comprising the pharmaceutical composition of the invention, wherein the enzyme(s) is present in a delayed release vehicle such that the enzyme(s) is released continuously while the formulation is present in the stomach. In one embodiment, the formulation has a pH of greater than about 5 prior to contact with acids in the stomach. In one embodiment, the formulation comprises a biologically acceptable buffer, such that the pH of the composition remains at about pH 5 or 6 for at least a period of time upon contact with acids in the stomach.

In one embodiment, the invention is directed to a unit dose formulation of the pharmaceutical composition. For example and without limitation, the unit dose may be present in a tablet, a capsule, and the like. The unit dose may be in solid, liquid, powder, or any other form.

Without being bound by theory, it is envisioned that a unit dose formulation of the pharmaceutical composition will allow for proper dosing (e.g., based on the amount of immunogenic protein ingested) while avoiding potential negative side effects of administering an excessive amount of the composition.

In one embodiment, the invention is directed to a proenzyme form of the nepenthesin I, nepenthesin II, neprosin, and/or variant thereof. In one embodiment, a propeptide is present on the enzyme. In a preferred embodiment, the propeptide is removed by acidic pH, thereby activating the enzyme. In one embodiment, the propeptide comprises the naturally-occurring propeptide amino acid sequence for the enzyme. In one embodiment, the propeptide is an artificial propeptide or a meterologous propeptide (i.e., an acid-labile propeptide from a different protein and/or species).

BRIEF DESCRIPTION OF THE DRAWINGS

FIG. 2A shows the relative digestion activity profile of concentrated fluid as a function of pH, compared with gastric pepsin (substrate: hemoglobin). (mean+/−std. dev. for n=3).

FIG. 2B shows the effect of proteolytic inhibitors on digestion of bovine serum albumin (BSA) measured by SDS PAGE. Inhibitors: PMSF (phenylmethylsulfonyl fluoride), P (pepstatin), L (leupeptin), E (EDTA and EGTA), DTT (dithiothreitol), ZPP (Z-Pro-Pro-aldehyde-dimethyl acetal). All inhibitor concentrations at 1 mM except where noted. Extract: fluid protein extract, M: lane markers.

FIG. 2C shows a gravimetric analysis of crude gliadin slurry digested with aliquots of extract. Inset: temporal profiling of slurry (left to right: 0, 30, 60, 90 min) using the protein-enriched fluid extract.

FIG. 2D shows a silver-stain SDS PAGE of protein-enriched fluid showing the limited complexity of the fraction, and its high proteolytic stability in the presence of pepsin.

Figure 4C:
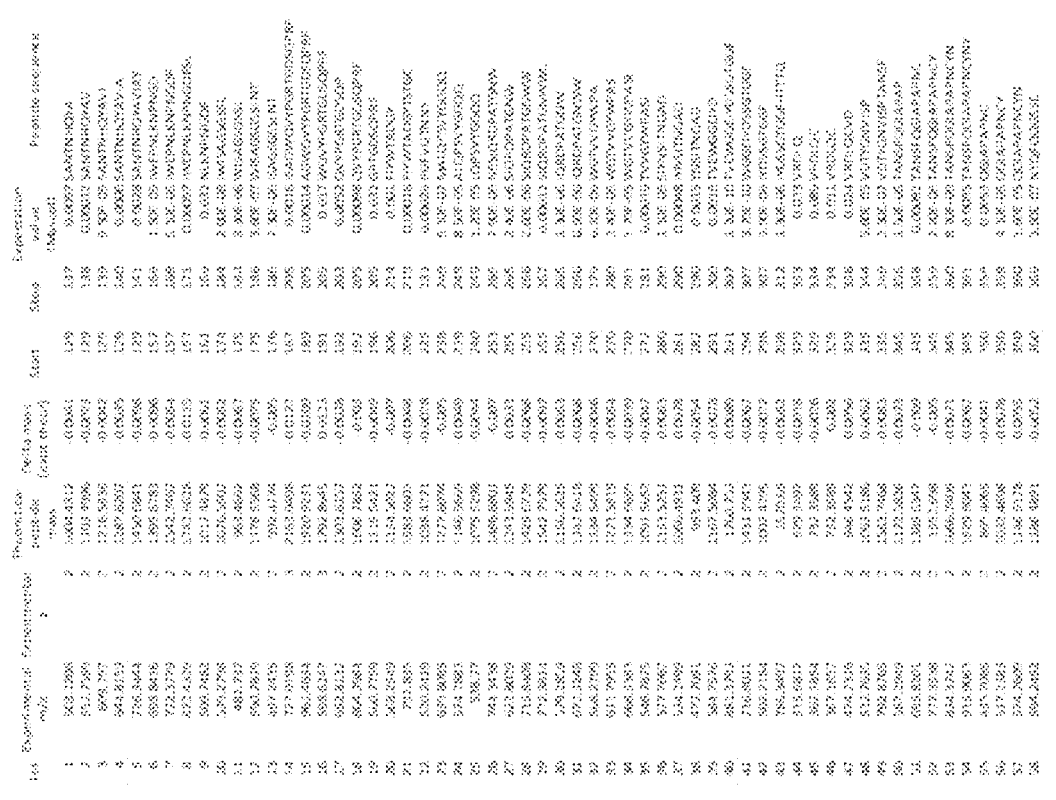

FIG. 4C shows peptides identified from a non-specific (peptic) digestion of isolated, denatured neprosin, supporting the sequence identified using 5' and 3' RACE (51% coverage). Output represents the unique peptides detected using Mascot v2.3, filtered for p<0.05. Figure discloses SEQ ID NOS 30-74 and 74-86, respectively, in order of appearance.

FIG. 5A shows domain organization of Npr and other DUF239 family members (Pf3080). Most entries in the Pfam database contain DUF4409 and DUF239 in tandem, and most possess a signal peptide. The category of "other" includes various domain repeats and DUF4409 alone.

FIG. 6 shows a comparison between neprosin and known proline-cleaving enzymes that have been studied for gluten detoxification and highlights the sequence, functional, or structural dissimilarities with known proline-cleaving enzymes.

FIG. 8A shows a time-course digestion of 10 mg/ml gliadin (pH 2.5 at 37° C.) with the indicated micromolar concentrations of pepsin. Turbidity of the digested gliadin was monitored as absorbance at 595 nm ($A_{595}$). Black lines represent the turbidity of the gliadin slurry in the absence of protease. Measurement precision was <3% RSD (n=3).

FIG. 8B shows a time-course digestion of 10 mg/ml gliadin (pH 2.5 at 37° C.) with the indicated micromolar concentrations of *Nepenthes* fluid proteases. Turbidity of the digested gliadin was monitored as absorbance at 595 nm ($A_{595}$). Black lines represent the turbidity of the gliadin slurry in the absence of protease. Measurement precision was <3% RSD (n=3).

FIG. 9A shows a digestion profile of α-gliadin peptide 33mer at 20:1 (gliadin:enzyme), using fluid proteases under dilute conditions. Normalized relative abundance measured from LC-MS ion chromatograms, using caffeine as internal standard. Figure discloses SEQ ID NOS 88, 28, and 89-91, respectively, in order of appearance.

FIG. 9B shows SDS-PAGE of 10 mg/ml gliadin digested with the indicated concentration of pepsin. Digestions at pH 2.5 and 37° C., for 90 min. All concentrations in μM. M: Molecular weight markers, and gliadin: total crude gliadin in the absence of protease.

FIG. 9C shows SDS-PAGE of 10 mg/ml gliadin digested with the indicated concentration of fluid proteases. Digestions at pH 2.5 and 37° C., for 90 min. All concentrations in μM. M: Molecular weight markers, and gliadin: total crude gliadin in the absence of protease.

FIG. 9D shows SDS-PAGE of 10 mg/ml gliadin digested with the indicated concentration of pepsin in combination with fluid proteases. Digestions at pH 2.5 and 37° C., for 90 min. All concentrations in μM. M: Molecular weight markers, and gliadin: total crude gliadin in the absence of protease.

DETAILED DESCRIPTION OF THE INVENTION

Figure 1A:
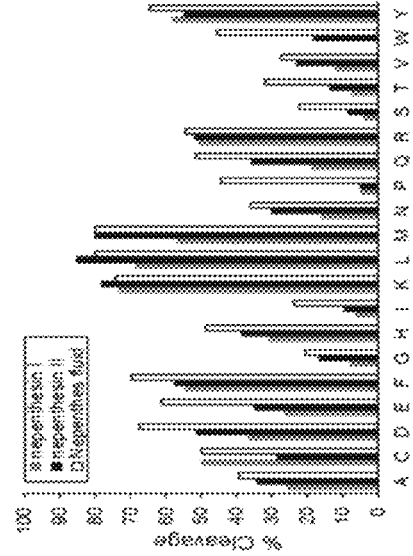
FIG. 1A shows characterization and stability testing of protein concentrate from stimulated *Nepenthes* fluid. C-terminal cleavage preferences (P1 position) as a function of storage time at elevated temperature. Fluid concentrate was incubated at 37° C. for 0-7 days. No alteration of the broadly non-specific digestion character of the extract is observed over time. The global reduction correlates with a modest overall reduction in total activity as measured using the hemoglobin assay (not shown). Data were collected from 2-minute in-solution digestions of protein standards at 37° C. (pH 2.5), and cleavage preferences were determined using LC-MS/MS methods. For each amino acid, cleavage preferences were estimated by calculating the number observed terminal residues relative to the total number of residues, in percent.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section.

I. Definitions

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

As used in the specification and claims, the singular form "a", "an" and "the" include plural references unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

As used herein, a "potentially antigenic food or protein" is any food or protein that can cause an immune and/or inflammatory response in the intestine of a sensitive individual. In a preferred embodiment, the individual is a human and the food is a food intended for human consumption. Potentially antigenic foods include, without limitation, wheat, rye, barley, peanuts, nuts and seeds. In one embodiment, potentially antigenic proteins from these foods include prolamin proteins, 2S albumins, non-specific lipid transfer proteins, bifunctional α-amylase/protease inhibitors, soybean hydrophobic protein, indolines, gluten, serpins, purinins, alpha-amylase/protease inhibitors, globulins, and farinins. In a preferred embodiment, the potentially antigenic protein (or peptide) is rich in proline and/or glutamine residues. In an especially preferred embodiment, the potentially antigenic protein is gluten. In another preferred embodiment, the potentially antigenic protein is a wheat protein.

As used herein, the term "gluten" generally refers to the proteins present in wheat or related grain species, including barley and rye, which have potential harmful effect to certain individuals. Gluten proteins include gliadins such as α-gliadins, β-gliadins, γ-gliadins and ω-gliadins, which are monomeric proteins, and glutenins, which are highly heterogeneous mixtures of aggregates of high-molecular-weight and low-molecular-weight subunits held together by disulfide bonds. Many wheat gluten proteins have been characterized. See, for example, Woychik et al., Amino Acid Composition of Proteins in Wheat Gluten, *J. Agric. Food Chem.,* 9(4), 307-310 (1961). The term gluten as used herein also includes oligopeptides that can be derived from normal human digestion of gluten proteins from gluten containing foods and cause the abnormal immune response. Some of these oligopeptides are resistant to normal digestive enzymes. Gluten, including the above-mentioned proteins and oligopeptides, is believed to act as an antigen for T cells (e.g., IELs) in patients with gluten intolerance (e.g., celiac sprue). The term gluten also refers to denatured gluten, such as would be found in baked products.

As used herein, the term "gluten sensitivity and related conditions" refers to any condition stemming from intolerance or sensitivity to gluten proteins or peptides. These include, without limitation, celiac sprue (celiac disease), wheat allergy, gluten sensitivity, gluten-sensitive enteropathy, idiopathic gluten sensitivity, and dermatitis herpetiformis. Related conditions also include, without limitation, autism, attention deficit hyperactivity disorder (ADHD), rheumatoid arthritis, fibromyalgia, Crohn's disease, nutrient maladsorption, and irritable bowel syndrome (IBS).

The term "neprosin" refers to a prolyl endoprotease with a molecular weight of approximately 29 kilo Daltons (kDa). Neprosin can be isolated from the pitcher secretions of *Nepenthes* species. Neprosin cleaves proteins carboxy-terminal to proline, with high specificity. The enzyme is active at about pH 2 to about pH 6. In one embodiment, neprosin has the amino acid sequence of SEQ ID NO.: 1. The neprosin amino acid sequence is not homologous to any other known protein. In one embodiment, neprosin is encoded by the cDNA sequence of SEQ ID NO.: 2. In one embodiment, neprosin comprises a signal sequence. In one embodiment, the signal sequence comprises the amino acid sequence of SEQ ID NO.: 3. In one embodiment, neprosin does not comprise a signal sequence.

Neprosin includes all isoforms, isotypes, and variants of neprosin, recombinant neprosin, and salts thereof. Salts refer to those salts formed by neprosin with one or more base or one or more acid which retain the biological effectiveness and properties of the free neprosin, and which are not biologically or otherwise undesirable. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Acids that can form salts include, but are not limited to, inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

Examples of proteases include, without limitation, aspartic proteases, serine proteases, threonine proteases, cysteine proteases, glutamic acid proteases, and metalloproteases. Proteases that can be useful in the present invention include, without limitation, BACE, cathepsin D, cathepsin E, chymosin (or "rennin"), napsin, pepsin, plasmepsin, presenilin, renin, trypsin, chemotrypsin, elastase, and cysteine endoprotease (EP) B2 (also known as EPB2). Proteases include those described, for example, in U.S. Pat. Nos. 7,320,788; 7,303,871; 7,320,788; 7,628,985; 7,910,541; and 7,943,312; PCT Pat. Pub. Nos. 2005/107786; 2008/115428; 2008/115411; 2010/021752; 2010/042203; 2011/097266 each of which is expressly incorporated herein by reference. In a preferred embodiment, the at least one additional protease is active at acidic pH, such as that found in the stomach (e.g., pH 1.5 to 3.5).

The term "nepenthesin" refers to the aspartic protease having the Enzyme Commission number EC 3.4.23.12, and includes all isoforms, isotypes, and variants of nepenthesin such as nepenthesin I and nepenthesin II, nepenthesin isoforms, and recombinant nepenthesin, and salts thereof. Nepenthesin (EC 3.4.23.12) is an aspartic protease of plant origin that can be isolated or concentrated from a variety of plant sources, such as the pitcher secretions of *Nepenthes*, a carnivorous pitcher plant, commonly known as monkey cups in tropical regions. Nepenthesin is described in detail in U.S. Pat. No. 9,005,610, which is incorporated herein by reference in its entirety.

In one embodiment, "effective amount" refers to that amount of a composition that results in inhibition or amelioration of symptoms in a subject or a desired biological outcome, e.g., improved clinical signs, delayed onset of disease, etc. The effective amount can be determined by one of ordinary skill in the art. The selected dosage level can depend upon the severity of the condition being treated, and the condition and prior medical history of the mammal being treated. However, it is within the skill of the art to start doses of the composition at levels lower than required to achieve the desired therapeutic effect and to gradually increase the dosage until the desired effect is achieved.

The term "manifestations of celiac disease" refers to any of the symptoms or clinical presentations of celiac disease. Such manifestations include, without limitation, intestinal inflammation, "foggy mind", depression, anxiety, ADHD-like behavior, abdominal pain, bloating, diarrhea, constipation, headaches, migraines, bone or joint pain, chronic fatigue, small intestine damage, development of tissue transglutaminase (tTG) antibodies, severe acne, vomiting, weight loss, irritability, iron-deficiency anemia, arthritis, tingling numbness in the extremities, infertility, and canker sores of the mouth. Manifestations further include small intestinal mucosal villous atrophy with crypt hyperplasia, mucosal inflammation of the intestine, malabsorption of nutrients, abdominal distension, as well as a substantially enhanced risk for the development of osteoporosis and intestinal malignancies (lymphoma and carcinoma).

"Concurrent administration," or "co-treatment," as used herein includes administration of the agents together, or before or after each other.

The term "modulate," "attenuate" or "ameliorate" means any treatment of a disease or disorder in a subject, such as a mammal, including:
  preventing or protecting against the disease or disorder, that is, causing the abnormal biological reaction or symptoms not to develop;
  inhibiting the disease or disorder, that is, arresting or suppressing the development of abnormal biological reactions and/or clinical symptoms; and/or
  relieving the disease or disorder, that is, causing the regression of abnormal biological reactions and/or symptoms.

As used herein, the term "preventing" or "inhibiting" refers to the prophylactic treatment of a subject in need thereof. The prophylactic treatment can be accomplished by providing an appropriate dose of a therapeutic agent to a subject at risk of suffering from an ailment, thereby substantially averting onset of the ailment.

As used herein, the term "condition" refers to a disease state for which the compounds, compositions and methods provided herein are being used.

As used herein, the term "patient" or "subject" refers to mammals and includes humans and non-human mammals. In particular embodiments herein, the patient or subject is a human.

The term "about" when used before a numerical value indicates that the value may vary within a reasonable range: ±5%, ±1%, or ±0.2%.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. One alignment program is BLAST, using default parameters. Examples of the programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

II. Methods

In one aspect, this invention relates to methods for modulating a condition mediated by gluten intolerance in a patient, comprising administering to the patient an effective amount of a pharmaceutical composition comprising a *Nepenthes* enzyme. In a preferred embodiment, the condition is celiac disease or a wheat allergy.

In another aspect, this invention relates to a method for attenuating or preventing production and/or recruitment of IELs in the intestine due to the presence of a peptidic food antigen in an intestine of a mammal. In one embodiment, the method comprises administering to the mammal an effective amount of a pharmaceutical composition comprising a *Nepenthes* enzyme. In one embodiment, the gluten protein is degraded by the pharmaceutical composition so as to attenuate or prevent production and/or recruitment of IELs in the intestine.

In one aspect, this invention relates to a method for attenuating or preventing intestinal inflammation due to the presence of a peptidic food antigen in the intestine of a mammal. In one embodiment, the method comprises administering to the mammal an effective amount of a pharmaceutical composition comprising a *Nepenthes* enzyme. In one embodiment, the peptidic food antigen is degraded by the enzyme(s) so as to attenuate or prevent intestinal inflammation.

In one aspect, this invention relates to a method for attenuating or preventing intraepithelial lymphocytosis due to the presence of a peptidic food antigen in an intestine of a mammal. In one embodiment, the method comprises administering to the mammal an effective amount of a pharmaceutical composition comprising a *Nepenthes* enzyme. In one embodiment, the peptidic food antigen is degraded by the pharmaceutical composition so as to attenuate or prevent intraepithelial lymphocytosis in the intestine.

In one aspect, this invention relates to a method for attenuating or preventing villous atrophy due to the presence of a peptidic food antigen in an intestine of a mammal. In one embodiment, the method comprises administering to the mammal an effective amount of a pharmaceutical composition comprising a *Nepenthes* enzyme. In one embodiment, the peptidic food antigen is degraded by the pharmaceutical composition so as to attenuate or prevent villous atrophy in the intestine. In one embodiment, the villous atrophy is a result of inflammation of the intestine.

In one embodiment, the *Nepenthes* enzyme is nepenthesin I, nepenthesin II, neprosin, variant thereof, or a mixture thereof. In a preferred embodiment, the pharmaceutical formulation is a sustained release formulation.

In one embodiment, the variant is a protein having an amino acid sequence having at least 85% sequence homology to the amino acid sequence of SEQ ID NO.: 1, SEQ ID NO.: 5, SEQ ID NO.: 6, SEQ ID NO.: 7, SEQ ID NO.: 8, SEQ ID NO.: 9, SEQ ID NO.:20, or SEQ ID NO.:21. In one embodiment, the variant is a protein having an amino acid sequence having at least 85% sequence homology to the amino acid sequence of SEQ ID NO.: 1. In one embodiment, the variant is a protein having an amino acid sequence having at least 85% sequence homology to the amino acid sequence of SEQ ID NO.: 5. In one embodiment, the variant is a protein having an amino acid sequence having at least 85% sequence homology to the amino acid sequence of SEQ ID NO.: 6. In one embodiment, the variant is a protein having an amino acid sequence having at least 85% sequence homology to the amino acid sequence of SEQ ID NO.: 7. In one embodiment, the variant is a protein having an amino acid sequence having at least 85% sequence homology to the amino acid sequence of SEQ ID NO.: 8. In one embodiment, the variant is a protein having an amino acid sequence having at least 85% sequence homology to the amino acid sequence of SEQ ID NO.: 9. In one embodiment, the variant is a protein having an amino acid sequence having at least 85% sequence homology to the amino acid sequence of SEQ ID NO.: 20. In one embodiment, the variant is a protein having an amino acid sequence having at least 85% sequence homology to the amino acid sequence of SEQ ID NO.: 21.

In one embodiment, the pharmaceutical composition comprises an extract of *Nepenthes* pitcher fluid. In one embodiment, the pharmaceutical composition comprises nepenthesin I, nepenthesin II, and/or neprosin purified from an extract of *Nepenthes* pitcher fluid. In one embodiment, at least one of nepenthesin I, nepenthesin II, neprosin, or variant thereof is a recombinant protein. In one embodiment, the pharmaceutical composition is between about pH 5 and about pH 8 prior to administration. Pharmaceutical compositions for use in the methods described herein are discussed in more detail below.

In a preferred embodiment, the mammal is a human. In one embodiment, the human suffers from a disease selected from the group consisting of gluten intolerance, celiac disease, attention deficit hyperactivity disorder, autism, rheumatoid arthritis, fibromyalgia, and dermatitis herpetiformis. In one embodiment, the human suffers from a food allergy.

In one embodiment, the pharmaceutical composition is orally administered prior to, during, or immediately after consumption of a gluten-containing food.

In some embodiments, the pharmaceutical composition is administered to the subject prior to ingestion by the subject of the food comprising gluten or suspect of comprising gluten.

In some embodiments, the pharmaceutical composition is administered within a period that the enzyme is at least partially effective (for example, at least about 10%, 20%, 50%, 70%, 90% of original activity) in degrading gluten in the food that the subject will ingest. In some embodiments, the pharmaceutical composition is administered not more than about 4 hours, 3 hours, 2 hours, 1 hour, or 30 minutes prior to ingestion of the food by the subject.

In some embodiments, the pharmaceutical composition is administered to the subject concurrently with ingestion by the subject of the potentially immunogenic food. In some embodiments, the enzyme composition is administered with the food. In some embodiments, the pharmaceutical composition is administered separately from the food.

In some embodiments, the pharmaceutical composition is administered to the subject shortly after ingestion by the subject of the potentially immunogenic food. In some embodiments, the pharmaceutical composition is administered within a period that at least part (for example, at least about 10%, 20%, 50%, 70%, 90%) of the antigen(s) in the food is still in the stomach of the subject. In some embodiments, the pharmaceutical composition is administered not more than 4 hours, 3 hours, 2 hours, 1 hour, or 30 minutes after ingestion of the food by the subject.

Typically, the pharmaceutical composition is administered in an amount that is safe and sufficient to produce the desired effect of detoxification of peptidic food antigen(s). The dosage of the pharmaceutical composition can vary depending on many factors such as the particular enzyme administered, the subject's sensitivity to the food, the amount and types of antigen-containing food ingested, the pharmacodynamic properties of the enzyme, the mode of administration, the age, health and weight of the recipient, the nature and extent of the symptoms, the frequency of the treatment and the type of concurrent treatment, if any, and the clearance rate of the enzyme. One of skill in the art can determine the appropriate dosage based on the above factors. The composition may be administered initially in a suitable dosage that may be adjusted as required, depending on the clinical response. In vitro assays may optionally be employed to help identify optimal dosage ranges. The precise dose to be employed in the formulation will also depend on the route of administration and/or the seriousness of the disease or disorder, and should be decided according to the judgment of the practitioner and each subject's circumstances.

The dosage or dosing regimen of an adult subject may be proportionally adjusted for children and infants, and also adjusted for other administration or other formats, in proportion for example to molecular weight or immune response. Administration or treatments may be repeated at appropriate intervals, at the discretion of the physician.

Generally, the pharmaceutical composition is administered when needed, such as when the subject will be or is consuming or has consumed a food comprising an antigenic protein or suspected of comprising an antigenic protein. In any case, it can be administered in dosages of about 0.001 mg to about 1000 mg of enzyme per kg body weight per day, or about 1 mg to about 100 g per dose for an average person. In some embodiments, the enzyme can be administered at 0.001, 0.01, 0.1, 1, 5, 10, 50, 100, 500, or 1000 mg/kg body weight per day, and ranges between any two of these values (including endpoints). In some embodiments, the enzyme can be administered at 1 mg, 10 mg, 100 mg, 200 mg, 500 mg, 700 mg, 1 g, 10 g, 20 g, 50 g, 70 g, 100 g per dose, and ranges between any two of these values (including endpoints). In some embodiments, it may be administered once, twice, three times, etc. a day, depending on the number of times the subject ingests a food comprising an antigenic protein and/or how much of such food is consumed. The amount of enzyme recited herein may relate to total enzyme or each enzyme in the composition.

In some embodiments, the amount of pharmaceutical composition administered is dependent on the amount (or approximate amount) of substrate (e.g., gluten and/or other protein or potentially antigenic protein) consumed/to be consumed. In one embodiment, about 1 mg to about 1 g of enzyme is administered per 1 g of substrate. In one embodiment, about 5 mg to about 1 g of enzyme is administered per 1 g of substrate. In one embodiment, about 10 mg to about 1 g of enzyme is administered per 1 g of substrate. In one embodiment, about 100 mg to about 1 g of enzyme is administered per 1 g of substrate. In one embodiment, about 1 mg to about 500 mg of enzyme is administered per 1 g of substrate. In one embodiment, about 1 mg to about 250 mg of enzyme is administered per 1 g of substrate. In one embodiment, about 1 mg to about 100 mg of enzyme is administered per 1 g of substrate. In one embodiment, about 1 mg to about 10 mg of enzyme is administered per 1 g of substrate. This includes any values within any of these ranges (including endpoints), and subranges between any two of these values.

In one embodiment, the effective amount of pharmaceutical composition is between about 1 mg and about 1 g. Preferably, the effective amount of pharmaceutical composition is between about 1 mg and about 10 mg. More preferably, the effective amount of pharmaceutical composition is less than about 5 mg per day. In one embodiment, the effective amount of pharmaceutical composition is between about 10 mg and about 1 g. In one embodiment, the effective amount of pharmaceutical composition is between about 20 mg and about 1 g. In one embodiment, the effective amount of pharmaceutical composition is between about 30 mg and about 1 g. In one embodiment, the effective amount of pharmaceutical composition is between about 40 mg and about 1 g. In one embodiment, the effective amount of pharmaceutical composition is between about 50 mg and about 1 g. In one embodiment, the effective amount of pharmaceutical composition is between about 60 mg and about 1 g. In one embodiment, the effective amount of pharmaceutical composition is between about 70 mg and about 1 g. In one embodiment, the effective amount of pharmaceutical composition is between about 80 mg and about 1 g. In one embodiment, the effective amount of pharmaceutical composition is between about 100 mg and about 1 g. In one embodiment, the effective amount of pharmaceutical composition is between about 500 mg and about 1 g. In one embodiment, the effective amount of pharmaceutical composition is between about 1 mg and about 500 mg. In one embodiment, the effective amount of pharmaceutical composition is between about 1 mg and about 250 mg. In one embodiment, the effective amount of pharmaceutical composition is between about 1 mg and about 200 mg. In one embodiment, the effective amount of pharmaceutical composition is between about 1 mg and about 100 mg. In one embodiment, the effective amount of pharmaceutical composition is between about 1 mg and about 90 mg. In one embodiment, the effective amount of pharmaceutical composition is between about 1 mg and about 80 mg. In one embodiment, the effective amount of pharmaceutical composition is between about 1 mg and about 70 mg. In one embodiment, the effective amount of pharmaceutical composition is between about 1 mg and about 60 mg. In one embodiment, the effective amount of pharmaceutical composition is between about 1 mg and about 50 mg. In one embodiment, the effective amount of pharmaceutical composition is between about 1 mg and about 40 mg. In one embodiment, the effective amount of pharmaceutical composition is between about 1 mg and about 30 mg. In one embodiment, the effective amount of pharmaceutical composition is between about 1 mg and about 20 mg. In one embodiment, the effective amount of pharmaceutical composition is between about 1 mg and about 5 mg. In one embodiment, the effective amount of pharmaceutical composition is between about 1 mg and about 4 mg. In one embodiment, the effective amount of pharmaceutical composition is between about 1 mg and about 3 mg. This includes any values within any of these ranges (including endpoints), and subranges between any two of these values.

In one embodiment, the ratio of substrate (total protein) to enzyme (single *Nepenthes* enzyme or combination of *Nepenthes* enzymes) administered is between about 1:1 and about 15000:1. In one embodiment, the ratio of substrate to enzyme is between about 10:1 and about 15000:1. In one embodiment, the ratio of substrate to enzyme is between about 100:1 and about 15000:1. In one embodiment, the ratio of substrate to enzyme is between about 500:1 and about 15000:1. In one embodiment, the ratio of substrate to enzyme is between about 1000:1 and about 15000:1. In one embodiment, the ratio of substrate to enzyme is between about 5000:1 and about 15000:1. In one embodiment, the ratio of substrate to enzyme is between about 10000:1 and about 15000:1. In one embodiment, the ratio of substrate to enzyme is between about 1:1 and about 10000:1. In one embodiment, the ratio of substrate to enzyme is between about 10:1 and about 10000:1. In one embodiment, the ratio of substrate to enzyme is between about 100:1 and about 10000:1. In one embodiment, the ratio of substrate to enzyme is between about 500:1 and about 10000:1. In one embodiment, the ratio of substrate to enzyme is between about 1000:1 and about 10000:1. In one embodiment, the ratio of substrate to enzyme is between about 5000:1 and about 10000:1. In one embodiment, the ratio of substrate to enzyme is between about 1:1 and about 5000:1. In one embodiment, the ratio of substrate to enzyme is between about 10:1 and about 5000:1. In one embodiment, the ratio of substrate to enzyme is between about 100:1 and about 5000:1. In one embodiment, the ratio of substrate to enzyme is between about 500:1 and about 5000:1. In one embodiment, the ratio of substrate to enzyme is between about 1000:1 and about 5000:1. In one embodiment, the ratio of substrate to enzyme is between about 1:1 and about 1000:1. In one embodiment, the ratio of substrate to enzyme is between about 10:1 and about 1000:1. In one embodiment, the ratio of substrate to enzyme is between about 100:1 and about 1000:1. In one embodiment, the ratio of substrate to enzyme is between, about 1:1 and about 500:1. In one embodiment, the ratio of substrate to enzyme is between about 10:1 and about 500:1. In one embodiment, the ratio of substrate to enzyme is between about 100:1 and about 500:1. In one embodiment, the ratio of substrate to enzyme is between about 1:1 and about 100:1. In one embodiment, the ratio of substrate to enzyme is between about 10:1 and about 100:1. This includes any values within any of these ranges (including endpoints), and subranges between any two of these values.

Total protein may be, for example, the total protein consumed at a given meal, or the total protein consumed in a specific period of time (e.g., in an hour, 2 hours, or 3-24 hours). In one embodiment, the total protein is the total of all protein consumed by the subject in a 1-hour period. In one embodiment, the total protein is the total of all protein consumed by the subject in a 2-hour period. In one embodiment, the total protein is the total of all protein consumed by the subject in a 3-hour period. In one embodiment, the total protein is the total of all protein consumed by the subject in a 4-hour period. In one embodiment, the total protein is the total of all protein consumed by the subject in a 5-hour period. In one embodiment, the total protein is the total of all protein consumed by the subject in a 10-hour period. In one embodiment, the total protein is the total of all protein consumed by the subject in a 12-hour period. In one embodiment, the total protein is the total of all protein consumed by the subject in a 15-hour period. In one embodiment, the total protein is the total of all protein consumed by the subject in a 20-hour period. In one embodiment, the total protein is the total of all protein consumed by the subject in a 24-hour period.

The pharmaceutical composition of this invention can be administered as the sole active agent or they can be administered in combination with other agents (simultaneously, sequentially or separately, or through co-formulation), including other compounds that demonstrate the same or a similar therapeutic activity and that are determined to safe and efficacious for such combined administration.

In some embodiments, the pharmaceutical composition is administered with an additional enzyme, such as a gastric protease, an aspartic protease (such as pepsin, pepsinogen or those described by Chen et al., Aspartic proteases gene family in rice: Gene structure and expression, predicted protein features and phylogenetic relation, *Gene* 442:108-118 (2009)), and enzymes such as another prolyl endopeptidase (PEP), dipeptidyl peptidase IV (DPP IV), and dipeptidyl carboxypeptidase (DCP) or cysteine proteinase B (described in U.S. Pat. No. 7,910,541). In one embodiment, the other enzyme is administered in the form of bacteria that produce and/or secrete the additional enzyme. In one embodiment, the bacteria are engineered to produce and/or secrete nepenthesin I, nepenthesin II, neprosin, and/or a variant thereof.

In some embodiments, the pharmaceutical composition is administered to the subject with another agent. Non-limiting examples of agents that can be administered with the pharmaceutical composition include inhibitors of tissue transglutaminase, anti-inflammatory agents such as amylases, glucoamylases, endopeptidases, HMG-CoA reductase inhibitors (e.g., compactin, lovastatin, simvastatin, pravastatin and atorvastatin), leukotriene receptor antagonists (e.g., montelukast and zafirlukast), COX-2 inhibitors (e.g., celecoxib and rofecoxib), p38 MAP kinase inhibitors (e.g., BIRB-796); mast cell-stabilizing agents such as sodium chromoglycate (chromolyn), pemirolast, proxicromil, repirinast, doxantrazole, amlexanox nedocromil and probicromil, anti-ulcer agents, anti-allergy agents such as anti-histamine agents (e.g., acrivastine, cetirizine, desloratadine, ebastine, fexofenadine, levocetirizine, loratadine and mizolastine), inhibitors of transglutaminase 2 (TG2), anti-TNFα agents, and antibiotics. In one embodiment, the additional agent is a probiotic. Probiotics include, without limitation, *lactobacillus*, yeast, *bacillus*, or *bifidobacterium* species and strains. In one embodiment, the other agent is elafin. In one embodiment, the other agent is administered in the form of bacteria that produce and/or secrete the additional agent.

In some embodiments, the other agent comprises an enzyme (e.g., protease) that is active in the intestine. Without being limited by theory, it is believed that such enzymes may act synergistically with the enzyme(s) of the pharmaceutical composition to further degrade immunogenic proteins Also provided herein is the use of an enzyme composition comprising nepenthesin I, nepenthesin II, neprosin, a variant thereof, and/or a salt thereof in the manufacture of a medicament for the treatment or prevention of one of the aforementioned conditions and diseases.

III. Pharmaceutical Compositions

The pharmaceutical composition can be administered in a variety of compositions alone or with appropriate, pharmaceutically acceptable carriers, excipients, or diluents.

Accordingly, in another aspect, provided herein is a composition comprising nepenthesin I, nepenthesin II, neprosin, a variant thereof, and/or a salt thereof. In some embodiments, the composition is a pharmaceutical composition. The compositions may be formulated into solid, semi-solid, or liquid forms, such as tablets, capsules, powders, granules, ointments, solutions, injections, gels, and microspheres. Administration of the composition can be achieved in various ways, for example, by oral administration.

In some embodiments, the pharmaceutical composition comprises a therapeutically effective amount of nepenthesin I, nepenthesin II, neprosin, variant thereof, or mixture thereof and a pharmaceutically acceptable carrier. In a particular embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, incorporated in its entirety by reference herein. Such compositions will contain a therapeutically effective amount of the enzyme(s), preferably in purified form, together with a suitable amount of carrier so as to provide the form for proper administration to the subject. The formulation should suit the mode of administration.

For oral administration, the pharmaceutical composition can be used alone or in combination with appropriate additives to make tablets, powders, granules, capsules, syrups, liquids, suspensions, etc. For example, solid oral forms of the composition can be prepared with conventional additives, disintegrators, lubricants, diluents, buffering agents, moistening agents, preservatives and flavoring agents. Non-limiting examples of excipients include lactose, mannitol, corn starch, potato starch, crystalline cellulose, cellulose derivatives, acacia, corn starch, sodium carboxymethylcellulose, talc, magnesium stearate, flavors and colors. In some embodiments, the formulation releases the enzyme(s) in the stomach of the subject so that the peptidic food antigen(s) can be degraded by the enzyme(s).

The composition can be lyophilized from an aqueous solution optionally in the presence of appropriate buffers (e.g. phosphate, citrate, histidine, imidazole buffers) and excipients (e.g. cryoprotectants such as sucrose, lactose, trehalose). Lyophilized cakes can optionally be blended with excipients and made into different forms.

In another aspect, provided are methods for treating gluten intolerance or an associated condition, such as celiac disease, wheat allergy, gluten sensitivity and dermatitis herpetiformis, in a patient in need thereof, comprising treating a food comprising gluten or suspected of comprising gluten with an effective amount of the composition prior to consumption by the patient. In some embodiments, the food is combined with an effective amount of the composition during its preparation. In one embodiment, the composition is added after any heating steps in the food preparation. In one embodiment, the composition is added before one or more heating steps in the food preparation.

Nepenthesin I, nepenthesin II, and neprosin occur as proenzymes in *Nepenthes* prior to activation. That is, the protein includes a propeptide that is cleaved in order to activate the enzyme in the pitcher fluid. In one embodiment, the composition comprises nepenthesin I, nepenthesin II, neprosin, a variant thereof, and/or a salt thereof comprising a propeptide. In one embodiment, the propeptide is adjacent to the N terminus of the enzyme. In one embodiment, the propeptide is the naturally-occurring propeptide for the enzyme. In one embodiment, the propeptide is a heterologous propeptide (e.g., from a different protein or species, or synthetic). In one embodiment, the propeptide is cleaved by acidic conditions. In one embodiment, the propeptide is cleaved by an enzyme. In one embodiment, the presence of the propeptide results in delayed activity of the enzyme in the stomach (e.g., due to the time required to remove the propeptide and produce the mature enzyme). In one embodiment, the propeptide is engineered to be removed more slowly in order to delay activity of the enzyme in the stomach. In one embodiment, the propeptide is engineered to be removed more quickly in order to speed up activity of the enzyme in the stomach.

In a preferred embodiment, the formulation is a controlled release formulation. The term "controlled release formulation" includes sustained release and time-release formulations. Controlled release formulations are well-known in the art. These include excipients that allow for sustained, periodic, pulse, or delayed release of the drug. Controlled release formulations include, without limitation, embedding of the drug into a matrix; enteric coatings; micro-encapsulation; gels and hydrogels; and any other formulation that allows for controlled release of a drug.

In some embodiments, the composition is administered as a food additive together with a food comprising or suspected of comprising a potentially antigenic food protein. In one embodiment, the food comprises or is suspected of comprising gluten, for example bread, pasta, cereal, and the like, made from wheat, rye and barley, etc.

In one embodiment, the enzyme(s) in the composition is activated upon contact with acid (i.e., in the stomach).

In some embodiments, the composition comprising neprosin, nepenthesin I, nepenthesin II, a variant thereof, or a combination thereof is admixed with food, or used to pre-treat foodstuffs containing glutens. The composition present in foods can be enzymatically active to reduce the level of gluten in the food prior to or during ingestion.

In some embodiments, the composition comprises from about 0.1% to about 99%, from about 0.5% to about 95%, from about 1% to about 95%, from about 5% to about 95%, from about 10% to about 90%, from about 20% to about 80%, from about 25% to about 75% of the enzyme(s). In some embodiments, the amount of enzyme in the composition is about 0.01%, about 0.1%, about 0.5%, about 1%, about 5%, about 10%, about 20%, about 25%, about 30%, about 35%, about 40%, about 45%, about 50%, about 55%, about 60%, about 65%, about 70%, about 75%, about 80%, about 85%, about 90%, or about 95% of the total composition or food product, or a range between any two of the values (including end points).

In some embodiments, the composition comprises neprosin and nepenthesin, or a variant thereof. In some embodiments, the nepenthesin is nepenthesin I and/or nepenthesin II, or a variant thereof. In some embodiments, the nepenthesin is recombinant nepenthesin I and/or recombinant nepenthesin II, or a variant thereof. In some embodiments, the nepenthesin is recombinant nepenthesin I and recombinant nepenthesin II, or a variant of each thereof. In some embodiments, the neprosin is recombinant neprosin, or a variant thereof. In a preferred embodiment, the composition comprises nepenthesin I, nepenthesin II, and/or neprosin comprising the amino acid sequence(s) of nepenthesin I, nepenthesin II, and/or neprosin from a *Nepenthes* species, or a variant(s) thereof.

Nepenthesin I mRNA/cDNA sequences have been described from several *Nepenthes* species, for example, *Nepenthes mirabilis* (GenBank Accession No. JX494401), *Nepenthes gracilis* (GenBank Accession No. AB114914), and *Nepenthes alata* (GenBank Accession No. AB2666803). Nepenthesin 11 mRNA/cDNA sequences have been described from several *Nepenthes* species, for example, *Nepenthes mirabilis* (GenBank Accession No. JX494402), and *Nepenthes gracilis* (GenBank Accession No. AB114915).

Nepenthesin I protein sequences have been described from several *Nepenthes* species, for example, *Nepenthes mirabilis* (GenBank Accession No. AFV26024; SEQ ID NO.: 5), *Nepenthes gracilis* (GenBank Accession No. BAD07474; SEQ ID NO.: 7), and *Nepenthes alata* (GenBank Accession No. BAF98915; SEQ ID NO.: 6). Nepenthesin II protein sequences have been described from several *Nepenthes* species, for example, *Nepenthes mirabilis* (GenBank Accession No. AFV26025; SEQ ID NO.: 8), and *Nepenthes gracilis* (GenBank Accession No. BAD07475; SEQ ID NO.: 9). The sequences are also found in U.S. Patent Application Publication No. 2014/0186330, which is incorporated herein by reference in its entirety.

Each of the sequences represented by the GenBank Accession Nos. provided herein are incorporated herein by reference in their entireties.

In some embodiments, the nepenthesin is a variant of nepenthesin having at least about 85% sequence homology to an amino acid sequence of nepenthesin I (e.g., SEQ ID NO.: 5; SEQ ID NO.: 6; SEQ ID NO.: 7; or SEQ ID NO.: 21). In some embodiments, the variant has at least about 90% sequence homology to an amino acid sequence of nepenthesin I. In some embodiments, the variant has at least about 95% sequence homology to an amino acid sequence of nepenthesin I. In some embodiments, the variant has at least about 96% sequence homology to an amino acid sequence of nepenthesin I. In some embodiments, the variant has at least about 97% sequence homology to an amino acid sequence of nepenthesin I. In some embodiments, the variant has at least about 98% sequence homology to an amino acid sequence of nepenthesin I. In some embodiments, the variant has at least about 99% sequence homology to an amino acid sequence of nepenthesin T. In one embodiment, the nepenthesin comprises the amino acid sequence of SEQ ID NO.: 5; SEQ ID NO.: 6; SEQ ID NO.: 7; or SEQ ID NO.: 21.

In some embodiments, the nepenthesin is a variant of nepenthesin having at least about 85% sequence homology to an amino acid sequence of nepenthesin II (e.g., SEQ ID NO.: 8; SEQ ID NO.: 9; or SEQ ID NO.: 22). In some embodiments, the variant has at least about 90% sequence homology to an amino acid sequence of nepenthesin II. In some embodiments, the variant has at least about 95% sequence homology to an amino acid sequence of nepenthesin II. In some embodiments, the variant has at least about 96% sequence homology to an amino acid sequence of nepenthesin II. In some embodiments, the variant has at least about 97% sequence homology to an amino acid sequence of nepenthesin II. In some embodiments, the variant has at least about 98% sequence homology to an amino acid sequence of nepenthesin II. In some embodiments, the variant has at least about 99% sequence homology to an amino acid sequence of nepenthesin II. In one embodiment, the nepenthesin comprises the amino acid sequence of SEQ ID NO.: 8; SEQ ID NO.: 9; or SEQ ID NO.: 22.

In one aspect of the invention, the ratio of neprosin to nepenthesin I and/or II in the composition is such that the peptidic food antigen is cleaved into sufficiently small and/or innocuous fragments so as to prevent gluten intolerance, celiac disease, wheat allergy, or dermatitis herpetiformis, inflammation, IEL proliferation or recruitment, intraepithelial lymphocytosis, and/or villous atrophy, or any symptom thereof, in an intestine of the subject.

In some embodiments, the neprosin:nepenthesin ratio is between about 1:100 to about 100:1. Preferably, the neprosin:nepenthesin ratio is between about 1:1 to about 1:10. Even more preferably, the neprosin:nepenthesin ratio is about 1:4.

In some embodiments, the composition comprises a ratio of neprosin to nepenthesin (nepenthesin I and/or II) of at least about 100:1. In some embodiments, the composition comprises a ratio of neprosin to nepenthesin of at least about 90:1. In some embodiments, the composition comprises a ratio of neprosin to nepenthesin of at least about 70:1. In some embodiments, the composition comprises a ratio of neprosin to nepenthesin of at least about 60:1. In some embodiments, the composition comprises a ratio of neprosin to nepenthesin of at least about 50:1. In some embodiments, the composition comprises a ratio of neprosin to nepenthesin of at least about 40:1. In some embodiments, the composition comprises a ratio of neprosin to nepenthesin of at least about 30:1. In some embodiments, the composition comprises a ratio of neprosin to nepenthesin of at least about 20:1. In some embodiments, the composition comprises a ratio of neprosin to nepenthesin of at least about 10:1. In some embodiments, the composition comprises a ratio of neprosin to nepenthesin of at least about 5:1. In some embodiments, the composition comprises a ratio of neprosin to nepenthesin of at least about 4:1. In some embodiments, the composition comprises a ratio of neprosin to nepenthesin of at least about 3:1. In some embodiments, the composition comprises a ratio of neprosin to nepenthesin of at least about 2:1. In some embodiments, the composition comprises a ratio of neprosin to nepenthesin of at least about 1:1. In some embodiments, the composition comprises a ratio of neprosin to nepenthesin of at least about 1:2. In some embodiments, the composition comprises a ratio of neprosin to nepenthesin of at least about 1:3. In some embodiments, the composition comprises a ratio of neprosin to nepenthesin of at least about 1:4. In some embodiments, the composition comprises a ratio of neprosin to nepenthesin of at least about 1:5. In some embodiments, the composition comprises a ratio of neprosin to nepenthesin of at least about 1:10. In some embodiments, the composition comprises a ratio of neprosin to nepenthesin of at least about 1:20. In some embodiments, the composition comprises a ratio of neprosin to nepenthesin of at least about 1:30. In some embodiments, the composition comprises a ratio of neprosin to nepenthesin of at least about 1:40. In some embodiments, the composition comprises a ratio of neprosin to nepenthesin of at least about 1:50. In some embodiments, the composition comprises a ratio of neprosin to nepenthesin of at least about 1:60. In some embodiments, the composition comprises a ratio of neprosin to nepenthesin of at least about 1:70. In some embodiments, the composition comprises a ratio of neprosin to nepenthesin of at least about 1:80. In some embodiments, the composition comprises a ratio of neprosin to nepenthesin of at least about 1:90. In some embodiments, the composition comprises a ratio of neprosin to nepenthesin of at least about 1:100.

In one aspect of the invention, the ratio of nepenthesin I to nepenthesin II in the composition is such that the peptidic food antigen is cleaved into sufficiently small and/or innocuous fragments so as to prevent inflammation, IEL proliferation or recruitment, intraepithelial lymphocytosis, and/or villous atrophy in an intestine of the subject. In some embodiments, the nepenthesin I:nepenthesin II ratio is between about 1:100 to about 100:1.

In some embodiments, the composition comprises a ratio of nepenthesin I to nepenthesin II of at least about 100:1. In some embodiments, the composition comprises a ratio of nepenthesin I to nepenthesin II of at least about 90:1. In some embodiments, the composition comprises a ratio of nepenthesin I to nepenthesin II of at least about 70:1. In some embodiments, the composition comprises a ratio of nepenthesin I to nepenthesin II of at least about 60:1. In some embodiments, the composition comprises a ratio of nepenthesin I to nepenthesin II of at least about 50:1. In some embodiments, the composition comprises a ratio of nepenthesin I to nepenthesin II of at least about 40:1. In some embodiments, the composition comprises a ratio of nepenthesin I to nepenthesin II of at least about 30:1. In some embodiments, the composition comprises a ratio of nepenthesin I to nepenthesin II of at least about 20:1. In some embodiments, the composition comprises a ratio of nepenthesin I to nepenthesin II of at least about 10:1. In some embodiments, the composition comprises a ratio of nepenthesin I to nepenthesin II of at least about 5:1. In some embodiments, the composition comprises a ratio of nepenthesin I to nepenthesin II of at least about 4:1. In some embodiments, the composition comprises a ratio of nepenthesin I to nepenthesin II of at least about 3:1. In some embodiments, the composition comprises a ratio of nepenthesin I to nepenthesin II of at least about 2:1. In some embodiments, the composition comprises a ratio of nepenthesin I to nepenthesin II of at least about 1:1. In some embodiments, the composition comprises a ratio of nepenthesin I to nepenthesin II of at least about 1:2. In some embodiments, the composition comprises a ratio of nepenthesin I to nepenthesin II of at least about 1:3. In some embodiments, the composition comprises a ratio of nepenthesin I to nepenthesin II of at least about 1:4. In some embodiments, the composition comprises a ratio of nepenthesin I to nepenthesin II of at least about 1:5. In some embodiments, the composition comprises a ratio of nepenthesin I to nepenthesin II of at least about 1:10. In some embodiments, the composition comprises a ratio of nepenthesin I to nepenthesin II of at least about 1:20. In some embodiments, the composition comprises a ratio of nepenthesin I to nepenthesin II of at least about 1:30. In some embodiments, the composition comprises a ratio of nepenthesin I to nepenthesin II of at least about 1:40. In some embodiments, the composition comprises a ratio of nepenthesin I to nepenthesin II of at least about 1:50. In some embodiments, the composition comprises a ratio of nepenthesin I to nepenthesin II of at least about 1:60. In some embodiments, the composition comprises a ratio of nepenthesin I to nepenthesin II of at least about 1:70. In some embodiments, the composition comprises a ratio of nepenthesin I to nepenthesin II of at least about 1:80. In some embodiments, the composition comprises a ratio of nepenthesin I to nepenthesin II of at least about 1:90. In some embodiments, the composition comprises a ratio of nepenthesin I to nepenthesin II of at least about 1:100.

In one aspect of the invention, the composition comprising one or more *Nepenthes* enzymes is administered to the subject at a ratio of about 2000:1 to about 1:1 substrate (e.g., total protein or gluten) to enzyme.

IV. Methods of Preparation

It is contemplated that nepenthesin and/or neprosin can be concentrated (or extracted) or purified by methods known in the art, for example (but not limited to) filtration or affinity purification based on immobilized pepstatin, from a natural source, including pitcher secretions of plants such as *Nepenthes*. Classical protein chromatography, such as size exclusion chromatography (also known as gel permeation chromatography) and/or chromatofocusing chromatography, may also be used to concentrate (or extract) or purify nepenthesin and/or neprosin. Chromatofocusing may be used prior to or after size exclusion. Nepenthesin I, nepenthesin II, and neprosin are found in relatively small quantity in natural plant secretions. Production of nepenthesin I, nepenthesin II, and/or neprosin can be increased, for example, using bioengineering technologies to create transgenic plants that express and/or secrete increased amounts of the desired enzyme(s), or a variant thereof.

Besides being isolated from a plant source, the *Nepenthes* enzyme or variant thereof may be prepared by chemical synthesis. Chemical synthesis can be achieved by coupling of the amino acids according to the sequence of the desired enzyme or variant. Various peptide coupling methods and commercial peptide synthetic apparatuses are available to synthesis peptide or proteins, for example, automated synthesizers by Applied Biosystems, Inc., Foster City, Calif., Beckman, and other manufacturers.

In another aspect, provided is a method of preparing *Nepenthes* enzyme or variant thereof using recombinant production systems by transforming or transfecting a cell with the DNA (e.g., cDNA) and/or messenger RNA of the enzyme(s) so that the cell is capable of producing the enzyme(s). For example, nepenthesin can be produced by establishing host-vector systems in organisms such as *Escherichia coli, Saccharomyces cerevisiae, Pichia pastoris, Lactobacillus*, Bacilli, Aspergilli, and plant cell cultures, such as tobacco cells, etc.

Vectors and host cells, such as *E. coli*, comprising polynucleotides and compositions containing any of the polynucleotides or polypeptides as described herein are also provided.

In another aspect, provided is a method for producing recombinant *Nepenthes* enzyme (nepenthesin I, nepenthesin II, and/or neprosin, or a variant thereof) comprising expressing in a chosen host organism a nucleic acid sequence which encodes said enzyme, and inserting the nucleic acid sequence into an appropriately designed vector. In one aspect, the recombinant enzyme is nepenthesin I or a variant thereof. In one aspect, the recombinant enzyme is nepenthesin II or a variant thereof. In one aspect, the recombinant enzyme is neprosin or a variant thereof. In one aspect, the recombinant enzyme is a mixture of nepenthesin I, nepenthesin II, and/or neprosin or variant thereof.

In another aspect, provided is a composition comprising recombinant nepenthesin such as nepenthesin I and/or nepenthesin II or a variant thereof. In one aspect, the recombinant nepenthesin is nepenthesin I or a variant thereof. In one aspect, the recombinant nepenthesin is nepenthesin II or a variant thereof. In one aspect, the recombinant nepenthesin is a mixture of nepenthesin I and nepenthesin II or variants thereof.

In one aspect, this invention relates to a cDNA as described herein. In one embodiment, this invention relates to a vector comprising a cDNA as described herein. In a preferred embodiment, the vector is an expression vector. In one embodiment, this invention relates to a cell expressing recombinant nepenthesin I, recombinant nepenthesin II, recombinant neprosin, a variant or mixture thereof.

In some embodiments, biosynthesis of *Nepenthes* enzyme(s) can be achieved by transforming a cell with a vector comprising a cDNA that encodes nepenthesin I, for example the nucleotide sequence of SEQ ID NO. 4, SEQ ID NO. 5, SEQ ID NO.: 6, GenBank Accession No. JX494401, GenBank Accession No. AB114914, or GenBank Accession No. AB266803. In some embodiments, biosynthesis of nepenthesin can be achieved by transforming a cell with a vector comprising a sequence homologous to a cDNA which encodes nepenthesin I, which sequence encodes a protein with protease activity. The sequence may have at least about 60% homology to a cDNA that encodes nepenthesin I. The sequence may have at least about 70% homology to a cDNA that encodes nepenthesin I. The sequence may have at least about 80% homology to a cDNA that encodes nepenthesin I. The sequence may have at least about 85% homology to a cDNA that encodes nepenthesin I. The sequence may have at least about 90% homology to a cDNA that encodes nepenthesin I. The sequence may have at least about 95% homology to a cDNA that encodes nepenthesin I. The sequence may have at least about 96% homology to a cDNA that encodes nepenthesin I. The sequence may have at least about 97% homology to a cDNA that encodes nepenthesin I. The sequence may have at least about 98% homology to a cDNA that encodes nepenthesin I. The sequence may have at least about 99% homology to a cDNA that encodes nepenthesin I. In a preferred embodiment, the sequence encodes a variant of nepenthesin I that retains glutenase activity. In a particularly preferred embodiment, the sequence encodes a variant of nepenthesin I that degrades at least one toxic gluten peptide.

In some embodiments, biosynthesis of *Nepenthes* enzyme(s) can be achieved by transforming a cell with a vector comprising a cDNA that encodes nepenthesin II, for example the nucleotide sequence of SEQ ID NO.: 8, SEQ ID NO.: 9, GenBank Accession No. JX494402 or GenBank Accession No. AB114915. In some embodiments, biosynthesis of nepenthesin can be achieved by transforming a cell with a vector comprising a sequence homologous to a cDNA which encodes nepenthesin II, which sequence encodes a protein with protease activity. The sequence may have at least about 60% homology to a cDNA that encodes nepenthesin II. The sequence may have at least about 70% homology to a cDNA that encodes nepenthesin II. The sequence may have at least about 80% homology to a cDNA that encodes nepenthesin II. The sequence may have at least about 85% homology to a cDNA that encodes nepenthesin II. The sequence may have at least about 90% homology to a cDNA that encodes nepenthesin II. The sequence may have at least about 95% homology to a cDNA that encodes nepenthesin II. The sequence may have at least about 96% homology to a cDNA that encodes nepenthesin II. The sequence may have at least about 97% homology to a cDNA that encodes nepenthesin II. The sequence may have at least about 98% homology to a cDNA that encodes nepenthesin II. The sequence may have at least about 99% homology to a cDNA that encodes nepenthesin II. In a preferred embodiment, the sequence encodes a variant of nepenthesin II that retains glutenase activity. In a particularly preferred embodiment, the sequence encodes a variant of nepenthesin II that degrades at least one toxic gluten peptide.

In some embodiments, biosynthesis of *Nepenthes* enzyme(s) can be achieved by transforming a cell with a vector comprising a cDNA that encodes neprosin, for example the nucleotide sequence of SEQ ID NO.: 2. In some embodiments, biosynthesis of neprosin can be achieved by transforming a cell with a vector comprising a sequence homologous to a cDNA which encodes neprosin, which sequence encodes a protein with protease activity. The sequence may have at least about 60% homology to a cDNA that encodes neprosin. The sequence may have at least about 70% homology to a cDNA that encodes neprosin. The sequence may have at least about 80% homology to a cDNA that encodes neprosin. The sequence may have at least about 85% homology to a cDNA that encodes neprosin. The sequence may have at least about 90% homology to a cDNA that encodes neprosin. The sequence may have at least about 95% homology to a cDNA that encodes neprosin. The sequence may have at least about 96% homology to a cDNA that encodes neprosin. The sequence may have at least about 97% homology to a cDNA that encodes neprosin. The sequence may have at least about 98% homology to a cDNA that encodes neprosin. The sequence may have at least about 99% homology to a cDNA that encodes neprosin. In a preferred embodiment, the sequence encodes a variant of neprosin that retains prolyl endoprotease activity. In an especially preferred embodiment, the sequence encodes a variant of neprosin that retains glutenase activity. In a particularly preferred embodiment, the sequence encodes a variant of neprosin that degrades at least one toxic gluten peptide.

Without being bound by theory, it is believed that inflammatory response to gluten in the intestines of affected individuals is due to the incomplete hydrolysis of gluten proteins, leading to the formation of toxic (immunotoxic) gluten peptides. Several immunotoxic and/or potentailly immunotoxic gluten peptides are known. These include, but are not limited to, the 33-mer (SEQ ID NO.: 15, LQLQPF(PQPQLPY)$_3$PQPQPF) and p31-49 (SEQ ID NO.: 16, LGQQQPFPPQQPYPQPQPF) from α-gliadin; Gly-156 (SEQ ID NO.: 17, QQQQPPFSQQQQSPFSQQQQ) from low molecular weight glutenin; and the nonapeptide repeat (SEQ ID NO.: 18, GYYPTSPQQ) and hexapeptide repeat (SEQ ID NO.: 19, PGQGQQ) from high molecular weight glutenin.

In some embodiments, nepenthesin I, nepenthesin II, neprosin and/or a variant thereof is synthesized by transfecting, infecting, or transforming a cell with one or more vectors comprising a cDNA sequence of each desired enzyme. That is, a single cell, cell line, or organism may be engineered so as to produce two or more enzymes. In some embodiments, the desired enzymes are synthesized by separate cells and combined in the pharmaceutical composition. In a preferred embodiment, the recombinant nepenthesin I, nepenthesin II, neprosin and/or a variant thereof is not glycosylated. In one embodiment, the recombinant nepenthesin I, nepenthesin II, neprosin and/or a variant thereof has a different glycosylation pattern than the natural enzyme (i.e., nepenthesin I, nepenthesin II, or neprosin isolated from a *Nepenthes* plant).

The synthetic (e.g., recombinant) *Nepenthes* enzyme(s) can be concentrated or purified according to known methods, such as those for isolating *Nepenthes* enzyme(s) from the plant pitcher liquid.

In some embodiments, the protein product isolated from a natural source or a synthetic (e.g., recombinant) source comprises at least 20% by weight of at least one *Nepenthes* enzyme or a variant thereof. In some embodiments, the isolated protein product comprises at least about 50%, about 75%, about 90%, about 95% by weight of the *Nepenthes* enzyme or variant thereof. In some embodiments, the isolated protein product comprises at least 99% by weight of the *Nepenthes* enzyme or variant thereof.

In some embodiments, the recombinant *Nepenthes* enzyme or variant thereof comprises substantially only recombinant nepenthesin or variant thereof. In some embodiments, the recombinant nepenthesin or variant thereof comprises substantially only recombinant nepenthesin I or variant thereof. In some embodiments, the recombinant nepenthesin or variant thereof comprises substantially only nepenthesin II or variant thereof. In some embodiments, the recombinant nepenthesin or variant thereof comprises nepenthesin I and nepenthesin H, or variant thereof. In some embodiments, the recombinant nepenthesin or variant thereof comprises a ratio of nepenthesin I to nepenthesin II (or variant of each thereof) of at least about 100:1. In some embodiments, the recombinant nepenthesin comprises a ratio of nepenthesin I to nepenthesin II of at least about 90:1. In some embodiments, the recombinant nepenthesin comprises a ratio of nepenthesin I to nepenthesin II of at least about 70:1. In some embodiments, the recombinant nepenthesin comprises a ratio of nepenthesin I to nepenthesin II of at least about 60:1. In some embodiments, the recombinant nepenthesin comprises a ratio of nepenthesin I to nepenthesin II of at least about 50:1. In some embodiments, the recombinant nepenthesin comprises a ratio of nepenthesin I to nepenthesin II of at least about 40:1. In some embodiments, the recombinant nepenthesin comprises a ratio of nepenthesin I to nepenthesin II of at least about 30:1. In some embodiments, the recombinant nepenthesin comprises a ratio of nepenthesin I to nepenthesin II of at least about 20:1. In some embodiments, the recombinant nepenthesin comprises a ratio of nepenthesin I to nepenthesin II of at least about 10:1. In some embodiments, the recombinant nepenthesin comprises a ratio of nepenthesin I to nepenthesin II of at least about 5:1. In some embodiments, the recombinant nepenthesin comprises a ratio of nepenthesin I to nepenthesin II of at least about 4:1. In some embodiments, the recombinant nepenthesin comprises a ratio of nepenthesin I to nepenthesin II of at least about 3:1. In some embodiments, the recombinant nepenthesin comprises a ratio of nepenthesin I to nepenthesin II of at least about 2:1. In some embodiments, the recombinant nepenthesin comprises a ratio of nepenthesin I to nepenthesin II of at least about 1:1. In some embodiments, the recombinant nepenthesin comprises a ratio of nepenthesin I to nepenthesin II of at least about 1:2. In some embodiments, the recombinant nepenthesin comprises a ratio of nepenthesin I to nepenthesin II of at least about 1:3. In some embodiments, the recombinant nepenthesin comprises a ratio of nepenthesin I to nepenthesin II of at least about 1:4. In some embodiments, the recombinant nepenthesin comprises a ratio of nepenthesin I to nepenthesin II of at least about 1:5. In some embodiments, the recombinant nepenthesin comprises a ratio of nepenthesin I to nepenthesin II of at least about 1:10. In some embodiments, the recombinant nepenthesin comprises a ratio of nepenthesin I to nepenthesin II of at least about 1:20. In some embodiments, the recombinant nepenthesin comprises a ratio of nepenthesin I to nepenthesin II of at least about 1:30. In some embodiments, the recombinant nepenthesin comprises a ratio of nepenthesin I to nepenthesin II of at least about 1:40. In some embodiments, the recombinant nepenthesin comprises a ratio of nepenthesin I to nepenthesin II of at least about 1:50. In some embodiments, the recombinant nepenthesin comprises a ratio of nepenthesin I to nepenthesin II of at least about 1:60. In some embodiments, the recombinant nepenthesin comprises a ratio of nepenthesin I to nepenthesin II of at least about 1:70. In some embodiments, the recombinant nepenthesin comprises a ratio of nepenthesin I to nepenthesin II of at least about 1:80. In some embodiments, recombinant nepenthesin comprises a ratio of nepenthesin I to nepenthesin II of at least about 1:90. In some embodiments, the recombinant nepenthesin comprises a ratio of nepenthesin I to nepenthesin II of at least about 1:100.

In some embodiments, the recombinant *Nepenthes* enzyme or variant thereof comprises substantially only recombinant neprosin or variant thereof. In some embodiments, the recombinant *Nepenthes* enzyme or variant thereof comprises neprosin and nepenthesin or variant thereof. In some embodiments, the recombinant *Nepenthes* enzyme or variant thereof comprises neprosin and nepenthesin I or variant thereof. In some embodiments, the recombinant *Nepenthes* enzyme or variant thereof comprises neprosin and nepenthesin II or variant thereof. In some embodiments, the recombinant *Nepenthes* enzyme or variant thereof comprises neprosin, nepenthesin I and nepenthesin II, or variant thereof. In some embodiments, the recombinant *Nepenthes* enzyme or variant thereof comprises a ratio of neprosin to nepenthesin (or variant of each thereof) of at least about 100:1. In some embodiments, the recombinant *Nepenthes* enzyme comprises a ratio of neprosin to nepenthesin of at least about 90:1. In some embodiments, the recombinant *Nepenthes* enzyme comprises a ratio of neprosin to nepenthesin of at least about 70:1. In some embodiments, the recombinant *Nepenthes* enzyme comprises a ratio of neprosin to nepenthesin of at least about 60:1. In some embodiments, the recombinant *Nepenthes* enzyme comprises a ratio of neprosin to nepenthesin of at least about 50:1. In some embodiments, the recombinant *Nepenthes* enzyme comprises a ratio of neprosin to nepenthesin of at least about 40:1. In some embodiments, the recombinant *Nepenthes* enzyme comprises a ratio of neprosin to nepenthesin of at least about 30:1. In some embodiments, the recombinant *Nepenthes* enzyme comprises a ratio of neprosin to nepenthesin of at least about 20:1. In some embodiments, the recombinant *Nepenthes* enzyme comprises a ratio of neprosin to nepenthesin of at least about 10:1. In some embodiments, the recombinant *Nepenthes* enzyme comprises a ratio of neprosin to nepenthesin of at least about 5:1. In some embodiments, the recombinant *Nepenthes* enzyme comprises a ratio of neprosin to nepenthesin of at least about 4:1. In some embodiments, the recombinant *Nepenthes* enzyme comprises a ratio of neprosin to nepenthesin of at least about 3:1. In some embodiments, the recombinant *Nepenthes* enzyme comprises a ratio of neprosin to nepenthesin of at least about 2:1. In some embodiments, the recombinant *Nepenthes* enzyme comprises a ratio of neprosin to nepenthesin of at least about 1:1. In some embodiments, the recombinant *Nepenthes* enzyme comprises a ratio of neprosin to nepenthesin of at least about 1:2. In some embodiments, the recombinant *Nepenthes* enzyme comprises a ratio of neprosin to nepenthesin of at least about 1:3. In some embodiments, the recombinant *Nepenthes* enzyme comprises a ratio of neprosin to nepenthesin of at least about 1:4. In some embodiments, the recombinant *Nepenthes* enzyme comprises a ratio of neprosin to nepenthesin of at least about 1:5. In some embodiments, the recombinant *Nepenthes* enzyme comprises a ratio of neprosin to nepenthesin of at least about 1:10. In some embodiments, the recombinant *Nepenthes* enzyme comprises a ratio of neprosin to nepenthesin of at least about 1:20. In some embodiments, the recombinant *Nepenthes* enzyme comprises a ratio of neprosin to nepenthesin of at least about 1:30. In some embodiments, the recombinant *Nepenthes* enzyme comprises a ratio of neprosin to nepenthesin of at least about 1:40. In some embodiments, the recombinant *Nepenthes* enzyme comprises a ratio of neprosin to nepenthesin of at least about 1:50. In some embodiments, the recombinant *Nepenthes* enzyme comprises a ratio of neprosin to nepenthesin of at least about 1:60. In some embodiments, the recombinant *Nepenthes* enzyme comprises a ratio of neprosin to nepenthesin of at least about 1:70. In some embodiments, the recombinant *Nepenthes* enzyme comprises a ratio of neprosin to nepenthesin of at least about 1:80. In some embodiments, recombinant *Nepenthes* enzyme comprises a ratio of neprosin to nepenthesin of at least about 1:90. In some embodiments, the recombinant *Nepenthes* enzyme comprises a ratio of neprosin to nepenthesin of at least about 1:100.

In some embodiments, the protein product isolated from a natural source or a synthetic source comprises an amino acid that is at least about 70% homologous to the amino acid sequence of *Nepenthes* nepenthesin I (e.g., SEQ ID NO.: 5; SEQ ID NO.: 6; SEQ ID NO.: 7; SEQ ID NO.: 21). In one embodiment, the protein product retains protease activity. The protein may be at least about 80% homologous to *Nepenthes* nepenthesin I. The protein may be at least about 85% homologous to *Nepenthes* nepenthesin I. The protein may be at least about 90% homologous to *Nepenthes* nepenthesin I. The protein may be at least about 95% homologous to *Nepenthes* nepenthesin I. The protein may be at least about 96% homologous to *Nepenthes* nepenthesin I. The protein may be at least about 97% homologous to *Nepenthes* nepenthesin I. The protein may be at least about 98% homologous to *Nepenthes* nepenthesin I. The protein may be at least about 99% homologous to *Nepenthes* nepenthesin I.

In some embodiments, the protein product isolated from a natural source or a synthetic source comprises a protein that is at least about 70% homologous to *Nepenthes* nepenthesin II (e.g., SEQ ID NO.: 8; SEQ ID NO.: 9; SEQ ID NO.: 20). In one embodiment, the protein product retains protease activity. The protein may be at least about 80% homologous to *Nepenthes* nepenthesin II. The protein may be at least about 85% homologous to *Nepenthes* nepenthesin II. The protein may be at least about 90% homologous to *Nepenthes* nepenthesin II. The protein may be at least about 95% homologous to *Nepenthes* nepenthesin II. The protein may be at least about 96% homologous to *Nepenthes* nepenthesin II. The protein may be at least about 97% homologous to *Nepenthes* nepenthesin II. The protein may be at least about 98% homologous to *Nepenthes* nepenthesin II. The protein may be at least about 99% homologous to *Nepenthes* nepenthesin II.

In some embodiments, the protein product isolated from a natural source or a synthetic source comprises a protein that is at least about 70% homologous to *Nepenthes* neprosin (e.g., SEQ ID NO.: 1). In one embodiment, the protein product retains protease activity. The protein may be at least about 80% homologous to *Nepenthes* neprosin. The protein may be at least about 85% homologous to *Nepenthes* neprosin. The protein may be at least about 90% homologous to *Nepenthes* neprosin. The protein may be at least about 95% homologous to *Nepenthes* neprosin. The protein may be at least about 96% homologous to *Nepenthes* neprosin. The protein may be at least about 97% homologous to *Nepenthes* neprosin. The protein may be at least about 98% homologous to *Nepenthes* neprosin. The protein may be at least about 99% homologous to *Nepenthes* neprosin.

In some embodiments, the protein product isolated from a natural source or a synthetic source comprises nepenthesin or a variant thereof with at least about 10% of the original protease activity of *Nepenthes* nepenthesin I. In some embodiments, the protein product comprises nepenthesin or a variant thereof with at least about 20% of the original protease activity of nepenthesin I. In some embodiments, the protein product comprises nepenthesin or a variant thereof with at least about 30% of the original protease activity of nepenthesin I. In some embodiments, the protein product comprises nepenthesin or a variant thereof with at least about 40% of the original protease activity of nepenthesin I. In some embodiments, the protein product comprises nepenthesin or a variant thereof with at least about 50% of the original protease activity of nepenthesin I. In some embodiments, the protein product comprises nepenthesin or a variant thereof with at least about 60% of the original protease activity of nepenthesin I. In some embodiments, the protein product comprises nepenthesin or a variant thereof with at least about 70% of the original protease activity of nepenthesin I. In some embodiments, the protein product comprises nepenthesin or a variant thereof with at least about 80% of the original protease activity of nepenthesin I. In some embodiments, the protein product comprises nepenthesin or a variant thereof with at least about 90% of the original protease activity of nepenthesin I. In some embodiments, the protein product comprises nepenthesin or a variant thereof with greater than about 100% of the original protease activity of nepenthesin I.

In some embodiments, the protein product isolated from a natural source or a synthetic source comprises nepenthesin or a variant thereof with at least about 10% of the original protease activity of *Nepenthes* nepenthesin II. In some embodiments, the protein product comprises nepenthesin or a variant thereof with at least about 20% of the original protease activity of nepenthesin II. In some embodiments, the protein product comprises nepenthesin or a variant thereof with at least about 30% of the original protease activity of nepenthesin II. In some embodiments, the protein product comprises nepenthesin or a variant thereof with at least about 40% of the original protease activity of nepenthesin II. In some embodiments, the protein product comprises nepenthesin or a variant thereof with at least about 50% of the original protease activity of nepenthesin II. In some embodiments, the protein product comprises nepenthesin or a variant thereof with at least about 60% of the original protease activity of nepenthesin II. In some embodiments, the protein product comprises nepenthesin or a variant thereof with at least about 70% of the original protease activity of nepenthesin II. In some embodiments, the protein product comprises nepenthesin or a variant thereof with at least about 80% of the original protease activity of nepenthesin II. In some embodiments, the protein product comprises nepenthesin or a variant thereof with at least about 90% of the original protease activity of nepenthesin II. In some embodiments, the protein product comprises nepenthesin or a variant thereof with greater than about 100% of the original protease activity of nepenthesin II.

In some embodiments, the protein product isolated from a natural source or a synthetic source comprises neprosin or a variant thereof with at least about 10% of the original protease activity of *Nepenthes* neprosin. In some embodiments, the protein product comprises neprosin or a variant thereof with at least about 20% of the original protease activity of neprosin. In some embodiments, the protein product comprises neprosin or a variant thereof with at least about 30% of the original protease activity of neprosin. In some embodiments, the protein product comprises neprosin or a variant thereof with at least about 40% of the original protease activity of neprosin. In some embodiments, the protein product comprises neprosin or a variant thereof with at least about 50% of the original protease activity of neprosin. In some embodiments, the protein product comprises neprosin or a variant thereof with at least about 60% of the original protease activity of neprosin. In some embodiments, the protein product comprises neprosin or a variant thereof with at least about 70% of the original protease activity of neprosin. In some embodiments, the protein product comprises neprosin or a variant thereof with at least about 80% of the original protease activity of neprosin. In some embodiments, the protein product comprises neprosin or a variant thereof with at least about 90% of the original protease activity of neprosin. In some embodiments, the protein product comprises neprosin or a variant thereof with greater than about 100% of the original protease activity of neprosin.

Unless stated otherwise, the abbreviations used throughout the specification have the following meanings:
g=gram
kDa=kiloDalton
kg=kilogram
L=liter
LC=liquid chromatography
mg=milligram
min=minute
mL=milliliter
mM=millimolar
MS=mass spectrometry nM=nanomolar
pM=picomolar
s.d.=standard deviation
µCi=microcurie
µg microgram
µL—microliter
µM=micromolar
µm=micrometer
° C.=degree Celsius These one-letter symbols have the following meaning when representing amino acids:

A=Alanine
R=Arginine
N=Asparagine
D=Aspartic acid
C=Cysteine
E=Glutamic acid
Q=Glutamine
G=Glycine
H=Histidine
I=Isoleucine
L=Leucine
K=Lysine
M=Methionine
F=Phenylalanine
P=Proline
S=Serine
T=Threonine
W=Tryptophan
Y=Tyrosine
V=Valine

EXAMPLES

Example 1: Horticulture and Production of Nepenthes Fluid

N. ventrata (100 plantings in 8" pots) were grown in a dedicated greenhouse (Urban Bog, Langley, BC, Canada). The plants were potted with wood bark, perlite, peat moss and humus mix (40, 35, 10, 5% respectively) and grown under natural lighting, with controlled humidity and temperature. Irrigation was applied at the soil level, to avoid addition of water to the pitchers. The pitchers were fed with frozen Drosophilae, 1 or 2 in every pitcher (approximately 1000 pitchers), although insects were also harvested from the environments (e.g. wasps). Fluid was harvested the following week by pipette, and the cycle repeated until 5 liters of fluid was collected. Crude pitcher fluid was clarified using a 0.22 m filter and the protein fraction concentrated 10× using an Amicon 10 kDa cut-off spin filter (Millipore), and washed 3× with 100 mM glycine-HCl (pH 2.5, active conditions) to remove any peptides resulting from self-digestion or residual prey digestion.

Example 2: Characterization of Nepenthes Fluid

For pH profiling, proteolytic activity was measured using a modified version of the hemoglobin activity assay. The assay consisted of 4 µL concentrated Nepenthes fluid mixed with 1.25 mg equine hemoglobin (Sigma Aldrich) to a final volume of 100 µL in an appropriate buffer. Protein was digested for 30 minutes at 37° C., 200 rpm, and quenched with 10% TCA. The precipitate was removed by centrifugation (14000 g, 10 minutes) and the supernatant used to measure the absorbance of soluble peptides at 280 nm (GE Nanovue plus spectrophotometer). All data points are the means of three technical and three biological replicates.

For enzyme inhibition testing, bovine serum albumin (1 mg/ml) was digested with 0.12 µM Nepenthes enzymes for 15 min at 37° C., quenched by brief boiling and then analyzed by 10% SDS-PAGE. The enzymes were pretreated with controls and inhibitors at 4° C. for 2 days prior to digestion experiments. PMSF, pepstatin, leupeptin, EDTA, EGTA, DTT from Sigma-Aldrich, and ZPP (Z-Pro-Pro-aldehyde-dimethyl acetal) from Bachem.

Figure 1B:
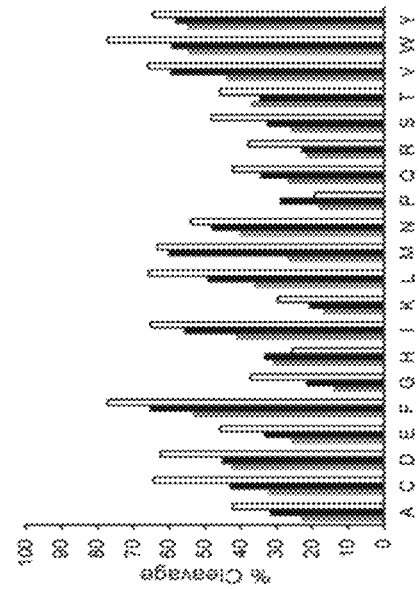
FIG. 1B shows N-terminal cleavage preferences (P1' position) as a function of storage time at elevated temperature. Data were generated and collected as described for FIG. 1A. No alteration of the broadly non-specific digestion character of the extract is observed over time.
Figure 1C:
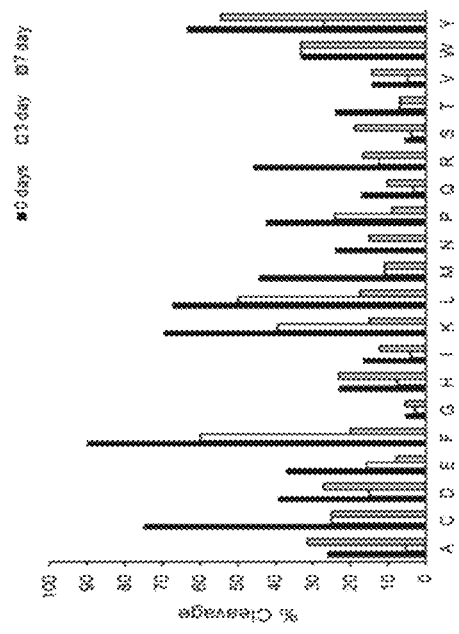
FIG. 1C shows the cleavage preferences of recombinant nepenthesin I and II compared to *Nepenthes* fluid protein concentrate in the P1 position. Data are shown as relative % cleavage to the total, as defined above, using LC-MS/MS data from a set of protein standards. Samples were digested in solution for 5 minutes at 37° C. in this comparison, for all three enzyme preparations. The absence of C-terminal proline (P) cleavage represents the major difference between recombinant enzymes and the fluid protein concentrate.
Figure 1D:
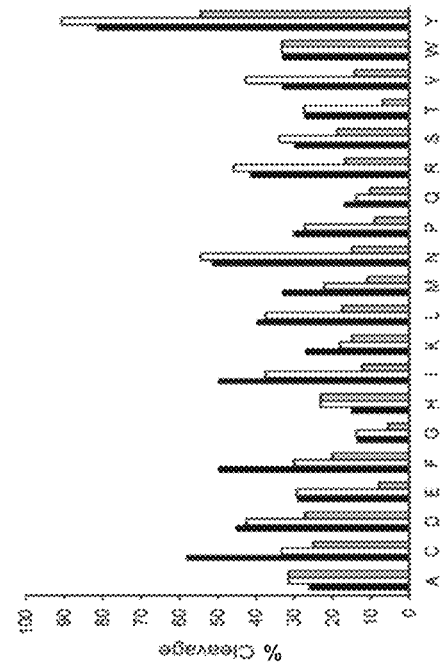
FIG. 1D shows the cleavage preferences of recombinant nepenthesin I and II compared to *Nepenthes* fluid protein concentrate in the P1' position. Data are provided as described for FIG. 1C.

Results:

The concentrated fraction possessed high proteolytic activity against soluble protein standards (FIGS. 1A-1D) and remained stable for weeks at 4° C., and under freeze/thaw cycles. Using a classical hemoglobin assay for digestion, the fluid concentrate exhibited maximum activity at pH 2.5 and retained activity up to pH 5 (FIG. 2A), encompassing a typical pH range for the human stomach. The pH profile exhibited some similarity to pepsin, but digestion could not be solely attributed to the aspartic protease components known to be present in the fluid (FIGS. 1A, 1B and 2B). Pepstatin, an aspartic protease inhibitor, could only partially suppress enzyme activity. However, no other inhibitors had an effect under these conditions. A slurry of crude wheat gliadin was prepared and the protein fraction of the fluid added; the protein fraction of the fluid rapidly clarified the slurry at pH 2.5 (FIG. 2C).

The protein extract contained a plant sub-proteome of limited complexity that remained stable in the presence of pepsin (FIG. 2D).

Example 3: Fractionation of Nepenthes Fluid

Two proteolytic components were isolated. Activity was retested against a 33mer from α-gliadin using MALDI-TOF. Fractions were also analyzed for protein content using MALDI-TOF (sinapinic acid as matrix), highlighting a single peak at 29 kDa. Fractions enriched in non-specific cleavage properties were further purified using gel filtration and retested for purity and for activity against 33mer.

Fluid protein concentrate was exchanged into 50 mM glycine and subjected to column chromatofocusing with fractionation. Fractions were analyzed for activity using MALDI-TOF (Sciex 5800 TOF/TOF, α-cyano-4-hydroxycinnamic acid as matrix). To test for activity, protein substrates were incubated with aliquots of column fractions at room temperature for 20 minutes and the digests analyzed by MALDI-TOF. Fractions enriched in proline cleavage were manually purified by reversed phase chromatography on Protein MacroTraps (Optimize Technologies). Enzyme was eluted and confirmed active against protein substrates.

Figure 3A:
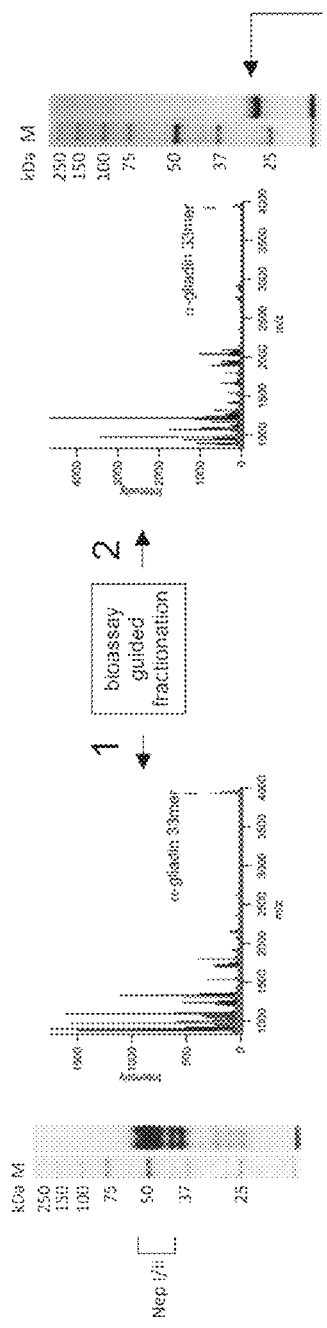
FIG. 3A shows the results from isolation of the two fractions from the activated fluid extract with proteolytic properties. Left: Silver-stain SDS-PAGE of fraction 1 containing nepenthesin, and MALDI spectrum of 33mer peptide processed with fraction 1. Right: Silver-stain SDS-PAGE of fraction 2 containing an unknown enzyme, and MALDI spectrum of 33mer peptides processed with fraction 2. MALDI of undigested 33mer in red, digested 33mer in black.

Results:

Each fraction was able to digest LQLQPFPQPQLPYPQPQLPYPQPQLPYPQPQPF (SEQ ID NO: 22), a 33mer peptide derived from α-gliadin that spans six overlapping T-cell epitopes and stimulates a potent T-cell response in celiac patients (FIG. 3A). This peptide sequence is highly resistant to digestion by gastric pepsin, even with prolonged periods, which was confirmed using a control digestion (data not shown).

Example 4: Identification of Nepenthes Proteins

Fluid concentrate and column fractions were analyzed using gel-free and gel-based proteomics methods. For gel free methods, proteins were reduced with DTT and alkylated with iodoacetamide using standard methods. Denatured samples were digested overnight with trypsin or for 1 hour with concentrated *Nepenthes* fluid. The digests solutions were lyophilized and resuspended in 1% formic acid (FA) prior to injection in the mass spectrometer for data-dependent LC-MS/MS analyses. For protein deglycosylation, sample was treated with PNGase F (New England Biolabs) following the manufacturer's method, prior to tryptic digestion. For gel-based proteomics analysis of fluid fractions, protein was separated by SDS-PAGE, and bands selected for in-gel tryptic digestion and data-dependent LC-MS/MS of the products. After washing, reduction and alkylation, the gel pieces were incubated overnight with trypsin, then extracted for mass analysis.

Protein digests were separated using an LC system (Easy-nLC 1000, Thermo Scientific) operating in a nanoflow configuration. Peptides were selected in a top-10 data-dependent experiment for collision-induced dissociation (CID) on a Thermo Orbitrap Velos ETD mass spectrometer in a high/low configuration (MS: Orbitrap at 60,000 resolution and MS/MS: ion trap). The data were searched using Mascot v2.3 (Matrix Sciences) against the NCBI Viriplanrtae (green plants), *Drosophila* and Bacteria/eubacterial databases, using conventional settings for tryptic digestion. For fluid-based digestions, the searches were configured using "no enzyme" specificity and other settings remained the same. For the identification of neprosin, peptides generated using the fluid extract were sequenced de novo, with the assistance of PEAKS software v7.1, producing a 4 kDa sequence with an accuracy >90%, and searched against the *Nepenthes* transcriptome (see below).

Results:

The digestion of the gliadin 33mer by fraction 1 appears to be due to the action of the aspartic protease in the fluid. Nepenthesins I and II have non-canonical cleavage properties for aspartic proteases. Using proteomics techniques and searching available databases, the presence of nepenthesin I in the protein extract was confirmed (Tables 1 and 2). Conventional bottom-up proteomics methods, based on tryptic digestion, were likely not ideal for the fluid. A sequence analysis of nepenthesin I showed only one tryptic cleavage site, suggesting that other components might similarly be difficult to identify with this approach. Trypsin was replaced in the standard proteomic workflow with active fluid protease, and confirmed the presence of nepenthesin II in the fluid as well (Supplementary Table 3). Purified fraction 1 analyzed in the same fashion identified only nepenthesin II.

TABLE 1

Gel-free bottom-up proteome analysis of *Nepenthes* pitcher fluid, digested with trypsin.

| Rank | accession number | Protein name | Taxonomy | # of peptides* |
|---|---|---|---|---|
| 1 | gi\|38325811 | Heat-shock protein 70-1 | N. tabacum | 5 (47) |
| 2 | gi\|326499079 | predicted protein | H. vulgare | 8 (49) |
| 3 | gi\|61214233 | nepenthesin-1 | N. gracilis | 1 (36) |
| 4 | gi\|326492680 | predicted protein | H. vulgare | 6 (52) |
| 5 | gi\|308044587 | Uncharacterized protein LOC100501669 | Zea Mays | 4 (26) |
| 6 | gi\|226532205 | Uncharacterized protein LOC100274495 | Zea Mays | 2 (19) |
| 7 | gi\|226510502 | Uncharacterized protein LOC100273100 | Zea Mays | 8 (38) |
| 8 | gi\|326502504 | Predicted protein | H. vulgare | 2 (18) |
| 9 | gi\|226507094 | Uncharacterized protein LOC100273141 | Zea Mays | 2 (15) |
| 10 | gi\|326502344 | Predicted protein | H. vulgare | 1 (8) |

*The total number of unique peptides identified (total number of peptides in brackets). Ion cut-off score (p < 0.05): 40

TABLE 2

Gel-free bottom-up proteome analysis of deglycosylated *Nepenthes* pitcher fluid, digested with trypsin.

| Rank | accession number | Protein name | Taxonomy | # of peptides* |
|---|---|---|---|---|
| 1 | gi\|165292442 | class IV chitinase | N. alata | 4 (26) |
| 2 | gi\|85682819 | thaumatin-like protein | N. gracilis | 2 (20) |
| 3 | gi\|61214233 | Nepenthesin-1 | N. gracilis | 1 (31) |
| 4 | gi\|393387669 | β-1,3-glucanase | N. alata | 3 (28) |
| 5 | gi\|167998797 | Predicted protein | P. pattens | 1 (7) |
| 6 | gi\|294461233 | unknown | Picea sitchensis | 1 (41) |
| 7 | gi\|413924608 | Hypothetical protein | Zea Mays | 1 (96) |
| 8 | gi\|527192719 | Hypothetical protein | Genlisea aurea | 1 (69) |
| 9 | gi\|205830697 | Unknown protein 18 | P. menziesii | 1 (2) |
| 10 | gi\|2493495 | Serine-carboxypeptidase | Pisum sativum | 1 (6) |

*The total number of unique peptides identified (total number of peptides in brackets). Ion cut-off score (p < 0.05): 39

TABLE 3

Gel-free bottom-up proteome analysis of *Nepenthes* pitcher fluid, digested with active *Nepenthes* pitcher fluid.

| Rank | accession number | Protein name | Taxonomy | # of peptides* |
|---|---|---|---|---|
| 1 | gi\|409179880 | Nepenthesin II | Nepenthes mirabilis | 40 (143) |
| 2 | gi\|61214233 | Nepenthesin I | Nepenthes gracilis | 16 (57) |
| 3 | gi\|218201535 | Hypothetical protein | Oryza sativa | 1 (1) |
| 4 | gi\|508715246 | ARM repeat superfamily protein | Theobroma cacao | 1 (1) |
| 5 | gi\|502179750 | Predicted, uncharacterized protein | Cicer arietinum | 1 (1) |
| 6 | gi\|502146217 | Predicted, acid phosphatase-like protein | Cicer arietinum | 1 (1) |
| 7 | gi\|255549692 | Hypothetical protein | Ricinus communis | 1 (1) |

*The total number of unique peptides identified (total number of peptides in brackets) Ion cut-off score (p < 0.05): 60

Example 5: *Nepenthes* Transcriptome Sequencing

Analysis of fraction 2 using a trypsin or active fluid digestion strategy resulted in no hits. Given that a sequenced genome for *Nepenthes* is unavailable, a different strategy was implemented to identify what appeared to be a proline-active enzyme. Gel analysis of the fraction suggests a simple composition (FIG. 3A), so whole-transcriptome shotgun sequencing was combined with de novo sequencing of peptides that were generated by the non-specific digestion of the protein fraction.

*N. ampullaria* were lab-grown in a small terrarium, in a 15-9 h light-dark photoperiod. On pitcher maturity, the plants were fed with 1 or 2 *Drosophila* per pitcher 24 hours before RNA extraction. For RNA extraction, the digestive fluid was removed and the pitchers washed with deionized water to remove partially digested material and other debris. The bottom one-third of the pitcher containing the secretory cells was excised, frozen in liquid nitrogen, and ground to a fine powder under liquid nitrogen. The total RNA extracted using a modified CTAB protocol.

SOLiD sequencing of the *N. ampullaria* transcriptome was performed by the University of Calgary Genomics Facility (Calgary, AB). Poly(A) RNA were enriched from 10 µg of total RNA using a Micro Purification Kit (Dynabeads mRNA DIRECT, Life Technologies), following the manufacturer's protocol. Whole transcriptome RNA libraries were prepared from polyA-captured RNA using the SOLID Total RNA-Seq kit (Life Technologies), following the manufacturer's protocol. The cDNA library was sequenced on an ABI SOLID 5500 sequencer (Life Technologies) using paired-end 75+35 bp runs. For analysis, raw sequencing data was converted to csFastq using SOLiD's XSQ_Tools and local Perl scripts. Cleaning filters were applied to data files, based on FastQC quality control statistics, and SOLiD sequencing adaptors detected with Cutadapt. Reads were clipped using TrimmomaticPE at a threshold of Phred 20, with a sliding window of 4, and returning clipped sequences at a minimum length of 25 bp. Only those cases were kept where both forward and reverse reads were retained. These cleaned read pairs were converted to pseudo-base space for assembly. De novo transcript assembly at various k-mers was performed with Velvet (version 1.2.10) and Oasis (version 0.2.8), compiled for colorspace. A final k-mer of 39 was used to assemble the combined forward read set of all sequence lanes in a single end assembly. Searching for the sequence tags generated by de novo MS/MS required the transformation of the assemblies into basespace. This was performed using utilities in SOLiD's denovo2 pipeline package and local perl scripts, tBlastn was used to identify a partial contig of 628 bp that best matched the query. To determine the sequence upstream and downstream of the hit, the following primers were used: GATTACGCCAAGCTT-CATTCCCGTTGGGATCTACGCATTG (LSO2R; SEQ ID NO.: 23) and ACGACAACTCAGATGGGAAGCGG (LSO7F; SEQ ID NO.: 24) for 5' and 3' RACE respectively (synthesized by the University of Calgary Core DNA Services). 5' and 3' RACE were performed using the SMARTer RACE 5'/3' kit (Clonetech, Mountain View, Calif.) following the manufacturer's protocol. Briefly, first strand cDNA was reverse synthesized using the manufacturer's modified oligo (dT) and/or SMARTer II A oligonucleotide primers. 5' and 3' RACE PCR were amplified with Phusion high-fidelity DNA polymerase (New England BioLabs) using the SMARTer universal primer paired with the specific primers (LSO2R or LSO7R). The PCR involved 30 cycles of denaturing at 98° C. for 30 seconds, annealing at 62° C. for 30 seconds and extension at 72° C. for 90 seconds. The 1 kb 5' RACE and 500 bp 3' RACE PCR products were gel-purified, and sequenced by the University of Calgary Core DNA Services. 5' and 3' RACE were repeated on cDNA from *N. ventrata* and *N. rafflesiana* and found Npr1 sequences that were 97% identical (not shown).

Figure 3B:
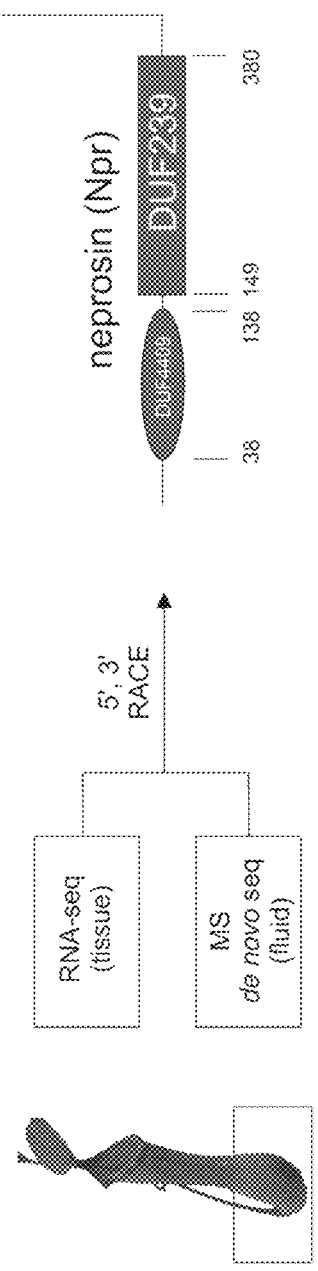
FIG. 3B shows the sequence identification strategy identifying fraction 2 enzyme as a two-domain construct, assigned the name neprosin in this study.
Figure 4A:
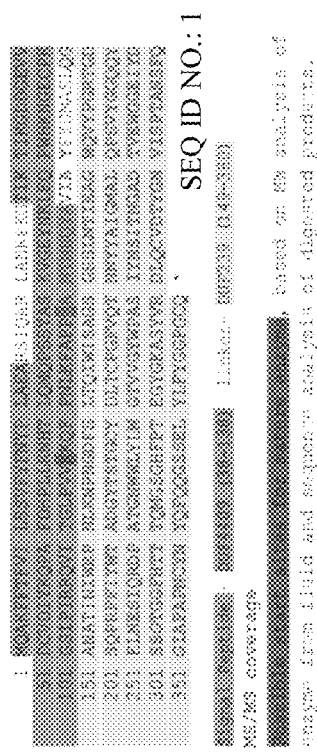
FIG. 4A shows the protein sequence for neprosin, identified from a combination of RNA-seq data, de novo peptide sequencing from nonspecific digests of the fraction analyzed by LC MS/MS, and extended to full length using 5' and 3' RACE. Domain boundaries based on designations in Pfam, and signal peptide detected by SignalP4.1.
Figure 4B:
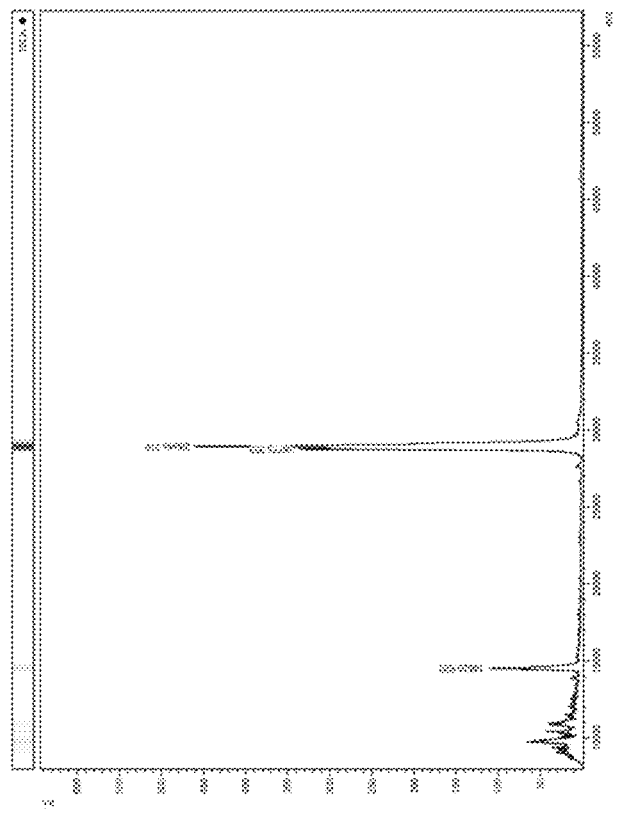
FIG. 4B shows MALDI-TOF analysis of the protein content of the isolated fraction confirms purity and suggests a mature enzyme is smaller than the full sequence in FIG. 4A. Estimated molecular weight is 28,860.
Figure 5B:
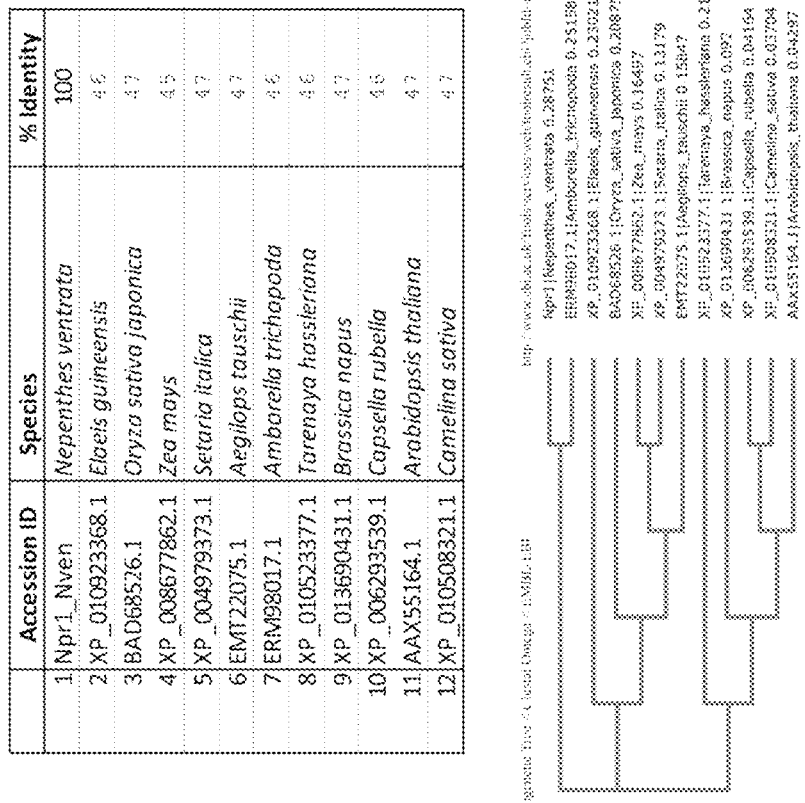
FIG. 5B shows BLAST hits with the highest percent identity to Npr1 (top) and hierarchical clustering based on Clustal Omega sequence alignments.
Figure 7:
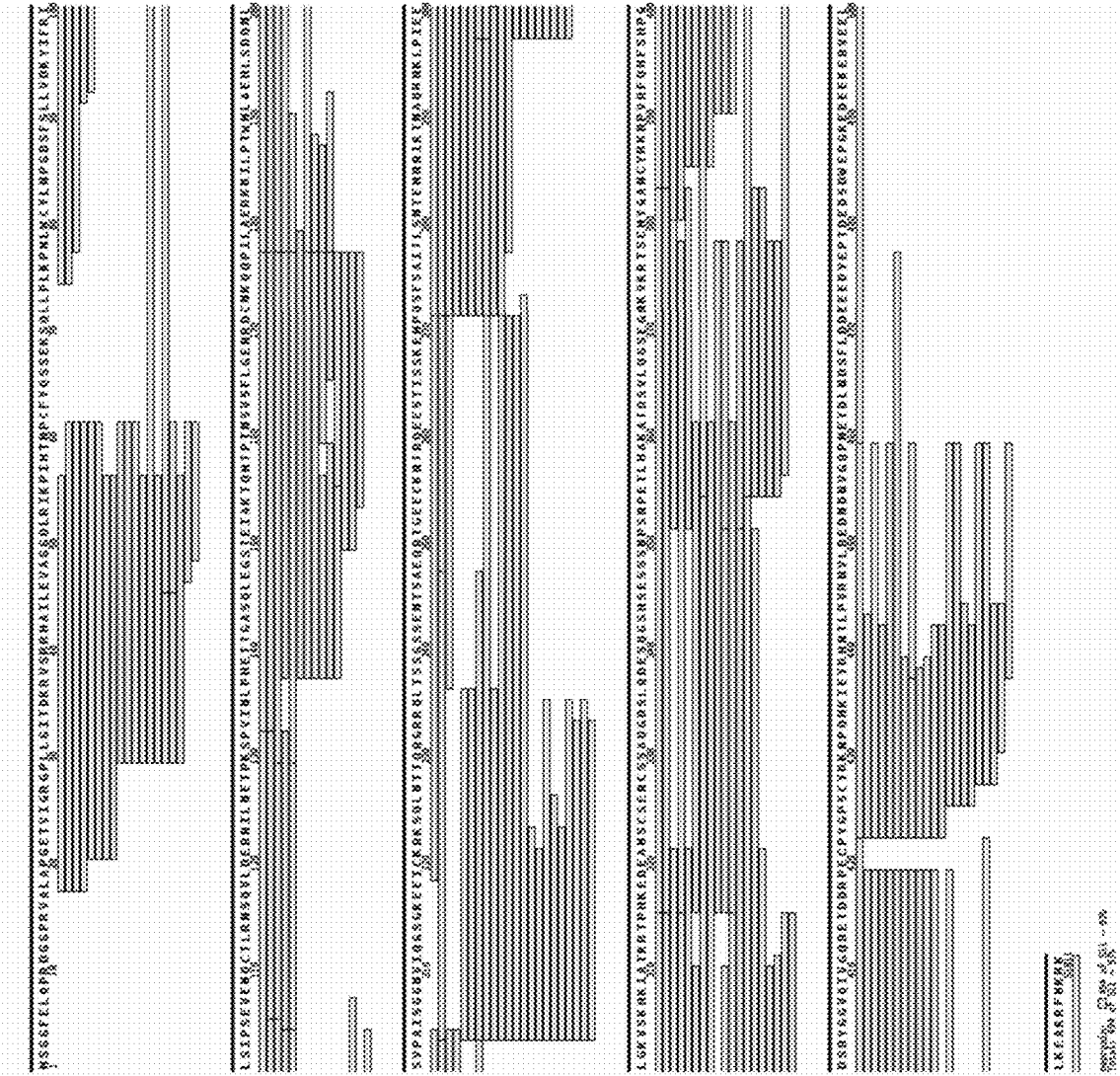
FIG. 7 shows a sequence map for the protein "Aprataxin and PNK-Like Factor" (APLF), a 511 residue protein with a moderately high frequency of proline residues. Data was generated using HCD fragmentation on an LC-Orbitrap Velos instrument, and data searched against the sequence of APLF in Mass Spec Studio assuming no enzyme specificity, and results were cut off at a peptide false discovery rate (FDR) of 0.5%. Figure discloses SEQ ID NO: 87.

Results:

A 4 kDa segment was assembled from overlapping peptides and the transcriptome searched to reveal a contig that, upon expansion with 5' and 3' RACE, identified a protein represented by two domains of unknown function Pfam entries DUF239 and DUF4409 (FIG. 3B). Mass analysis supports a mature enzyme consisting primarily of DUF239 (FIGS. 4A-4C). A functional prediction for DUF239 in Pfam suggests C-terminal peptidase activity, but this has never been demonstrated. The level of sequence identity shared with other members possessing a DUF239 domain, mostly found in plants, is only modest (FIGS. 5A and 5B). Interestingly, this enzyme is both structurally and functionally distinct from known proline-cleaving enzymes (FIG. 6). It suggests that DUF239 represents a previously unknown class of proline-directed protease. Proteolytic maps were generated using large protein standards, and the maps clearly indicate an endoprotease with dominant Pro-X cleavage specificity (FIG. 7). At 29 kDa, the enzyme is considerably smaller than any known prolyl endoproteases, and does not appear to have the substrate length restrictions observed with prolyl oligopeptidases. This newly-discovered proteolytic enzyme was named neprosin (Npr1).

Example 6: *Nepenthes* Protein Quantitation

Before testing the extract for gluten detoxification potential, and given the importance of dosage to the therapeutic concept, the concentration of the active proteolytic components was measured utilizing a method involving AQUA-peptides. The AQUA method requires identifiable tryptic peptides and complete digestion; stable isotope-labeled peptides representing the active enzymes were added as internal standards. Only nepenthesin I and neprosin could be monitored in this fashion, as mature nepenthesin II has no K or R residues.

A variation of the FASP protocol was applied to digest the fluid concentrate, and combined with the AQUA peptide quantitation method. Briefly, heavy-labeled peptides for nepenthesin I (GPLSLPSQLDVTK; SEQ ID NO.: 25) and neprosin (ASYVR; SEQ ID NO.: 26) were synthesized (Sigma-Aldrich). The fluid concentrate was denatured in 8 M urea at neutral pH and under reducing conditions. Protein was alkylated with iodoacetamide, and then digested with trypsin. AQUA peptides were added, and the samples were then purified for mass analysis. Digests were analyzed by reverse-phase LC-MS on an Orbitrap Velos ETD. The relative intensities of the light and heavy forms of the tryptic peptides measured in Xcalibur software and used to determine protein concentration. Progressively-longer digestion times and higher enzyme-to-substrate ratios were applied until protein concentrations reached a plateau. To estimate nepenthesin II levels required label-free methods (emPAI and T3PQ) applied to the nonspecific digest of the fluid protease fraction.

Results:

Complete digestion was achieved using an aggressive denaturing and digestion protocol. Nepenthesin I was present at 450+/−50 nM (n=3) and neprosin at 250+/−40 nM (n=3) in the concentrated fluid fraction. Based on the label-free proteomics data that was collected from the whole fluid sub-proteome, using the nonspecific digestion protocol, the concentration of nepenthesin II was approximately equivalent to nepenthesin I. For the purposes of dose evaluation in the gluten detoxification experiments, the total enzyme concentration in the concentrate was approximately 1.15 µM, consisting of 900 nM nepenthesin I/II and 250 nM neprosin.

Example 7: Digestion of Gliadin by *Nepenthes* Enzymes

Next, the digestion characteristics of crude gliadin were monitored over a range of *Nepenthes* enzyme concentrations. Digestion products were compared to pepsin-generated peptides as a control, using a number of methods. Digestion was performed at a pH of 2.5 in order to simulate gastric conditions alone. A second-stage of digestion at neutral pH using intestinal proteases (i.e. trypsin, chymotrypsin) was not used.

Crude gliadin (Sigma-Aldrich cat. # G3375) was ground to a powder. A stock gliadin slurry of 20-50 mg/ml was prepared in acidic solution (100 mM glycine HCl, pH 2.5) and briefly sonicated to further break up large particulates and promote suspension. Digestions of 10 mg/mL gliadin slurries were initiated by addition of enzyme (pepsin, fluid enzymes or both) and held at 37° C. with gentle rotation. Digest progress was monitored by gravimetric analysis, optical transmission, SDS-PAGE and mass spectrometry. For gravimetric analysis, digests were quenched by boiling and treated with TCA/chloroform, followed by centrifugation to recover undigested or poorly digested protein. For monitoring with optical transmission, digestion reactions were conducted in 96-well plate with ≥3 replicates of each reaction condition, and turbidity monitored at 595 nm at 37° C. every 2 minutes, for 90 minutes (SpectraMax plate reader, Molecular Devices). The plate was shaken at medium speed briefly between measurements. The digests were quenched after 90 min reaction by boiling for 10 minutes (confirmed to have no impact on digestion profile, a posteriori). An aliquot of the reaction mixture was analyzed on an 8% SDS-PAGE gel. The remaining amount was centrifuged and the supernatant was analyzed by mass spectrometry.

Figures 8C, 8D:
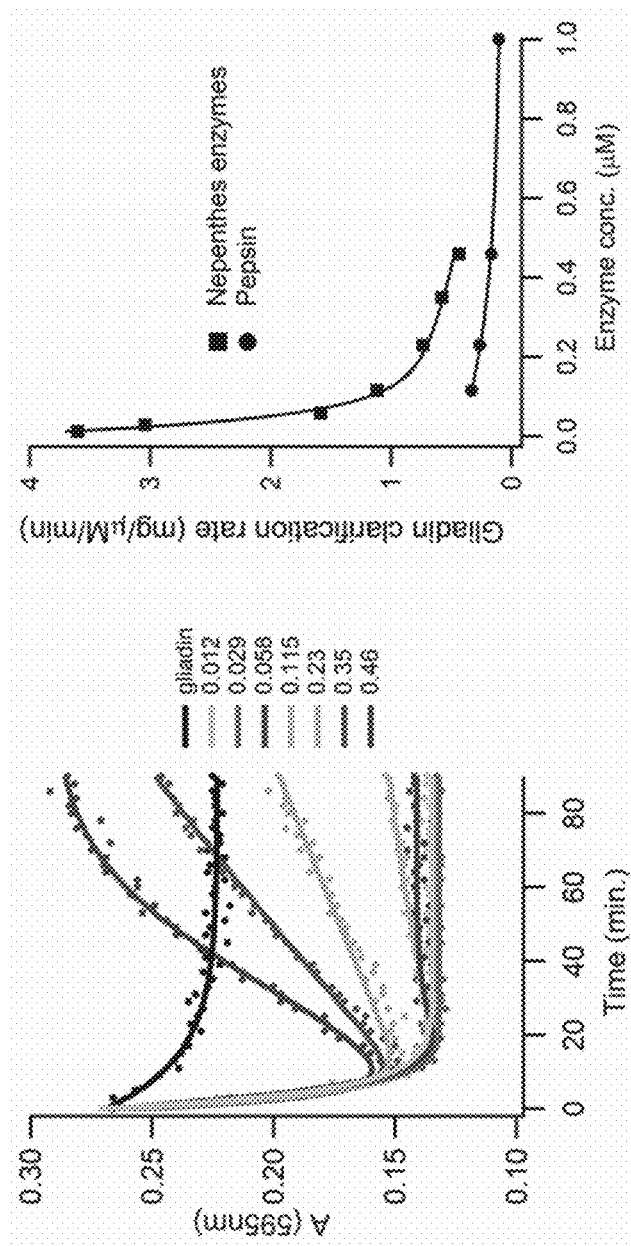
FIG. 8C shows a time-course digestion of 10 mg/ml gliadin (pH 2.5 at 37° C.) with the indicated micromolar concentrations of *Nepenthes* fluid proteases supplemented with 5 μM pepsin. Turbidity of the digested gliadin was monitored as absorbance at 595 nm ($A_{595}$). Black lines represent the turbidity of the gliadin slurry in the absence of protease. Measurement precision was <3% RSD (n=3).
FIG. 8D shows slurry clarification rates, measured at 90% of the maximal effect, for digestions using *Nepenthes* fluid enzymes alone, and pepsin alone. Data taken from FIGS. 8A-8C. Values reported as milligrams of gliadin per micromolar enzyme concentration per minute digestion time.

Results:

First, clarification rates of a 10 g/L slurry of a crude gliadin extract were monitored using optical density measurements (FIGS. 8A-8C). Pepsin was applied up to the higher end of the human gastric concentration range (~5 µM), and fluid proteases to approximately $\frac{1}{10}^{th}$ of this amount. Pepsin alone achieved a maximum clarification rate of 0.3 mg/µM/min (FIG. 8D). Some residual opacity was noted that may be due to water-insoluble high molecular-weight glutenins or typical residues from the extraction process, such as lipids. The fluid proteases alone increased the clarification rate over 10-fold (FIG. 8D). Interestingly, at the higher levels of fluid proteases used in this test, opacity increased with digestion time, and co-digestion with pepsin amplified the effect. This finding is consistent with the emulsifying properties of gluten hydrolysates. The stabilization of lipids in the crude fraction by an emulsion would increase scattering and would rise as digestion progresses. The effect prevented measurement of the clarification rate using the combination of pepsin and fluid proteases. Nevertheless, the clarification rate of the fluid extract is high, and the fluid proteases appear to digest gliadin synergistically with pepsin.

Example 8: Proteomic Analysis of Gliadin Digests

The above results suggest an effective digestion process, but they do not convey information regarding the completeness of the digestion. Using the pepsin-resistant 33mer, the evolution of peptide products was monitored under dilute conditions.

Supernatant was analyzed by data-dependent LC-MS/MS, in two 1-hour reversed phase gradient runs, configured for top-10 ion selection using CID in a high/low configuration. In one run, ion selection was restricted to 2+ and higher charge states. In the other run, ion selection was applied to 1+ charge states only. Data from both runs were combined and searched against all UniprotKB/Swiss-Prot entries for gliadin and glutenin from *Triticum aestivum* (25 proteins), using Mascot v2.3, configured for non-specific digestions and filtered for peptide hits with p<0.05. For estimation of peptide size distribution, all LC-MS spectra were combined and deconvoluted in Protein Deconvolution v1.0, with appropriate settings. For label-free quantitative analysis using the subset of the digest identified in the database search, the hit list was combined with the raw data in Mass Spec Studio and used to generate a set of peptide ion chromatograms, integrated over all isotopes to determine a weight-average intensity for each peptide sequence identified.

To determine the impact of added protein on gliadin digestion efficiency, bovine serum albumin (BSA, 90 mg/mL) was applied in excess over gliadin (10 mg/mL) and digested using 0.46 µM fluid protease and 5 µM pepsin. Samples were digested at 37° C., pH 2.5 and an aliquot removed at multiple timepoints for analysis. Samples were diluted and quenched by boiling. As a control, a similar course of reactions was performed in the absence of BSA. Prior to mass analysis of digests, fixed amounts of two AQUA peptides (YLQLQPFPQP [SEQ ID NO.: 27] and LQLQPFPQP [SEQ ID NO.: 28]) representing an antigenic region of α-gliadin and 1 AQUA peptide representing an antigenic region of γ-gliadin (QQPYPQQP; SEQ ID NO.: 29) were added (heavy-labeled amino acids underlined). Multiple transitions for each peptide (light and heavy forms) were monitored using a scheduled MRM method on a reversed-phase LC-MS system (Eksigent microLC on a Qtrap 6500). Data was collected in triplicate for each digest and timepoint. Chromatographic peak intensities for the respective quantifier transitions were measured, and standardized against the corresponding transitions for the corresponding heavy peptide.

Results:

At 10 min, approximately 50% of 33mer was digested, and full digestion was achieved at 100 min (FIG. 9A). Neither pepsin nor a bacterial prolyl endoprotease from *Myxococcus xanthus* (MX) were able to hydrolyse the peptide to any appreciable extent (data not shown), in equivalent digestion conditions at their optimum pH (2 and 7 respectively). To extend these findings, slurry digestion products were extensively mapped using proteomics techniques. First, SDS-PAGE showed extensive digestion of total protein using fluid proteases, which could not be achieved with pepsin alone (FIG. 9B-9D). Next, data-dependent LC-MS/MS data were collected on the digest products to globally characterize peptide size and sequence. Using a label-free method that quantifies all peptide signals from LC-MS data regardless of identity, it was observed that a high concentration of pepsin (5 µM) hydrolyzes gliadin to a moderate level as expected (FIG. 9E), yielding an average peptide length of 19.2 residues. The fluid extract saturates at an average length of 13.2 residues using much lower doses (0.23 µM). With pepsin co-digestion the average length reduces further to 11.5 residues. The fluid proteases also generated a narrower distribution of product length (FIG.

9F). High concentrations of pepsin produce a digest with 25 wt % of the detected product having a molecular weight greater than 4000 Da, confirming the proteolytically-resistant properties of gluten. The fluid proteases reduce this fraction to less than 2 wt %.

Figure 10:
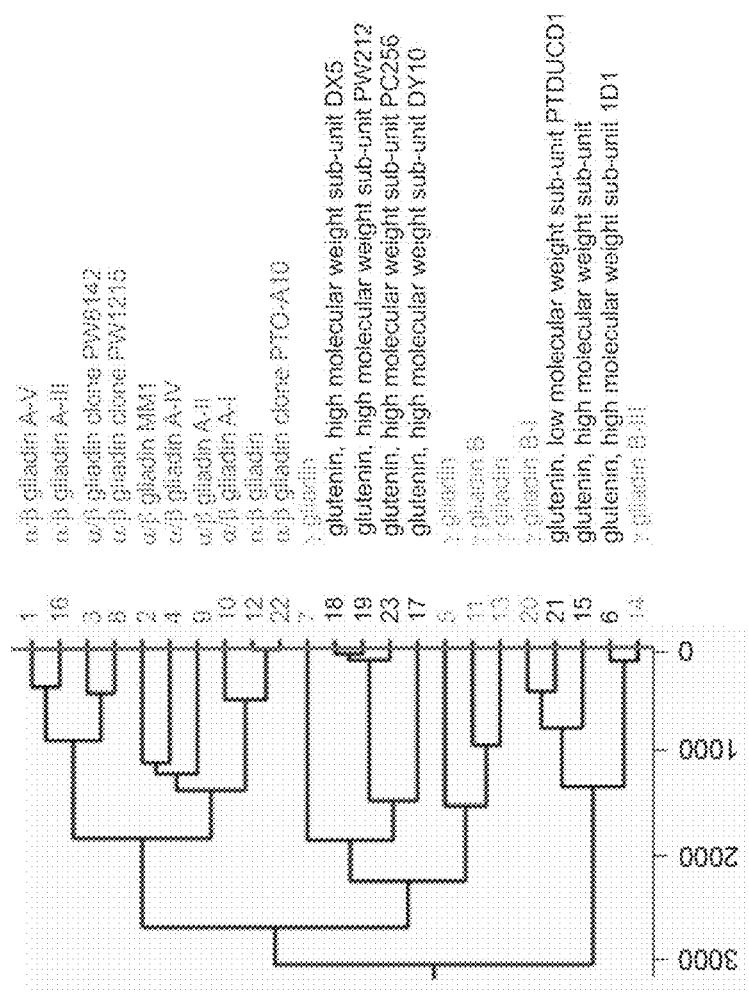
FIG. 10 shows a hierarchical cluster-graph related to the data in Table 4. Branch-points represent the cumulative score for significant peptides matches that would have to be discarded to remove any differentiation between branches.

The MS/MS peptide fragmentation data support an identification of digestion products, and an alternative quantitative analysis. Based on a database search comprised of known gluten proteins, the crude gliadin fraction contains a distribution of α/β-gliadin and γ-gliadin isotypes. Many peptides were also evident for the glutenins. The low molecular weight subunit is particularly abundant, highlighting the crude nature of the conventional gliadin extraction process (Table 4 and FIG. 10). The weighted average peptide length for the 5 µM pepsin digest was 16.9 residues (based on 1030 features), which accounted for only 13% of the total digest signal. The fluid protease digestion at 0.46 µM produced an average peptide length of 11.2 residues (1370 features), accounting for 30% of the total signal. Co-digestion using these two concentrations generated a weighted average of 10.2 residues (1571 features) accounting for 40% of the digest signal. This fraction represents a high signal usage rate in a proteomic experiment. That is, the unidentified fraction mostly represents a combination of sampling rate limitations and insignificant peptide scores, rather than undigested protein. Longer digestions using the combined proteases reduces total LC-MS signal without changing the size distribution, consistent with a proteomics method that cannot detect peptides <6 amino acid residues in length. Taken together, the proteomics data point to an extensive digestion of crude gliadin under the action of low-concentration fluid proteases, where co-digestion with pepsin enhances proteolysis even when fluid enzymes appear saturating.

TABLE 4

Proteomic characterization of crude gliadin preparation

| # | Accession # | Mascot Protein Score | Mass (Da) | Matches[a] | Sequences[a] | emPAI[b] | Name |
|---|---|---|---|---|---|---|---|
| 1 | gi\|121094\|sp\|P04725.1\|GDA5_WHEAT | 10424 | 36643 | 489 (450) | 116 (110) | 36883.01 | RecName: Full = Alpha/beta-gliadin A-V; AltName: Full = Prolamin; Flags: Precursor |
| 2 | gi\|121098\|sp\|P18573.1\|GDA9_WHEAT | 9282 | 35375 | 425 (391) | 124 (119) | 128026.67 | RecName: Full = Alpha/beta-gliadin MM1; AltName: Full = Prolamin; Flags: Precursor |
| 3 | gi\|121096\|sp\|P04727.1\|GDA7_WHEAT | 8302 | 36095 | 409 (372) | 107 (103) | 19651.69 | RecName: Full = Alpha/beta-gliadin clone PW8142; AltName: Full = Prolamin; Flags: Precursor |
| 4 | gi\|121093\|sp\|P04724.1\|GDA4_WHEAT | 8238 | 34217 | 355 (316) | 102 (96) | 13300.51 | RecName: Full = Alpha/beta-gliadin A-IV; AltName: Full = Prolamin; Flags: Precursor |
| 5 | gi\|121101\|sp\|P08453.1\|GDB2_WHEAT | 8194 | 37099 | 523 (424) | 116 (113) | 15151.72 | RecName: Full = Gamma-gliadin; Flags: Precursor |
| 6 | gi\|121457\|sp\|P10386.1\|GLTB_WHEAT | 8085 | 34906 | 455 (425) | 127 (122) | 74512.08 | RecName: Full = Glutenin, low molecular weight subunit 1D1; Flags: Precursor |
| 7 | gi\|121104\|sp\|P21292.1\|GDBX_WHEAT | 7655 | 34278 | 447 (361) | 106 (99) | 4284.08 | RecName: Full = Gamma-gliadin; Flags: Precursor |
| 8 | gi\|121095\|sp\|P04726.1\|GDA6_WHEAT | 7417 | 33920 | 377 (332) | 83 (80) | 3201.36 | RecName: Full = Alpha/beta-gliadin clone PW1215; AltName: Full = Prolamin; Flags: Precursor |
| 9 | gi\|121091\|sp\|P04722.1\|GDA2_WHEAT | 6989 | 33640 | 345 (306) | 110 (101) | 35998.64 | RecName: Full = Alpha/beta-gliadin A-II; AltName: Full = Prolamin; Flags: Precursor |
| 10 | gi\|121090\|sp\|P04721.1\|GDA1_WHEAT | 6564 | 30384 | 309 (281) | 103 (98) | 51350.05 | RecName: Full = Alpha/beta-gliadin A-I; AltName: Full = Prolamin; Flags: Precursor |
| 11 | gi\|121103\|sp\|P06659.1\|GDBB_WHEAT | 6199 | 32946 | 506 (391) | 110 (101) | 12781.88 | RecName: Full = Gamma-gliadin B; Flags: Precursor |
| 12 | gi\|67464993\|sp\|P02863.2\|GDA0_WHEAT | 6117 | 32943 | 284 (250) | 98 (93) | 8722.77 | RecName: Full = Alpha/beta-gliadin; AltName: Full = Prolamin; Flags: Precursor |
| 13 | gi\|121099\|sp\|P08079.1\|GDB0_WHEAT | 5659 | 29035 | 457 (344) | 108 (93) | 13280.46 | RecName: Full = Gamma-gliadin; Flags: Precursor |

TABLE 4-continued

Proteomic characterization of crude gliadin preparation

| # | Accession # | Mascot Protein Score | Mass (Da) | Matches[a] | Sequences[a] | emPAI[b] | Name |
|---|---|---|---|---|---|---|---|
| 14 | gi\|121102\|sp\|P04730.1\|GDB3_WHEAT | 5003 | 27320 | 270 (258) | 73 (69) | 2435.24 | RecName: Full = Gamma-gliadin; AltName: Full = Gliadin B-III |
| 15 | gi\|121455\|sp\|P10385.1\|GLTA_WHEAT | 4238 | 40994 | 407 (318) | 89 (85) | 354.42 | RecName: Full = Glutenin, low molecular weight subunit; Flags: Precursor |
| 16 | gi\|121092\|sp\|P04723.1\|GDA3_WHEAT | 3876 | 32216 | 185 (179) | 67 (63) | 698.01 | RecName: Full = Alpha/beta-gliadin A-III; AltName: Full = Prolamin; Flags: Precursor |
| 17 | gi\|121449\|sp\|P10387.1\|GLT0_WHEAT | 3592 | 69587 | 154 (139) | 70 (67) | 21.66 | RecName: Full = Glutenin, high molecular weight subunit DY10; Flags: Precursor |
| 18 | gi\|300669719\|sp\|P10388.5\|GLT5_WHEAT | 3555 | 90239 | 176 (169) | 63 (58) | 7.72 | RecName: Full = Glutenin, high molecular weight subunit DX5; Flags: Precursor |
| 19 | gi\|121453\|sp\|P08489.1\|GLT4_WHEAT | 2819 | 89120 | 141 (135) | 54 (49) | 5.25 | RecName: Full = Glutenin, high molecular weight subunit PW212; Flags: Precursor |
| 20 | gi\|121100\|sp\|P04729.1\|GDB1_WHEAT | 2814 | 34230 | 239 (188) | 70 (64) | 480.43 | RecName: Full = Gamma-gliadin B-I; Flags: Precursor |
| 21 | gi\|121459\|sp\|P16315.1\|GLTC_WHEAT | 2043 | 33358 | 225 (160) | 52 (47) | 83.02 | RecName: Full = Glutenin, low molecular weight subunit PTDUCD1; Flags: Precursor |
| 22 | gi\|121097\|sp\|P04728.1\|GDA8_WHEAT | 1799 | 21505 | 62 (61) | 32 (31) | 86.31 | RecName: Full = Alpha/beta-gliadin clone PTO-A10; AltName: Full = Prolamin |
| 23 | gi\|121450\|sp\|P02861.1\|GLT1_WHEAT | 484 | 10889 | 29 (28) | 9 (8) | 7.99 | RecName: Full = Glutenin, high molecular weight subunit PC256 |

[a]First number the total count. Number in brackets the total count above the significance threshold ($p < 0.05$).
[b]*Exponentially Modified Protein Abundance Index*, providing a label-free relative quantitation of proteins based on protein coverage using the peptides matches in the search result. While based on partially redundant (non-unique) peptide identifications, sufficient numbers of unique peptides are evident for each entry in the table, as supported by the hierarchical cluster-graph in FIG. 10, where branch-points represent the cumulative score for significant peptides matches that would have to be discarded to remove any differentiation between branches.

Figure 11A:
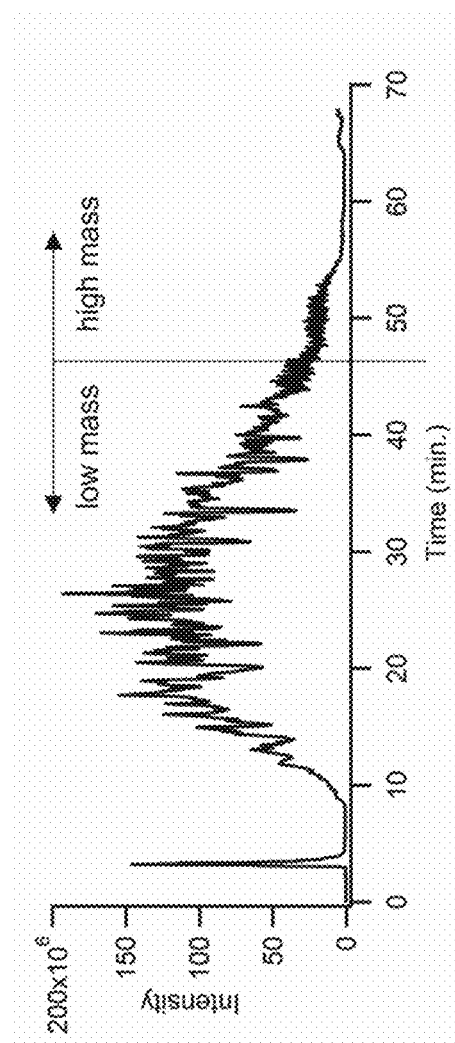
FIG. 11A is a sequence coverage map for α/β-gliadin MM1 (Uniprot P18573.1) in crude gliadin, and associated total ion chromatograms. Digestion used 0.46 μM fluid protease for 90 min at 37° C. Sequence coverage is highlighted using red text, with cleavage sites marked in bold cyan. The chromatograms are marked with approximate boundaries for the sizes of digest products. Figure discloses SEQ ID NO: 92.
Figure 11B:
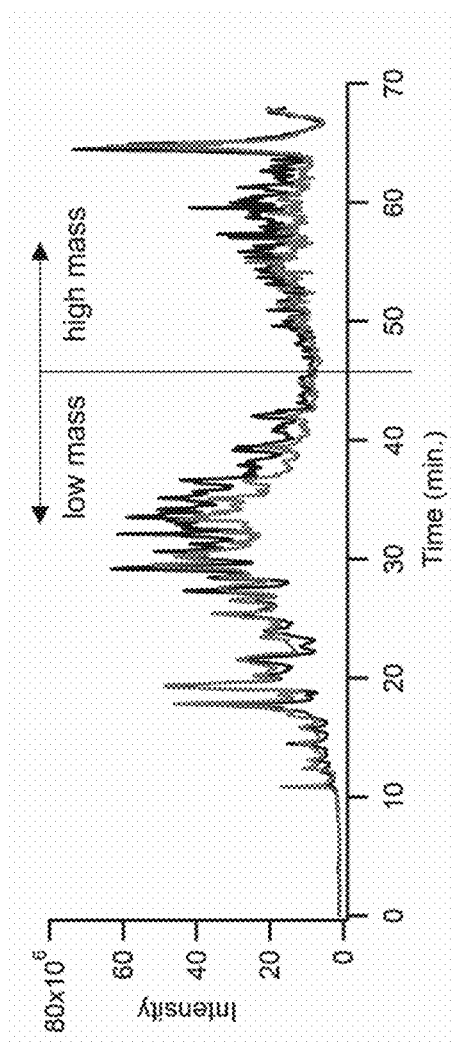
FIG. 11B shows a sequence coverage map for α/β-gliadin MM1 (Uniprot P18573.1) in crude gliadin, and associated total ion chromatograms. Black trace represents a neprosin concentration matched to the highest level tested in the fluid extract in A (~0.1 μM) and the red trace represents double this concentration (~0.2 μM). Sequence coverage is highlighted using red text, with cleavage sites marked in bold cyan. The chromatograms are marked with approximate boundaries for the sizes of digest products. Figure discloses SEQ ID NO: 92.

Inspecting the peptide sequences, large numbers of Pro-X cleavage sites were observed. To test if neprosin alone was responsible for generating the significant increase in digestion efficiency, the crude gliadin slurry was digested using purified neprosin. A bimodal distribution of products was observed, consisting of both low and high molecular weight fractions (FIG. 11). The weighted average peptide length for the low molecular weight fraction was 12.5, accounting for 10% of the total signal, but doubling the concentration did not diminish the bimodality, nor significantly improve the depth of coverage. The high molecular weight fraction remained substantial, confirming that the aspartic proteases have a role in accelerating digestion. The natural aspartic protease to neprosin ratio was reconstituted using recombinant nepenthesin II (produced with previously described methods, such as those described in PCT Pub. Nos. WO 2015/192211 and WO 2014/138927, each of which is incorporated herein by reference in its entirety) and the purified neprosin; the gliadin digestion profile was equivalent to that of the fluid extract (not shown). This confirms that the proteolytic activity of the extract arises from the aspartic proteases and neprosin alone.

Example 9: Deamidization of Antigenic Regions

Whether enhanced digestion profiles would impact deamidation in antigenic regions was investigated. The recognition of immunodominant peptides by T cells is amplified when these peptides are deamidated in their core binding region by tissue transglutaminase 2 (TG2), particularly at position P4 or P6 in HLA DQ2 associated celiac disease. Deamidation is dependent on both peptide sequence and length, and the deamidation levels for key antigenic regions are significantly higher than elsewhere in sequence. Crude gliadin digests were analyzed for the conversion of non-deamidated peptides to deamidated forms, and sorted all the peptides using a previously published algorithm for the identification of DQ2 binding motifs.

Supernatants from crude gliadin digests were treated with 0.1 mg/mL human transglutaminase-2 (R&D Systems, Cat. 4376-TG-050) in 100 mM Tris-HCl pH 7.5, 2 mM $CaCl_2$ at 37° C. for 90 minutes, and quenched at 95° C. for 15 minutes, following a published protocol. Treated digests were analyzed by data-dependent LC-MS/MS as described above, allowing for variable N and Q deamidation in database searches. The chromatographic intensities of all positively identified deamidated and nondeamidated peptides were determined using Mass Spec Studio and ratios expressing the relative degree of deamidation determined on a per-peptide basis.

Figure 9G:
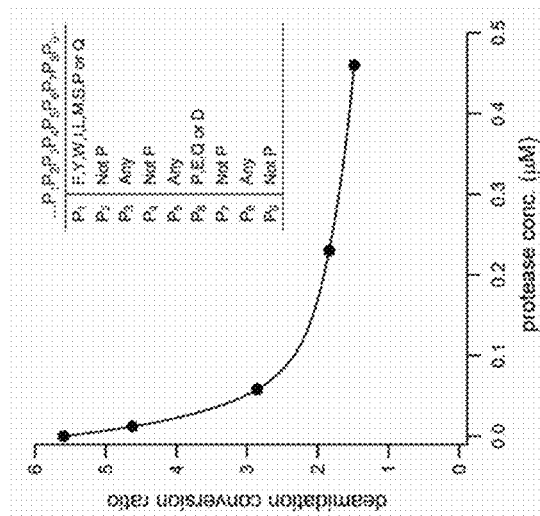
FIG. 9G shows TG2-induced conversion of gliadin digestion products to deamidated counterparts. Fractional deamidation quantified for all peptides from ion chromatogram intensities; data presented as a ratio, where the antigenic peptide deamidation is normalized to the non-antigenic peptide deamidation at the indicated protease concentration. Antigenic regions defined using the DQ2 criteria, inset table.
Figure 9F:
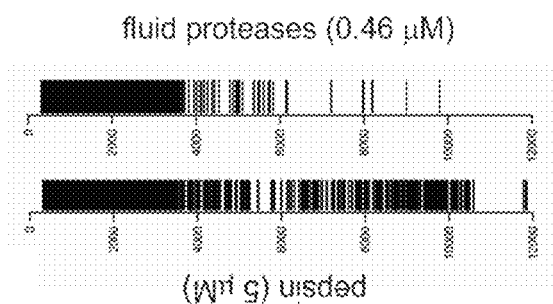
FIG. 9F shows a barcode representation of deconvoluted spectra from FIG. 9E, at the noted enzyme concentrations, showing molecular weight distribution with simple binary model of intensities, (white: <0.2%, black: >0.2%).
Figure 9E:
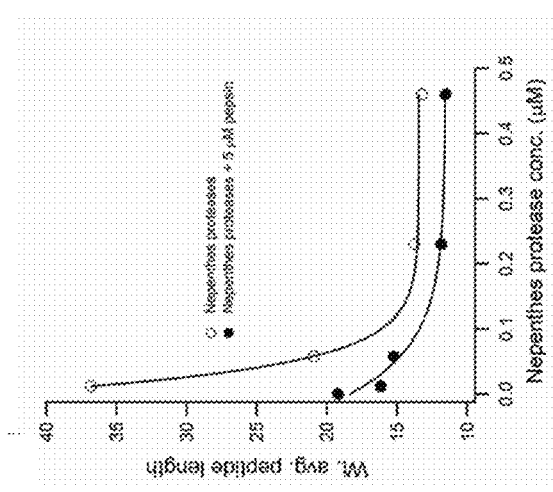
FIG. 9E shows the weighted average peptide length as a function of fluid protease concentration, with or without pepsin, using ion chromatogram intensities for weighting. Peptide data from LC-MS/MS runs, with intensities obtained using Protein Deconvolution 1.0.

As shown in FIG. 9G (and Table 5), pepsin digestion generated over 5.5 times higher peptide conversion in antigenic regions compared to non-antigenic regions. By applying increasing concentrations of the fluid proteases, the conversion levels in the antigenic regions approached those of the non-antigenic sequences, especially when considering to the relative Q content for each category of peptide (a conversion ratio of 1.3 is expected based on the higher Q content in antigenic peptides alone, at high enzyme concentration).

Figure 12A:
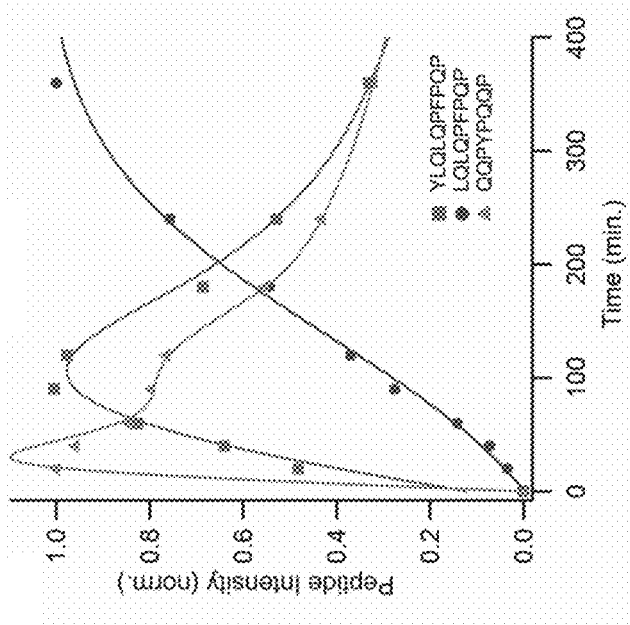
FIG. 12A shows a temporal digestion profile of three peptides (top) spanning the antigenic regions of α and β-gliadin. 10 mg/ml crude gliadin slurry supplemented with 0.46 μM fluid proteases (4:1 nepenthesins to neprosin) and 5 μM pepsin, at t=0. Data color coded with the peptide designations at the top, representing average determinations (n=3, relative standard deviations <2%), standardized against stable-isotope labeled versions of the peptide, and reported as values normalized to the maximum intensities. Figure discloses SEQ ID NOS 93-94 and 27-29, respectively, in order of appearance.
Figure 12B:
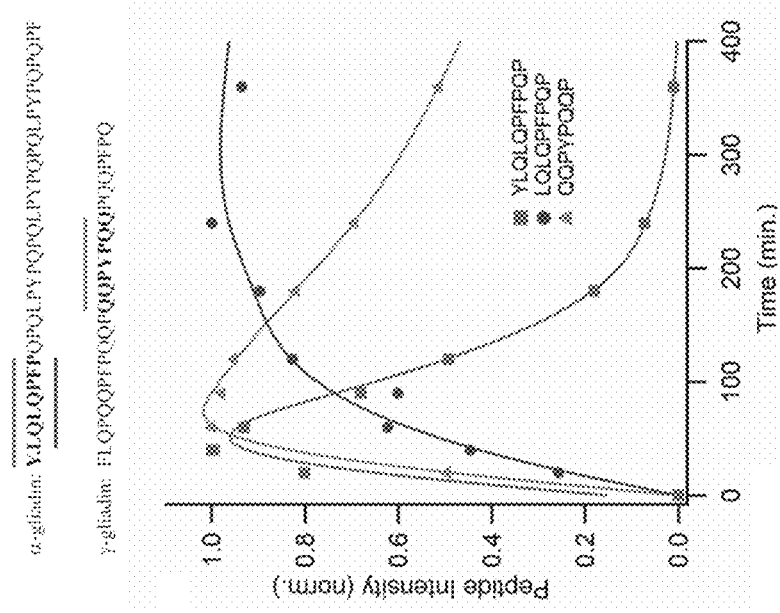
FIG. 12B shows a temporal digestion profile of three peptides (top FIG. 12A) spanning the antigenic regions of α- and β-gliadin. 10 mg/ml crude gliadin slurry and 90 mg/ml bovine serum albumin supplemented with 0.46 μM fluid proteases (4:1 nepenthesins to neprosin) and 5 μM pepsin, at t=0. Data color coded with the peptide designations at the top, representing average determinations (n=3, relative standard deviations <2%), standardized against stable-isotope labeled versions of the peptide, and reported as values normalized to the maximum intensities. Figure discloses SEQ ID NOS 27-29, respectively, in order of appearance.

Example 10: Effect of Non-Gluten Protein on Efficacy of Gluten Detoxification by *Nepenthes* Enzymes Based on these analyses, an extensive digestion of crude gliadin slurry can be achieved using a substrate to fluid protease ratio of 1265:1, where the enzyme consists of a 4:1 blend of nepenthesin to neprosin. To test the influence of added non-gluten protein on the effectiveness of gluten detoxification, a digestion experiment was performed where gliadin consisted of only 10 wt % of the total protein, by adding 90 g/L serum albumin to the 10 g/L crude gliadin slurry. Fluid protease was maintained at 0.46 µM and pepsin at 5 µM. The excess of albumin prevented use of data-dependent proteomics methods, so select peptides from the antigenic regions of α and γ-gliadin were monitored using a targeted proteomics methods and AQUA peptides as internal standards (see above). Applying the method against an albumin-free slurry digest confirmed the fragmentation of the antigenic regions (FIG. 12A), as described above, and shows that antigen processing is extensive by 60 min. The digest containing the large excess of albumin extended the α-gliadin antigen fragmentation timeframe only two-three-fold, but it had no significant effect on the fragmentation of the γ-gliadin antigen.

Example 11: Effect of Nepenthesin on Intestinal Barrier Dysfunction and Gliadin Sensitivity The efficacy and tolerability of the fluid protease extract was tested in a transgenic NOD/HLA-DQ8 mouse model that exhibits intestinal barrier dysfunction and gliadin sensitivity in a DQ8-dependent manner.

Figure 13:
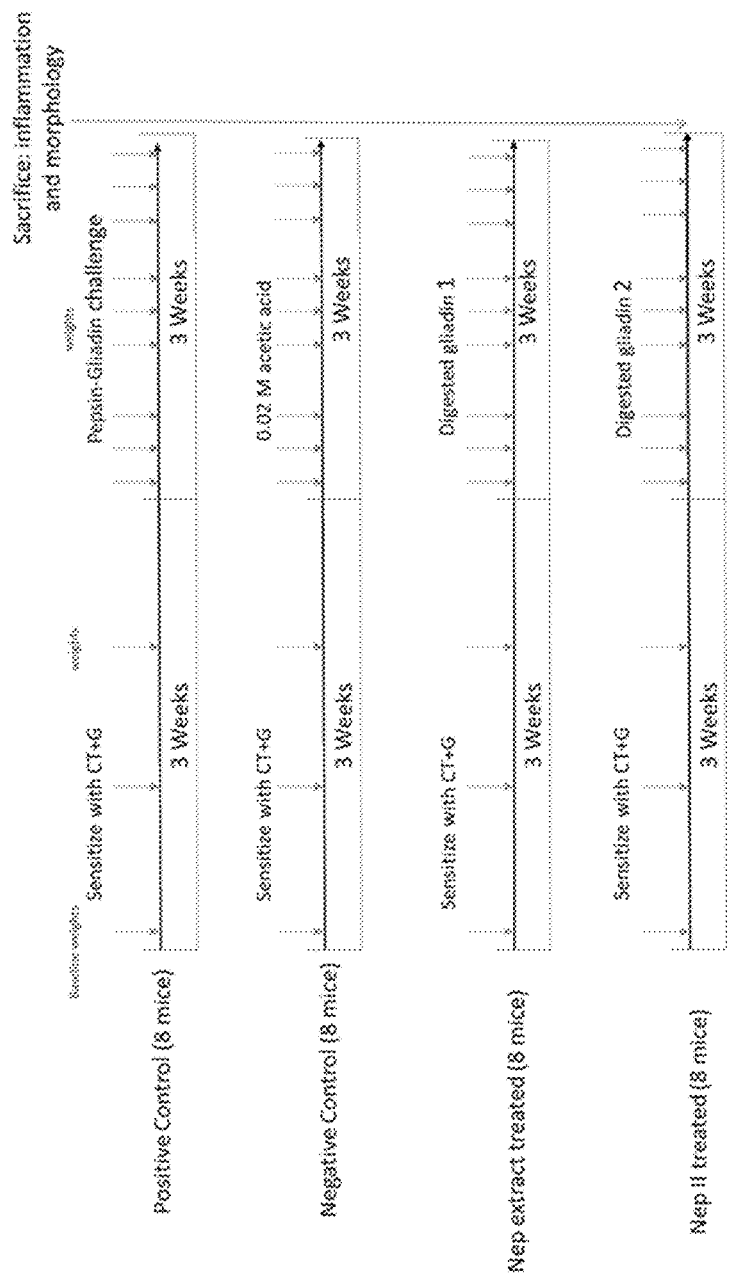
FIG. 13 shows the experiment design and gliadin feeding schedule of NOD DQ8 transgenic mice. Four groups of mice (n=8 per group) were sensitized using cholera toxin (CT) and pepsin-gliadin (P-G) once per week for three weeks. P-G was prepared with 100:1 wt. ratio of gliadin to enzyme. Each group was then challenged three times per week for three weeks with (A) P-G doses as a positive control for intestinal inflammation (B) 0.02M acetic acid vehicle (C) gliadin codigested with pepsin at a 100:1 ratio and with fluid enzyme concentrate at a 264:1 ratio (D) gliadin codigested with pepsin at a 100:1 ratio and with nepenthesin II at a 100:1 ratio. All doses were prepared in 5 mg quantities, digested for 90 min. at 37° C. then lyophilized. Dried feed was reconstituted using 0.02M acetic acid at dosing.
Figure 14:
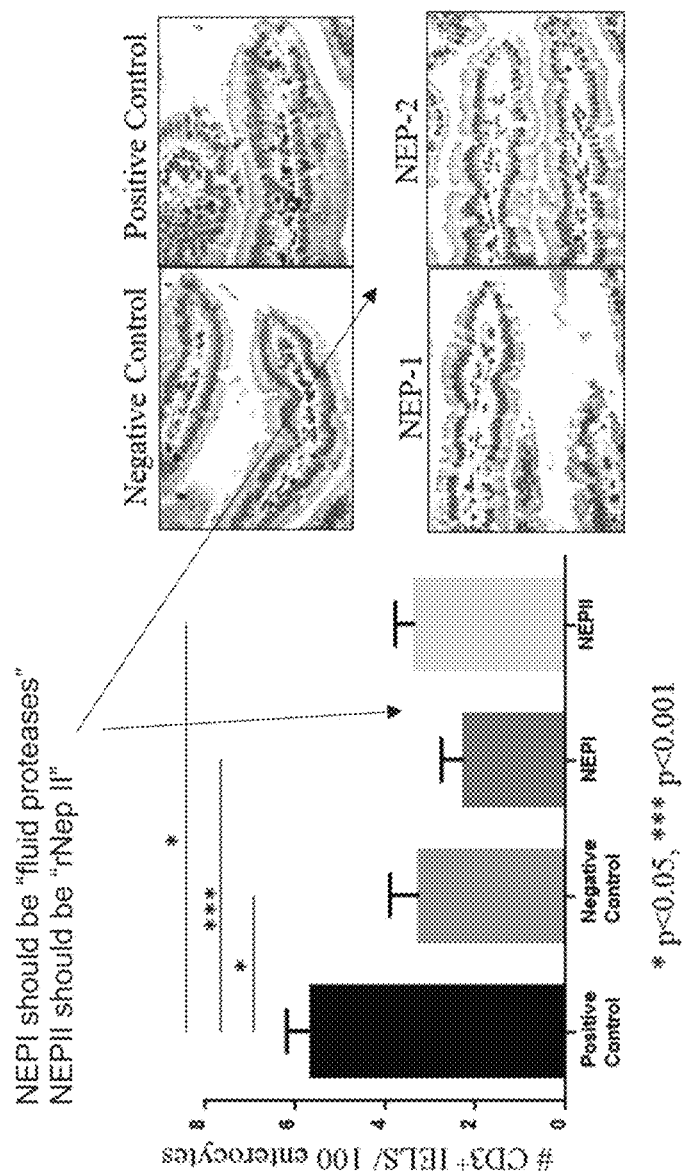
FIG. 14 shows intraepithelial lymphocyte counts (IELS) quantitated by immunostaining of intestinal tissue, for sensitized mice challenged with pepsin-treated gliadin (positive control), vehicle alone (negative control, gliadin-free diet), fluid protease-treated gliadin (1:264 ratio) and recombinant nepenthesin-II treated gliadin (1:100 ratio). Representative immunostained sections of intestinal tissues for the four states shown to the right. Statistical significance (n=8 for each state, *p<0.05, ***p<0.001).

NOD DQ8 mice were sensitized with cholera toxin (CT) and pepsin-gliadin (P-G) digest to break oral tolerance to gliadin, and continuously fed with P-G over a three week period as a positive control for intestinal inflammation. (FIG. 13). Negative controls were treated with CT and P-G, but left free of subsequent oral gliadin challenges. Sensitized mice were split into two groups, where one group was challenged with gliadin co-digested with pepsin and fluid proteases, and the other was challenged with gliadin co-digested with pepsin and recombinant nepenthesin II. Eight mice were used in each of the four groups. Mice were evaluated for overall appearance (movement, eye opening, grooming) and body weights were recorded throughout the experiments. Intestinal tissue were tested by immunohistochemistry for CD3+ intraepithelial lymphocytes. Animal studies complied with all institutional ethical guidelines.

Results:

Mice fed crude gliadin digested with pepsin in 5 mg doses over a three week period after sensitization had significant increases in small intestinal CD3+ intraepithelial lymphocyte (IEL) counts as expected (FIG. 13). As a control, a cohort of sensitized mice was treated with vehicle only over the same period, to mimic a gliadin-free diet, and IEL counts were significantly lower. These two controls provided a means of quantitating the effects induced by the plant extract. The enriched fluid protease fraction and recombinant nepenthesin II were tested. Both were well tolerated, and both generated significant reductions in IEL counts, to levels indistinguishable from the gliadin-free diet control. Surprisingly, these results show that supplementation with a non-canonical aspartic protease alone can induce a measurable effect, although the presence of neprosin likely improves efficacy.

DISCUSSION

The *Nepenthes* genus of pitcher plants have adapted to growth in nitrogen-deficient conditions by attracting and trapping nitrogen-rich prey within the lower reaches of the pitcher leaf, a region that contains secretions capable of digesting invertebrates, plant matter, and animal waste. The pitcher achieves digestion without the benefit of mastication, in a single stage equivalent of a whole mammalian digestive tract. Chitinases, phosphatases, ribonucleases and proteases are involved in breaking down prey, but remarkably little is known about the specific enzymatic components driving this impressive feat of nutrient capture and uptake. The unusual amino acid composition of the protein components and the lack of available sequence databases have prevented a thorough proteomic characterization. Two aspartic proteases uncovered during initial investigations (nepenthesin I and II) have received the most study to date, and have been presumed to define the proteolytic capacity of the fluid. The fluid possessed a cleavage specificity profile most unusual for aspartic proteases alone. The nepenthesins are non-canonical in their cleavage specificity, cleaving after hydrophobic residues like pepsin does, but also possessing an unusual tryptic and chymotryptic character at low pH. A robust C-terminal proline cleavage activity was observed in the fluid as well, which was not reconstituted by the aspartic proteases alone. These findings stimulated our interest in evaluating the secretions for use in gluten detoxification, and we set out to uncover the enzyme responsible for proline cleavage.

The current study demonstrates that the proline cleavage characteristic of the fluid is separable from the action of the aspartic proteases, and together comprises a potent gluten digestion profile. Neprosin is the first characterized member of what appears to be a new class of prolyl endoprotease, defining a core function for an unknown domain that is well represented in plants. The sequence identity shared with other members of DUF239 is only modest, suggesting that, like the aspartic proteases, this prolyl endoprotease may have certain properties outside the norm for the class. Further research into other members of DUF239 is warranted. Nevertheless, while neprosin is important for a robust digestion profile, the plant aspartic proteases contribute to an efficient process. The surprising reduction in intestinal inflammation when nepenthesin II alone was combined with pepsin highlights the non-equivalent nature of these aspartic proteases. Pepsin is also more effective at gliadin digestion in the presence of fluid proteases (FIG. 9E), suggesting the possibility of synergy between host and plant proteases.

These findings widen the possibilities for treating celiac disease through an enzyme supplementation strategy. Very low enzyme levels generate considerably enhanced solubilization rates for gliadin slurries, and improved completeness of digestion under gastric conditions, reducing deamidation and the antigenicity of gluten. We suggest that supplementation with a non-specific aspartic protease in the nepenthesin class is an important element of any concept requiring gastric digestion. In the complex milieu of the stomach, efficient total protein breakdown will be required before a further reduction of gluten protein can be effective, which appears to be the role of nepenthesin. The finding that nepenthesin supplementation alone leads to reduced inflammation, albeit at higher doses than the fluid proteases, suggests that the non-canonical nature of this aspartic protease is a significant contributor to efficacy. As the threshold for an effective supplement is high, given the variable size and complex nature of meals, both enzymes will likely be required. When blended at the natural levels that were measured, a high antigen breakdown capacity is preserved, even when the ratio is over 12,000:1 (total protein to fluid enzyme). This represents less than 5 milligrams of enzyme for a 50 grams total daily protein load. With alternative blends and modest increases in dosage, it may be possible to support an effective alternative to a gluten-free diet in the treatment of celiac disease.

```
SEQ ID NO.: 1: Neprosin Amino Acid Sequence
    1       MQAKFFTFVILSSVFYFNYPLAEARSIQARLANKPKGTIKTIKGDDGEVVDCV      53
   54       DIYKQPAFDHPLLKNHTLQMQPSSYASKVGEYNKLEQPWHKNGECPKGSIPIRRQVITGL  113
  114       PVVKKQFPNLKFAPPSANTNHQYAVIAYFYGNASLQGANATINIWEPNLKNPNGDFSLTQ  173
  174       IWISAGSGSSLNTIEAGWQVYPGRTGDSQPRFFIYWTADGYTSTGCYDLTCPGFVQTNNY  233
  234       YAIGMALQPSVYGGQQYELNESIQRDPATGNWWLYLWGTVVGYWPASIYNSITNGADTVE  293
  194       WGGEIYDSSGTGGFHTTTQMGSGHFPTEGYGKASYVRDL                       332
  333       QCVDTYGNVISPTANSFQGIAPAPNCYNYQFQQGSSELYLFYGGPGCQ              380

SEQ ID NO.: 2: Neprosin cDNA Sequence
   1>    ACATGGGGACGGCCTAATTAGTAATCTCAAGTTTGATGTTTAAAA-GGCTTCAACTATGC   >59
  60>    AAGCTAAGTTTTTCACATTTGTTATACTTTCCTCTGTATTTTATTTCAACTATCCTTTGG  >119
 120>    CTGAAGCAAGATCGATTCAAGCAAGATTAGCCAATAAACCAAAGGGTACTATCAAAACCA  >179
 180>    TAAAGGGAGATGATGGAGAGGTGGTTGATTGTGTTGATATATATAAGCAACCAGCTTTTG  >239
 240>    ACCACCCACTTTTAAAAAATCACACTTTACAGATGCAACCCAGTTCATACGCATCCAAGG  >299
 300>    TCGGTGAATACAATAAGCTTGAACAACCATGGCATAAAAATGGTGAGTGCCCTAAAGGTT  >359
 360>    CAATCCCAATTAGAAGGCAAGTTATCACTGGTCTCCCCGTCGTGAAAAACAATTTCCTA   >419
 420>    ACTTGAAATTTGCCCCACCAAGTGCAAATACAAACCACCAGTATGCTGTCATTGCATACT  >479
 480>    TTTACGGCAATGCATCATTGCAAGGAGCAAATGCAACCATTAACATATGGGAGCCCAATT  >539
 540>    TGAAAAACCCTAACGGGGACTTCAGTCTTACTCAAATTTGGATCTCTGCTGGCAGTGGAT  >599
 600>    CCAGCTTGAATACCATTGAGGCAGGATGGCAAGTGTATCCAGGAAGAACAGGTGACTCAC  >659
 660>    AGCCAAGATTTTTCATATATTGGACAGCCGATGGTTATACTTCGACGGGTTGCTATGATT  >719
 720>    TAACATGCCCAGGATTTGTGCAAACTAACAACTATTATGCCATTGGTATGGCGTTACAAC  >779
 780>    CCTCTGTGTACGGCGGACAACAATATGAGTTAAACGAATCCATACAAAGGGACCCAGCGA  >839
 840>    CCGGAAACTGGTGGCTCTACCTGTGGGGACTGTTGTCGGATACTGGCCGGCGTCGATAT   >899
 900>    ACAACTCCATAACTAACGGTGCCGATACCGTAGAATGGGGAGGAGAGATTTACGACTCGT  >959
 960>    CCGGAACCGGTGGATTCCACACGACAACTCAGATGGGAAGCGGTCATTTTCCGACCGAAG >1019
1020>    GTTATGGAAAAGCAAGCTACGTACGTGATCTTCAATGCGTAGATACCTACGGGAATGTCA >1079
1080>    TATCTCCGACGGCGAACAGCTTCCAGGGAATAGCTCCTGCGCCGAATTGTTATAACTATC >1139
1140>    AGTTTCAGCAAGGCAGCTCTGAACTGTATCTCTTTTACGGTGGCCCTGGATGCCAGTGAA >1199
1200>    TGAACTATAATATTGCAGGCCTCTGATAATAAGAGGGGGAGAGAGAGAGAGGGGGGCA    >1259
1260>    GCTGGCTAGCCTATAAATAAGTCCACACAC--TGTAGCTTTGTGTTTCTTTGACAATAAT >1317
1318>    GCAGCGGTCATGAAGGATGTTGAACGCACTAGGGCTTTTTCTTCCGTTCACTTCTGATTT >1377
1378>    GAATGGATCGAGAAGACAGCATTGAACTGTATGACCTAAATTTTTTTCTATTTATTTTGA >1437
1438>    TATCAATGGGNN                                                 >1480
```

Bold: start codon
Underline: stop codon

SEQ ID NO.: 3 Neprosin Predicted Signal Peptide Sequence
QAKFFTFVILSSVFYFNYPLAEA SEQ ID NO.: 4-Nepenthesin I cDNA sequence
ACGTCAAGAACAGCTCTCAATCACCGTCACGAAGCCAAAGTAACGGGCTTTCAGATAATGCTTGAACATGTTGATTC

GGGCAAAAACTTAACCAAATTCCAGCTCTTAGAACGTGCTATCGAAAGGGGTAGTCGTAGATTGCAGAGGCTCGAAG

CCATGTTAAATGGCCCCTCCGGTGTGGAAACTTCCGTCTACGCCGGAGATGGCGAATATCTGATGAACTTATCGATT

GGAACTCCGGCACAACCTTTCTCCGCAATCATGGATACCGGTAGCGATCTTATCTGGACGCAGTGCCAGCCTTGCAC

TCAGTGTTTTAATCAATCAACGCCCATATTTAATCCTCAAGGATCATCCTCCTTCTCCACCCTCCCTTGCTCAAGCC

AACTCTGTCAAGCCCTTTCAAGCCCGACATGCTCTAATAATTTCTGCCAATACACCTACGGGTATGGGGACGGGTCC

GAAACCCAAGGATCCATGGGCACTGAGACTCTCACTTTCGGGTCGGTTTCCATCCCTAATATCACATTCGGCTGCGG

GGAAAACAACCAAGGGTTTGGGCAAGGAAACGGGGCAGGCTTGGTTGGGATGGGTCGGGGCCCTCTGTCGCTTCCTT

CTCAACTCGTCGTGACCAAATTCTCTTACTGCATGACCCCCATTGGTAGCTCAACCCCTAGCACTCTTCTATTGGGA

TCACTGGCTAATTCTGTCACCGCCGGTAGTCCTAATACAACCCTAATCCAAAGCTCTCAAATACCAACTTTCTATTA

TATTACTCTCAACGGGTTGAGTGTTGGTTCAACTCGCTTGCCCATTGATCCGAGTGCTTTTGCACTTAATAGCAATA

ATGGAACAGGAGGGATAATAATAGACTCTGGAACGACACTTACTTACTTCGTTAACGCTTATCAATCTGTAAGGCAA

GAGTTCATCTCCCAGATTAATCTACCCGTCGTAAATGGTTCCTCCTCCGGCTTTGATCTGTGCTTCCAGACGCCTTC

TGATCCGTCAAACCTGCAGATACCCACCTTTGTGATGCATTTTGACGGTGGAGATTTGGAGTTGCCCAGTGAGAATT

ATTTCATCTCCCCAAGCAACGGGCTGATTTGCTTGGCGATGGGGAGTTCGTCGCAGGGGATGTCCATTTTTGGGAAT

ATTCAGCAGCAAAACATGCTAGTCGTTTACGACACCGGAAATTCGGTGGTTTCATTCGCTTCTGCTCAATGTGGTGC

GT

SEQ ID NO.: 14-Nepenthesin II cDNA sequence
ATGGCCTCACCACTATACTCTGTGGTACTTGGCTTAGCAATAGTTTCTGCCATTGTTGCACCAACAAGCTCCACCTC

AAGAGGAACCCTTCTTCATCATGGTCAGAAAAGGCCACAACCCGGCCTTCGTGTTGATCTCGAGCAGGTCGATTCGG

GCAAGAATTTGACCAAATACGAGCTCATCAAACGTGCTATCAAGCGTGGGGAGAGGAGGATGCGAAGCATTAATGCT

ATGTTGCAGAGCTCCTCCGGTATTGAAACTCCTGTTTATGCGGGAGACGGTGAATATCTAATGAACGTAGCAATTGG

TACTCCGGATAGTTCTTTCTCGGCCATTATGGATACCGGCAGTGATCTCATTTGGACGCAATGCGAGCCATGTACGC

AGTGCTTCAGTCAACCTACGCCCATTTTCAACCCACAGGACTCGTCTTCCTTCTCTACCCTTCCTTGCGAGAGCCAG

TATTGCCAAGATCTTCCGAGCGAAACCTGCAATAATAATGAATGCCAATATACATACGGATACGGAGACGGTTCCAC

AACCCAAGGTTATATGGCAACCGAGACCTTCACTTTCGAGACGAGCTCCGTGCCGAATATCGCGTTCGGTTGCGGGG

AAGACAACCAGGGATTCGGGCAAGGCAACGGGGCTGGCCTGATCGGGATGGGTTGGGGCCCGTTATCGCTTCCTTCT

CAACTCGGCGTGGGTCAGTTCTCTTACTGCATGACCTCCTATGGAAGCTCCTCACCCAGCACTCTCGCACTTGGATC

CGCAGCCAGTGGAGTGCCTGAAGGCTCCCCGAGTACGACCCTCATCCATAGTTCTTTGAATCCAACGTACTATTATA

TTACGCTCCAAGGTATAACGGTTGGTGGCGATAATTTGGGTATTCCATCGAGTACTTTTCAACTTCAAGACGATGGA

ACTGGCGGGATGATAATTGACTCCGGGACAACGCTCACTTATCTTCCACAAGACGCTTACAATGCGGTAGCACAAGC

GTTCACTGACCAGATAAATCTCCCCACCGTCGATGAATCCTCGAGCGGCCTCAGTACGTGCTTCCAGCAACCGTCCG

ACGGATCAACCGTGCAAGTTCCGGAGATTTCAATGCAGTTTGATGGTGGGGTGCTGAACTTAGGGGAACAGAATATA

TTGATCTCTCCAGCTGAAGGGGTGATATGCTTGGCGATGGGAAGTTCATCGCAGCTGGGAATTTCCATTTTTGGGAA

TATCCAGCAGCAAGAAACGCAGGTGCTCTATGACCTTCAGAATTTGGCCGTGTCGTTCGTTCCTACTCAGTGTGGTG

CGTCGTAG

-continued

SEQ ID NO.: 15-α-gliadin 33-mer
LQLQPF(PQPQLPY)₃PQPQPF)

SEQ ID NO.: 16-α-gliadin p31-49
LGQQQPFPPQQPYPQPQPF

SEQ ID NO.: 17-Gly-156 from low molecular weight glutenin
QQQQPPFSQQQQSPFSQQQQ

SEQ ID NO.: 18-nonapeptide repeat from high molecular weight glutenin
GYYPTSPQQ

SEQ ID NO.: 19-hexapeptide repeat from high molecular weight glutenin
PGQGQQ

SEQ ID NO.: 20-Nepenthesin II Amino Acid Sequence
QSSSGIETPVYAGDGEYLMNVAIGTPDSSFSAIMDTGSDLIWTQCEPCTQCFSQPTPIFNP
QDSSSFSTLPCESQYCQDLPSETCNNNECQYTYGYDGSTTQGYMATETFTFETSSVPNI
AFGCGEDNQGFGQGNGAGLIGMGWGPLSLPSQLGVGQFSYCMTSYGSSSPSTLALGSA
ASGVPEGSPSTTLIHSSLNPTYYYITLQGITVGGDNLGIPSSTFQLQDDGTGGMTIDSGTTL
TYLPQDAYNAVAQAFTDQINLPTVDESSSGLSTCFQQPSDGSTVQVPEISMQFDGGVLN
LGEQNILISPAEGVICLAMGSSSQLGISIFGNIQQQETQVLYDLQNLAVSFVPTQCGAS SEQ ID NO.: 21-Nepenthesin I Amino Acid Sequence
NGPSGVETSVYAGDGEYLMNLSIGTPAQPFSAIMDTGSDLIWTQCQPCTQCFNQSTPIFN
PQGSSSFSTLPCSSQLCQALSSPTCSNNFCQYTYGYDGSETQGSMGTETLTFGSVSIPNI
TFGCGENNQGFGQGNGAGLVGMGRGPLSLPSQLDVTKFSYCMTPIGSSTPSNLLLGSLA
NSVTAGSPNTTLIQSSQIPTFYYTTLNGLSVGSTRLPIDPSAFALNSNNGTGGIIIDSGTTLT
YFVNNAYQSVRQEFISQINLPVVNGSSSGFDLCFQTPSDPSNLQIPTFVMHFDGGDLELPS
ENYFISPSNGLICLAMGSSSQGMSIFGNIQQQNMLVVYDTGNSVVSFASAQCGAS SEQ ID NO.: 22-Gliadin 33mer Amino Acid Sequence
LQLQPFPQPQLPYPQPQLPYPQPQLPYPQPQPF SEQ ID NO.: 23-LS02R Primer for RACE
GATTACGCCAAGCTTCATTCCCGTTGGGATCTACGCATTG SEQ ID NO.: 24-LS07F Primer for RACE
ACGACAACTCAGATGGGAAGCGG SEQ ID NO.: 25-Nepenthesin 1 Peptide
GPLSLPSQLDVTK SEQ ID NO.: 26-Neprosin Peptide
ASYVR SEQ ID NO.: 27-AQUA Peptide of Antigenic α-gliadin Region
YLQLQPFPQP SEQ ID NO.: 28-AQUA Peptide of Antigenic α-gliadin Region
LQLQPFPQP SEQ ID NO.: 29-AQUA Peptide of Antigenic γ-gliadin Region
QQPYPQQP

What is claimed is:

1. A method for attenuating one or more symptoms of gluten intolerance in a patient in need thereof, which method comprises administering to the patient an effective amount of a pharmaceutical composition comprising neprosin or a variant thereof so as to cleave gluten into non-antigenic peptides, thereby attenuating said symptoms.

2. The method of claim 1, wherein the one or more symptoms are selected from the group consisting of intestinal inflammation, villous atrophy, intraepithelial lymphocytosis.

3. The method of claim 1, wherein the composition comprises neprosin and nepenthesin I and/or nepenthesin II at a ratio of about 1:4 (neprosin:nepenthesin).

4. The method of claim 1, wherein the pharmaceutical composition is orally administered prior to, during, or immediately after consumption of a gluten-containing food.

5. The method of claim 1, wherein the patient suffers from a disease selected from the group consisting of celiac disease, attention deficit hyperactivity disorder, autism, rheumatoid arthritis, fibromyalgia, nutrient malabsorption, and dermatitis herpetiformis.

6. The method of claim 1, wherein the pharmaceutical composition is a sustained-release formulation.

7. The method of claim 1, wherein the pharmaceutical composition comprises an extract of Nepenthes pitcher fluid comprising neprosin.

8. The method of claim 1, wherein the neprosin or variant thereof is a recombinant protein.

9. The method of claim 1, wherein the pharmaceutical composition is between about pH 5 and about pH 8.

10. The method of claim 1, wherein the pharmaceutical composition comprises neprosin.

11. The method of claim 1, wherein the pharmaceutical composition further comprises nepenthesin I or a variant thereof.

12. The method of claim 1, wherein the pharmaceutical composition further comprises nepenthesin II or a variant thereof.

13. The method of claim 1, wherein the pharmaceutical composition further comprises nepenthesin I or a variant thereof and nepenthesin II or a variant thereof.

14. The method of claim 1, wherein the effective amount comprises a total daily protein ingested by the patient to enzyme ratio of between about 1000:1 and about 15000:1.

* * * * *

SEQUENCE LISTING

<160> NUMBER OF SEQ IDS NOS: 94

<210> SEQ ID NO 1
<211> LENGTH: 380
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Met Gln Ala Lys Phe Phe Thr Phe Val Ile Leu Ser Ser Val Phe Tyr
 1               5                  10                  15

Phe Asn Tyr Pro Leu Ala Glu Ala Arg Ser Ile Gln Ala Arg Leu Ala
                20                  25                  30

Asn Lys Pro Lys Gly Thr Ile Lys Thr Ile Lys Gly Asp Asp Gly Glu

```
                35                  40                  45
Val Val Asp Cys Val Asp Ile Tyr Lys Gln Pro Ala Phe Asp His Pro
 50                  55                  60

Leu Leu Lys Asn His Thr Leu Gln Met Gln Pro Ser Ser Tyr Ala Ser
 65                  70                  75                  80

Lys Val Gly Glu Tyr Asn Lys Leu Glu Gln Pro Trp His Lys Asn Gly
                 85                  90                  95

Glu Cys Pro Lys Gly Ser Ile Pro Ile Arg Arg Gln Val Ile Thr Gly
                100                 105                 110

Leu Pro Val Val Lys Lys Gln Phe Pro Asn Leu Lys Phe Ala Pro Pro
                115                 120                 125

Ser Ala Asn Thr Asn His Gln Tyr Ala Val Ile Ala Tyr Phe Tyr Gly
                130                 135                 140

Asn Ala Ser Leu Gln Gly Ala Asn Ala Thr Ile Asn Ile Trp Glu Pro
145                 150                 155                 160

Asn Leu Lys Asn Pro Asn Gly Asp Phe Ser Leu Thr Gln Ile Trp Ile
                165                 170                 175

Ser Ala Gly Ser Gly Ser Ser Leu Asn Thr Ile Glu Ala Gly Trp Gln
                180                 185                 190

Val Tyr Pro Gly Arg Thr Gly Asp Ser Gln Pro Arg Phe Ile Tyr
                195                 200                 205

Trp Thr Ala Asp Gly Tyr Thr Ser Thr Gly Cys Tyr Asp Leu Thr Cys
210                 215                 220

Pro Gly Phe Val Gln Thr Asn Asn Tyr Ala Ile Gly Met Ala Leu
225                 230                 235                 240

Gln Pro Ser Val Tyr Gly Gln Gln Tyr Glu Leu Asn Glu Ser Ile
                245                 250                 255

Gln Arg Asp Pro Ala Thr Gly Asn Trp Trp Leu Tyr Leu Trp Gly Thr
                260                 265                 270

Val Val Gly Tyr Trp Pro Ala Ser Ile Tyr Asn Ser Ile Thr Asn Gly
                275                 280                 285

Ala Asp Thr Val Glu Trp Gly Glu Ile Tyr Asp Ser Ser Gly Thr
290                 295                 300

Gly Gly Phe His Thr Thr Thr Gln Met Gly Ser Gly His Phe Pro Thr
305                 310                 315                 320

Glu Gly Tyr Gly Lys Ala Ser Tyr Val Arg Asp Leu Gln Cys Val Asp
                325                 330                 335

Thr Tyr Gly Asn Val Ile Ser Pro Thr Ala Asn Ser Phe Gln Gly Ile
                340                 345                 350

Ala Pro Ala Pro Asn Cys Tyr Asn Tyr Gln Phe Gln Gln Gly Ser Ser
                355                 360                 365

Glu Leu Tyr Leu Phe Tyr Gly Gly Pro Gly Cys Gln
                370                 375                 380

<210> SEQ ID NO 2
<211> LENGTH: 1480
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1448)..(1449)
<223> OTHER INFORMATION: a, c, t, g, unknown or other

<400> SEQUENCE: 2
```

```
acatggggac ggcctaatta gtaatctcaa gtttgatgtt taaaaggctt caactatgca      60
agctaagttt ttcacatttg ttatactttc ctctgtattt tatttcaact atcctttggc     120
tgaagcaaga tcgattcaag caagattagc caataaacca aagggtacta tcaaaaccat     180
aaagggagat gatggagagg tggttgattg tgttgatata tataagcaac cagcttttga     240
ccacccactt ttaaaaaatc acactttaca gatgcaaccc agttcatacg catccaaggt     300
cggtgaatac aataagcttg aacaaccatg gcataaaaat ggtgagtgcc ctaaaggttc     360
aatcccaatt agaaggcaag ttatcactgg tctccccgtc gtgaaaaaac aatttcctaa     420
cttgaaattt gccccaccaa gtgcaaatac aaaccaccag tatgctgtca ttgcatactt     480
ttacggcaat gcatcattgc aaggagcaaa tgcaaccatt aacatatggg agcccaattt     540
gaaaaaccct aacggggact tcagtcttac tcaaatttgg atctctgctg cagtggatc     600 cagcttgaat accattgagg caggatggca agtgtatcca ggaagaacag gtgactcaca     660
gccaagattt ttcatatatt ggacagccga tggttatact tcgacgggtt gctatgattt     720
aacatgccca ggatttgtgc aaactaacaa ctattatgcc attggtatgg cgttacaacc     780
ctctgtgtac ggcggacaac aatatgagtt aaacgaatcc atacaaaggg acccagcgac     840
cggaaactgg tggctctacc tgtgggggac tgttgtcgga tactggccgg cgtcgatata     900
caactccata actaacggtg ccgataccgt agaatgggga ggagagattt acgactcgtc     960
cggaaccggt ggattccaca cgacaactca gatgggaagc ggtcattttc cgaccgaagg    1020
ttatggaaaa gcaagctacg tacgtgatct tcaatgcgta gatacctacg ggaatgtcat    1080
atctccgacg gcgaacagct tccagggaat agctcctgcg ccgaattgtt ataactatca    1140
gtttcagcaa ggcagctctg aactgtatct cttttacggt ggccctggat gccagtgaat    1200
gaactataat attgcaggcc tctgataata agaggggggag agagagagag aggggggcag    1260
ctggctagcc tataaataag tccacacact gtagctttgt gtttctttga caataatgca    1320
gcggtcatga aggatgttga acgcactagg gcttttctt ccgttcactt ctgatttgaa    1380
tggatcgaga agacagcatt gaactgtatg acctaaattt ttttctattt attttgatat    1440 caatggggnna aaaaaaaaaa aaaaaaaaaa aaaaaaaaa                           1480
```

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ala Lys Phe Phe Thr Phe Val Ile Leu Ser Ser Val Phe Tyr Phe
1               5                   10                  15

Asn Tyr Pro Leu Ala Glu Ala
            20

<210> SEQ ID NO 4
<211> LENGTH: 1234
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
acgtcaagaa cagctctcaa tcaccgtcac gaagccaaag taacgggctt tcagataatg      60
cttgaacatg ttgattcggg caaaaactta accaaattcc agctcttaga acgtgctatc     120
gaaaggggta gtcgtagatt gcagaggctc gaagccatgt taaatggccc ctccggtgtg     180
gaaacttccg tctacgccgg agatggcgaa tatctgatga acttatcgat tggaactccg     240
gcacaacctt tctccgcaat catggatacc ggtagcgatc ttatctggac gcagtgccag     300
ccttgcactc agtgttttaa tcaatcaacg cccatattta atcctcaagg atcatcctcc     360
ttctccaccc tcccttgctc aagccaactc tgtcaagccc tttcaagccc gacatgctct     420
aataatttct gccaatacac ctacgggtat ggggacgggt ccgaaaccca aggatccatg     480
ggcactgaga ctctcacttt cgggtcggtt ccatcccta atatcacatt cggctgcggg      540
gaaaacaacc aagggtttgg gcaaggaaac ggggcaggct tggttgggat gggtcggggc     600
cctctgtcgc ttccttctca actcgtcgtg accaaattct cttactgcat gaccccatt     660 ggtagctcaa cccctagcac tcttctattg ggatcactgg ctaattctgt caccgccggt     720
agtcctaata caaccctaat ccaaagctct caaataccaa ctttctatta tattactctc     780
aacgggttga gtgttggttc aactcgcttg cccattgatc cgagtgcttt tgcacttaat     840
agcaataatg gaacaggagg gataataata gactctggaa cgacacttac ttacttcgtt     900
aacgcttatc aatctgtaag gcaagagttc atctcccaga ttaatctacc cgtcgtaaat     960
ggttcctcct ccggctttga tctgtgcttc cagacgcctt ctgatccgtc aaacctgcag    1020 ataccccacct ttgtgatgca ttttgacggt ggagatttgg agttgccag tgagaattat    1080 ttcatctccc caagcaacgg gctgatttgc ttggcgatgg ggagttcgtc gcaggggatg    1140
tccatttttg ggaatattca gcagcaaaac atgctagtcg tttacgacac cggaaattcg    1200
gtggtttcat tcgcttctgc tcaatgtggt gcgt                                1234
```

<210> SEQ ID NO 5
<211> LENGTH: 437
<212> TYPE: PRT
<213> ORGANISM: Nepenthes mirabilis

<400> SEQUENCE: 5

```
Met Ala Ser Ser Leu Tyr Ser Phe Leu Leu Ala Leu Ser Ile Val Tyr
1               5                  10                  15

Ile Phe Val Ala Pro Thr His Ser Thr Ser Arg Thr Ala Leu Asn His
            20                  25                  30

His His Glu Pro Lys Val Ala Gly Phe Gln Ile Met Leu Glu His Val
        35                  40                  45

Asp Ser Gly Lys Asn Leu Thr Lys Phe Glu Leu Leu Glu Arg Ala Val
    50                  55                  60

Glu Arg Gly Ser Arg Arg Leu Gln Arg Leu Ala Met Leu Asn Gly
65                  70                  75                  80

Pro Ser Gly Val Glu Thr Pro Val Tyr Ala Gly Asp Gly Glu Tyr Leu
                85                  90                  95

Met Asn Leu Ser Ile Gly Thr Pro Ala Gln Pro Phe Ser Ala Ile Met
            100                 105                 110

Asp Thr Gly Ser Asp Leu Ile Trp Thr Gln Cys Gln Pro Cys Thr Gln
        115                 120                 125

Cys Phe Asn Gln Ser Thr Pro Ile Phe Asn Pro Gln Gly Ser Ser Ser
    130                 135                 140

Phe Ser Thr Leu Pro Cys Ser Ser Gln Leu Cys Gln Ala Leu Gln Ser
145                 150                 155                 160
```

```
Pro Thr Cys Ser Asn Asn Ser Cys Gln Tyr Thr Tyr Gly Tyr Gly Asp
                165                 170                 175

Gly Ser Glu Thr Gln Gly Ser Met Gly Thr Glu Thr Leu Thr Phe Gly
            180                 185                 190

Ser Val Ser Ile Pro Asn Ile Thr Phe Gly Cys Gly Glu Asn Asn Gln
        195                 200                 205

Gly Phe Gly Gln Gly Asn Gly Ala Gly Leu Val Gly Met Gly Arg Gly
    210                 215                 220

Pro Leu Ser Leu Pro Ser Gln Leu Asp Val Thr Lys Phe Ser Tyr Cys
225                 230                 235                 240

Met Thr Pro Ile Gly Ser Ser Thr Ser Ser Thr Leu Leu Leu Gly Ser
                245                 250                 255

Leu Ala Asn Ser Val Thr Ala Gly Ser Pro Asn Thr Thr Leu Ile Glu
            260                 265                 270

Ser Ser Gln Ile Pro Thr Phe Tyr Tyr Ile Thr Leu Asn Gly Leu Ser
        275                 280                 285

Val Gly Ser Thr Pro Leu Pro Ile Asp Pro Ser Val Phe Lys Leu Asn
    290                 295                 300

Ser Asn Asn Gly Thr Gly Gly Ile Ile Ile Asp Ser Gly Thr Thr Leu
305                 310                 315                 320

Thr Tyr Phe Ala Asp Asn Ala Tyr Gln Ala Val Arg Gln Ala Phe Ile
                325                 330                 335

Ser Gln Met Asn Leu Ser Val Val Asn Gly Ser Ser Ser Gly Phe Asp
            340                 345                 350

Leu Cys Phe Gln Met Pro Ser Asp Gln Ser Asn Leu Gln Ile Pro Thr
        355                 360                 365

Phe Val Met His Phe Asp Gly Gly Asp Leu Val Leu Pro Ser Glu Asn
    370                 375                 380

Tyr Phe Ile Ser Pro Ser Asn Gly Leu Ile Cys Leu Ala Met Gly Ser
385                 390                 395                 400

Ser Ser Gln Gly Met Ser Ile Phe Gly Asn Ile Gln Gln Gln Asn Leu
                405                 410                 415

Leu Val Val Tyr Asp Thr Gly Asn Ser Val Val Ser Phe Leu Phe Ala
            420                 425                 430

Gln Cys Gly Ala Ser
        435

<210> SEQ ID NO 6
<211> LENGTH: 437
<212> TYPE: PRT
<213> ORGANISM: Nepenthes alata

<400> SEQUENCE: 6

Met Ala Ser Ser Leu Tyr Ser Phe Leu Leu Ala Leu Ser Ile Val Tyr
1               5                   10                  15

Ile Phe Val Ala Pro Thr His Ser Thr Ser Arg Thr Ala Leu Asn His
                20                  25                  30

His His Glu Pro Lys Val Ala Gly Phe Gln Ile Met Leu Glu His Val
            35                  40                  45

Asp Ser Gly Lys Asn Leu Thr Lys Phe Glu Leu Glu Arg Ala Val
        50                  55                  60

Glu Arg Gly Ser Arg Arg Leu Gln Arg Leu Glu Ala Met Leu Asn Gly
65                  70                  75                  80

Pro Ser Gly Val Glu Thr Pro Val Tyr Ala Gly Asp Gly Glu Tyr Leu
```

```
                                85                  90                  95
Met Asn Leu Ser Ile Gly Thr Pro Ala Gln Pro Phe Ser Ala Ile Met
                100                 105                 110

Asp Thr Gly Ser Asp Leu Ile Trp Thr Gln Cys Gln Pro Cys Thr Gln
            115                 120                 125

Cys Phe Asn Gln Ser Thr Pro Ile Phe Asn Pro Gln Gly Ser Ser Ser
        130                 135                 140

Phe Ser Thr Leu Pro Cys Ser Ser Gln Leu Cys Gln Ala Leu Gln Ser
145                 150                 155                 160

Pro Thr Cys Ser Asn Asn Ser Cys Gln Tyr Thr Tyr Gly Tyr Gly Asp
                165                 170                 175

Gly Ser Glu Thr Gln Gly Ser Met Gly Thr Glu Thr Leu Thr Phe Gly
            180                 185                 190

Ser Val Ser Ile Pro Asn Ile Thr Phe Gly Cys Gly Glu Asn Asn Gln
        195                 200                 205

Gly Phe Gly Gln Gly Asn Gly Ala Gly Leu Val Gly Met Gly Arg Gly
    210                 215                 220

Pro Leu Ser Leu Pro Ser Gln Leu Asp Val Thr Lys Phe Ser Tyr Cys
225                 230                 235                 240

Met Thr Pro Ile Gly Ser Ser Asn Ser Ser Thr Leu Leu Leu Gly Ser
                245                 250                 255

Leu Ala Asn Ser Val Thr Ala Gly Ser Pro Asn Thr Thr Leu Ile Gln
            260                 265                 270

Ser Ser Gln Ile Pro Thr Phe Tyr Tyr Ile Thr Leu Asn Gly Leu Ser
        275                 280                 285

Val Gly Ser Thr Pro Leu Pro Ile Asp Pro Ser Val Phe Lys Leu Asn
    290                 295                 300

Ser Asn Asn Gly Thr Gly Gly Ile Ile Ile Asp Ser Gly Thr Thr Leu
305                 310                 315                 320

Thr Tyr Phe Val Asp Asn Ala Tyr Gln Ala Val Arg Gln Ala Phe Ile
                325                 330                 335

Ser Gln Met Asn Leu Ser Val Val Asn Gly Ser Ser Ser Gly Phe Asp
            340                 345                 350

Leu Cys Phe Gln Met Pro Ser Asp Gln Ser Asn Leu Gln Ile Pro Thr
        355                 360                 365

Phe Val Met His Phe Asp Gly Gly Asp Leu Val Leu Pro Ser Glu Asn
    370                 375                 380

Tyr Phe Ile Ser Pro Ser Asn Gly Leu Ile Cys Leu Ala Met Gly Ser
385                 390                 395                 400

Ser Ser Gln Gly Met Ser Ile Phe Gly Asn Ile Gln Gln Asn Leu
                405                 410                 415

Leu Val Val Tyr Asp Thr Gly Asn Ser Val Val Ser Phe Leu Ser Ala
            420                 425                 430

Gln Cys Gly Ala Ser
        435

<210> SEQ ID NO 7
<211> LENGTH: 437
<212> TYPE: PRT
<213> ORGANISM: Nepenthes gracilis

<400> SEQUENCE: 7

Met Ala Ser Ser Leu Tyr Ser Phe Leu Leu Ala Leu Ser Ile Val Tyr
1               5                   10                  15
```

```
Ile Phe Val Ala Pro Thr His Ser Thr Ser Arg Thr Ala Leu Asn His
             20                  25                  30
Arg His Glu Ala Lys Val Thr Gly Phe Gln Ile Met Leu Glu His Val
         35                  40                  45
Asp Ser Gly Lys Asn Leu Thr Lys Phe Gln Leu Leu Glu Arg Ala Ile
     50                  55                  60
Glu Arg Gly Ser Arg Arg Leu Gln Arg Leu Glu Ala Met Leu Asn Gly
 65                  70                  75                  80
Pro Ser Gly Val Glu Thr Ser Val Tyr Ala Gly Asp Gly Glu Tyr Leu
                 85                  90                  95
Met Asn Leu Ser Ile Gly Thr Pro Ala Gln Pro Phe Ser Ala Ile Met
             100                 105                 110
Asp Thr Gly Ser Asp Leu Ile Trp Thr Gln Cys Gln Pro Cys Thr Gln
         115                 120                 125
Cys Phe Asn Gln Ser Thr Pro Ile Phe Asn Pro Gln Gly Ser Ser Ser
     130                 135                 140
Phe Ser Thr Leu Pro Cys Ser Ser Gln Leu Cys Gln Ala Leu Ser Ser
145                 150                 155                 160
Pro Thr Cys Ser Asn Asn Phe Cys Gln Tyr Thr Tyr Gly Tyr Gly Asp
                 165                 170                 175
Gly Ser Glu Thr Gln Gly Ser Met Gly Thr Glu Thr Leu Thr Phe Gly
             180                 185                 190
Ser Val Ser Ile Pro Asn Ile Thr Phe Gly Cys Gly Glu Asn Asn Gln
         195                 200                 205
Gly Phe Gly Gln Gly Asn Gly Ala Gly Leu Val Gly Met Gly Arg Gly
     210                 215                 220
Pro Leu Ser Leu Pro Ser Gln Leu Asp Val Thr Lys Phe Ser Tyr Cys
225                 230                 235                 240
Met Thr Pro Ile Gly Ser Ser Thr Pro Ser Asn Leu Leu Leu Gly Ser
                 245                 250                 255
Leu Ala Asn Ser Val Thr Ala Gly Ser Pro Asn Thr Thr Leu Ile Gln
             260                 265                 270
Ser Ser Gln Ile Pro Thr Phe Tyr Tyr Ile Thr Leu Asn Gly Leu Ser
         275                 280                 285
Val Gly Ser Thr Arg Leu Pro Ile Asp Pro Ser Ala Phe Ala Leu Asn
     290                 295                 300
Ser Asn Asn Gly Thr Gly Gly Ile Ile Ile Asp Ser Gly Thr Thr Leu
305                 310                 315                 320
Thr Tyr Phe Val Asn Asn Ala Tyr Gln Ser Val Arg Gln Glu Phe Ile
                 325                 330                 335
Ser Gln Ile Asn Leu Pro Val Val Asn Gly Ser Ser Ser Gly Phe Asp
             340                 345                 350
Leu Cys Phe Gln Thr Pro Ser Asp Pro Ser Asn Leu Gln Ile Pro Thr
         355                 360                 365
Phe Val Met His Phe Asp Gly Gly Asp Leu Glu Leu Pro Ser Glu Asn
     370                 375                 380
Tyr Phe Ile Ser Pro Ser Asn Gly Leu Ile Cys Leu Ala Met Gly Ser
385                 390                 395                 400
Ser Ser Gln Gly Met Ser Ile Phe Gly Asn Ile Gln Gln Asn Met
                 405                 410                 415
Leu Val Val Tyr Asp Thr Gly Asn Ser Val Val Ser Phe Ala Ser Ala
             420                 425                 430
Gln Cys Gly Ala Ser
```

435

<210> SEQ ID NO 8
<211> LENGTH: 437
<212> TYPE: PRT
<213> ORGANISM: Nepenthes mirabilis

<400> SEQUENCE: 8

```
Met Ala Ser Pro Leu His Ser Val Val Leu Gly Leu Ala Ile Val Ser
1               5                   10                  15

Ala Ile Val Ala Pro Thr Ser Thr Ser Arg Gly Thr Leu Leu His
            20                  25                  30

His Gly Gln Lys Arg Pro Gln Pro Gly Leu Arg Val Val Leu Glu Gln
        35                  40                  45

Val Asp Ser Gly Met Asn Leu Thr Lys Tyr Glu Leu Ile Lys Arg Ala
    50                  55                  60

Ile Lys Arg Gly Glu Arg Arg Met Arg Ser Ile Asn Ala Met Leu Gln
65                  70                  75                  80

Ser Ser Ser Gly Ile Glu Thr Pro Val Tyr Ala Gly Ser Gly Glu Tyr
                85                  90                  95

Leu Met Asn Val Ala Ile Gly Thr Pro Ala Ser Ser Leu Ser Ala Ile
            100                 105                 110

Met Asp Thr Gly Ser Asp Leu Ile Trp Thr Gln Cys Glu Pro Cys Thr
        115                 120                 125

Gln Cys Phe Ser Gln Pro Thr Pro Ile Phe Asn Pro Gln Asp Ser Ser
130                 135                 140

Ser Phe Ser Thr Leu Pro Cys Glu Ser Gln Tyr Cys Gln Asp Leu Pro
145                 150                 155                 160

Ser Glu Ser Cys Tyr Asn Asp Cys Gln Tyr Thr Tyr Gly Tyr Gly Asp
                165                 170                 175

Gly Ser Ser Thr Gln Gly Tyr Met Ala Thr Glu Thr Phe Thr Phe Glu
            180                 185                 190

Thr Ser Ser Val Pro Asn Ile Ala Phe Gly Cys Gly Glu Asp Asn Gln
        195                 200                 205

Gly Phe Gly Gln Gly Asn Gly Ala Gly Leu Ile Gly Met Gly Trp Gly
210                 215                 220

Pro Leu Ser Leu Pro Ser Gln Leu Gly Val Gly Gln Phe Ser Tyr Cys
225                 230                 235                 240

Met Thr Ser Ser Gly Ser Ser Pro Ser Thr Leu Ala Leu Gly Ser
                245                 250                 255

Ala Ala Ser Gly Val Pro Glu Gly Ser Pro Ser Thr Thr Leu Ile His
            260                 265                 270

Ser Ser Leu Asn Pro Thr Tyr Tyr Tyr Ile Thr Leu Gln Gly Ile Thr
        275                 280                 285

Val Gly Gly Asp Asn Leu Gly Ile Pro Ser Ser Thr Phe Gln Leu Gln
    290                 295                 300

Asp Asp Gly Thr Gly Gly Met Ile Ile Asp Ser Gly Thr Thr Leu Thr
305                 310                 315                 320

Tyr Leu Pro Gln Asp Ala Tyr Asn Ala Val Ala Gln Ala Phe Thr Asp
                325                 330                 335

Gln Ile Asn Leu Ser Pro Val Asp Glu Ser Ser Gly Leu Ser Thr
            340                 345                 350

Cys Phe Gln Leu Pro Ser Asp Gly Ser Thr Val Gln Val Pro Glu Ile
        355                 360                 365
```

-continued

```
Ser Met Gln Phe Asp Gly Gly Val Leu Asn Leu Gly Glu Glu Asn Val
    370                 375                 380

Leu Ile Ser Pro Ala Glu Gly Val Ile Cys Leu Ala Met Gly Ser Ser
385                 390                 395                 400

Ser Gln Gln Gly Ile Ser Ile Phe Gly Asn Ile Gln Gln Gln Glu Thr
                405                 410                 415

Gln Val Leu Tyr Asp Leu Gln Asn Leu Ala Val Ser Phe Val Pro Thr
            420                 425                 430

Gln Cys Gly Ala Ser
            435

<210> SEQ ID NO 9
<211> LENGTH: 438
<212> TYPE: PRT
<213> ORGANISM: Nepenthes gracilis

<400> SEQUENCE: 9

Met Ala Ser Pro Leu Tyr Ser Val Val Gly Leu Ala Ile Val Ser
1               5                   10                  15

Ala Ile Val Ala Pro Thr Ser Ser Ser Arg Gly Thr Leu Leu His
            20                  25                  30

His Gly Gln Lys Arg Pro Gln Pro Gly Leu Arg Val Asp Leu Glu Gln
        35                  40                  45

Val Asp Ser Gly Lys Asn Leu Thr Lys Tyr Glu Leu Ile Lys Arg Ala
50                  55                  60

Ile Lys Arg Gly Glu Arg Arg Met Arg Ser Ile Asn Ala Met Leu Gln
65                  70                  75                  80

Ser Ser Ser Gly Ile Glu Thr Pro Val Tyr Ala Gly Asp Gly Glu Tyr
                85                  90                  95

Leu Met Asn Val Ala Ile Gly Thr Pro Asp Ser Phe Ser Ala Ile
            100                 105                 110

Met Asp Thr Gly Ser Asp Leu Ile Trp Thr Gln Cys Glu Pro Cys Thr
        115                 120                 125

Gln Cys Phe Ser Gln Pro Thr Pro Ile Phe Asn Pro Gln Asp Ser Ser
130                 135                 140

Ser Phe Ser Thr Leu Pro Cys Glu Ser Gln Tyr Cys Gln Asp Leu Pro
145                 150                 155                 160

Ser Glu Thr Cys Asn Asn Asn Glu Cys Gln Tyr Thr Tyr Gly Tyr Gly
                165                 170                 175

Asp Gly Ser Thr Thr Gln Gly Tyr Met Ala Thr Glu Thr Phe Thr Phe
            180                 185                 190

Glu Thr Ser Ser Val Pro Asn Ile Ala Phe Gly Cys Gly Glu Asp Asn
        195                 200                 205

Gln Gly Phe Gly Gln Gly Asn Gly Ala Gly Leu Ile Gly Met Gly Trp
210                 215                 220

Gly Pro Leu Ser Leu Pro Ser Gln Leu Gly Val Gly Gln Phe Ser Tyr
225                 230                 235                 240

Cys Met Thr Ser Tyr Gly Ser Ser Pro Ser Thr Leu Ala Leu Gly
                245                 250                 255

Ser Ala Ala Ser Gly Val Pro Glu Gly Ser Pro Ser Thr Thr Leu Ile
            260                 265                 270

His Ser Ser Leu Asn Pro Thr Tyr Tyr Tyr Ile Thr Leu Gln Gly Ile
        275                 280                 285

Thr Val Gly Gly Asp Asn Leu Gly Ile Pro Ser Ser Thr Phe Gln Leu
290                 295                 300
```

-continued

Gln Asp Asp Gly Thr Gly Gly Met Ile Ile Asp Ser Gly Thr Thr Leu
305                 310                 315                 320

Thr Tyr Leu Pro Gln Asp Ala Tyr Asn Ala Val Ala Gln Ala Phe Thr
            325                 330                 335

Asp Gln Ile Asn Leu Pro Thr Val Asp Glu Ser Ser Ser Gly Leu Ser
        340                 345                 350

Thr Cys Phe Gln Gln Pro Ser Asp Gly Ser Thr Val Gln Val Pro Glu
    355                 360                 365

Ile Ser Met Gln Phe Asp Gly Val Leu Asn Leu Gly Glu Gln Asn
370                 375                 380

Ile Leu Ile Ser Pro Ala Glu Gly Val Ile Cys Leu Ala Met Gly Ser
385                 390                 395                 400

Ser Ser Gln Leu Gly Ile Ser Ile Phe Gly Asn Ile Gln Gln Gln Glu
                405                 410                 415

Thr Gln Val Leu Tyr Asp Leu Gln Asn Leu Ala Val Ser Phe Val Pro
            420                 425                 430

Thr Gln Cys Gly Ala Ser
        435

<210> SEQ ID NO 10
<211> LENGTH: 472
<212> TYPE: PRT
<213> ORGANISM: Zea mays

<400> SEQUENCE: 10

Met Ala Phe His Ser Cys Thr Ile Ile Pro Ala Ser His His Ser Ser
1               5                   10                  15

Met Ser Ser Ser Thr Ser Gln Met Ala Ser Leu Ala Val Leu Val Phe
            20                  25                  30

Leu Val Val Cys Ala Thr Leu Ala Ser Gly Ala Ala Ser Val Arg Val
        35                  40                  45

Gly Leu Thr Arg Ile His Ser Asp Pro Asp Thr Ala Pro Gln Phe
50                  55                  60

Val Arg Asp Ala Leu Arg Arg Asp Met His Arg Gln Arg Ser Arg Ser
65                  70                  75                  80

Phe Gly Arg Asp Arg Asp Arg Glu Leu Ala Glu Ser Asp Gly Arg Thr
                85                  90                  95

Ser Thr Thr Val Ser Ala Arg Thr Arg Lys Asp Leu Pro Asn Gly Gly
            100                 105                 110

Glu Tyr Leu Met Thr Leu Ala Ile Gly Thr Pro Pro Leu Pro Tyr Ala
        115                 120                 125

Ala Val Ala Asp Thr Gly Ser Asp Leu Ile Trp Thr Gln Cys Ala Pro
    130                 135                 140

Cys Gly Thr Gln Cys Phe Glu Gln Pro Ala Pro Leu Tyr Asn Pro Ala
145                 150                 155                 160

Ser Ser Thr Thr Phe Ser Val Leu Pro Cys Asn Ser Ser Leu Ser Met
                165                 170                 175

Cys Ala Gly Ala Leu Ala Gly Ala Ala Pro Pro Gly Cys Ala Cys
            180                 185                 190

Met Tyr Tyr Gln Thr Tyr Gly Thr Gly Trp Thr Ala Gly Val Gln Gly
        195                 200                 205

Ser Glu Thr Phe Thr Phe Gly Ser Ser Ala Ala Asp Gln Ala Arg Val
    210                 215                 220

Pro Gly Val Ala Phe Gly Cys Ser Asn Ala Ser Ser Ser Asp Trp Asn

```
                225                 230                 235                 240
Gly Ser Ala Gly Leu Val Gly Leu Gly Arg Gly Ser Leu Ser Leu Val
            245                 250                 255

Ser Gln Leu Gly Ala Gly Arg Phe Ser Tyr Cys Leu Thr Pro Phe Gln
            260                 265                 270

Asp Thr Asn Ser Thr Ser Thr Leu Leu Gly Pro Ser Ala Ala Leu
            275                 280                 285

Asn Gly Thr Gly Val Arg Ser Thr Pro Phe Val Ala Ser Pro Ala Arg
            290                 295                 300

Ala Pro Met Ser Thr Tyr Tyr Leu Asn Leu Thr Gly Ile Ser Leu
305                 310                 315                 320

Gly Ala Lys Ala Leu Pro Ile Ser Pro Gly Ala Phe Ser Leu Lys Pro
            325                 330                 335

Asp Gly Thr Gly Gly Leu Ile Ile Asp Ser Gly Thr Thr Ile Thr Ser
            340                 345                 350

Leu Ala Asn Ala Ala Tyr Gln Gln Val Arg Ala Ala Val Lys Ser Gln
            355                 360                 365

Leu Val Thr Thr Leu Pro Thr Val Asp Gly Ser Asp Ser Thr Gly Leu
            370                 375                 380

Asp Leu Cys Phe Ala Leu Pro Ala Pro Thr Ser Ala Pro Pro Ala Val
385                 390                 395                 400

Leu Pro Ser Met Thr Leu His Phe Asp Gly Ala Asp Met Val Leu Pro
            405                 410                 415

Ala Asp Ser Tyr Met Ile Ser Gly Ser Gly Val Trp Cys Leu Ala Met
            420                 425                 430

Arg Asn Gln Thr Asp Gly Ala Met Ser Thr Phe Gly Asn Tyr Gln Gln
            435                 440                 445

Gln Asn Met His Ile Leu Tyr Asp Val Arg Glu Glu Thr Leu Ser Phe
            450                 455                 460

Ala Pro Ala Lys Cys Ser Thr Leu
465                 470

<210> SEQ ID NO 11
<211> LENGTH: 453
<212> TYPE: PRT
<213> ORGANISM: Oryza sativa

<400> SEQUENCE: 11

Met Arg Gly Val Ser Val Val Leu Val Leu Ile Ala Cys Trp Leu Cys
1               5                   10                  15

Gly Cys Pro Val Ala Gly Glu Ala Ala Phe Ala Gly Asp Ile Arg Val
            20                  25                  30

Asp Leu Thr His Val Asp Ala Gly Lys Glu Leu Pro Lys Arg Glu Leu
            35                  40                  45

Ile Arg Arg Ala Met Gln Arg Ser Lys Ala Arg Ala Ala Ala Leu Ser
        50                  55                  60

Val Val Arg Asn Gly Gly Phe Tyr Gly Ser Ile Ala Gln Ala Arg
65                  70                  75                  80

Glu Arg Glu Arg Glu Pro Gly Met Ala Val Arg Ala Ser Gly Asp Leu
            85                  90                  95

Glu Tyr Val Leu Asp Leu Ala Val Gly Thr Pro Pro Gln Pro Ile Thr
            100                 105                 110

Ala Leu Leu Asp Thr Gly Ser Asp Leu Ile Trp Thr Gln Cys Asp Thr
            115                 120                 125
```

```
Cys Thr Ala Cys Leu Arg Gln Pro Asp Pro Leu Phe Ser Pro Arg Met
    130                 135                 140

Ser Ser Ser Tyr Glu Pro Met Arg Cys Ala Gly Gln Leu Cys Gly Asp
145                 150                 155                 160

Ile Leu His His Ser Cys Val Arg Pro Asp Thr Cys Thr Tyr Arg Tyr
                165                 170                 175

Ser Tyr Gly Asp Gly Thr Thr Leu Gly Tyr Tyr Ala Thr Glu Arg
            180                 185                 190

Phe Thr Phe Ala Ser Ser Ser Gly Glu Thr Gln Ser Val Pro Leu Gly
        195                 200                 205

Phe Gly Cys Gly Thr Met Asn Val Gly Ser Leu Asn Asn Ala Ser Gly
    210                 215                 220

Ile Val Gly Phe Gly Arg Asp Pro Leu Ser Leu Val Ser Gln Leu Ser
225                 230                 235                 240

Ile Arg Arg Phe Ser Tyr Cys Leu Thr Pro Tyr Ala Ser Ser Arg Lys
                245                 250                 255

Ser Thr Leu Gln Phe Gly Ser Leu Ala Asp Val Gly Leu Tyr Asp Asp
            260                 265                 270

Ala Thr Gly Pro Val Gln Thr Thr Pro Ile Leu Gln Ser Ala Gln Asn
        275                 280                 285

Pro Thr Phe Tyr Tyr Val Ala Phe Thr Gly Val Thr Val Gly Ala Arg
    290                 295                 300

Arg Leu Arg Ile Pro Ala Ser Ala Phe Ala Leu Arg Pro Asp Gly Ser
305                 310                 315                 320

Gly Gly Val Ile Ile Asp Ser Gly Thr Ala Leu Thr Leu Phe Pro Val
                325                 330                 335

Ala Val Leu Ala Glu Val Val Arg Ala Phe Arg Ser Gln Leu Arg Leu
            340                 345                 350

Pro Phe Ala Asn Gly Ser Ser Pro Asp Asp Gly Val Cys Phe Ala Ala
        355                 360                 365

Pro Ala Val Ala Ala Gly Gly Gly Arg Met Ala Arg Gln Val Ala Val
    370                 375                 380

Pro Arg Met Val Phe His Phe Gln Gly Ala Asp Leu Asp Leu Pro Arg
385                 390                 395                 400

Glu Asn Tyr Val Leu Glu Asp His Arg Gly His Leu Cys Val Leu
                405                 410                 415

Leu Gly Asp Ser Gly Asp Asp Gly Ala Thr Ile Gly Asn Phe Val Gln
            420                 425                 430

Gln Asp Met Arg Val Val Tyr Asp Leu Glu Arg Glu Thr Leu Ser Phe
        435                 440                 445

Ala Pro Val Glu Cys
    450

<210> SEQ ID NO 12
<211> LENGTH: 486
<212> TYPE: PRT
<213> ORGANISM: Oryza sativa

<400> SEQUENCE: 12

Met Ala Asp Arg Ile Thr Val Leu Ala Ile Ala Leu Leu Val Leu Ile
1               5                   10                  15

Leu Ser Pro Gln Met Ala Val Gln Gly Lys Pro Ala Ala Gly Asn Thr
            20                  25                  30

Ala Ser Pro Arg Pro Lys Gln Gln Gln Leu Gly Asn Phe Phe Lys Lys
        35                  40                  45
```

```
His Gly Ser Asp Ile Ala Gly Leu Phe Pro Arg His Arg Asn Gly Gly
     50                  55                  60

Ser Ser Gly Ser Tyr Ser Gly Gln Ala Val Pro Ala Asp Gly Gly Glu
 65                  70                  75                  80

Asn Gly Gly Gly Gln Ser Gln Asp Pro Ala Thr Asn Thr Gly Met
                 85                  90                  95

Tyr Val Leu Ser Phe Ser Val Gly Thr Pro Pro Gln Val Val Thr Gly
                100                 105                 110

Val Leu Asp Ile Thr Ser Asp Phe Val Trp Met Gln Cys Ser Ala Cys
            115                 120                 125

Ala Thr Cys Gly Ala Asp Ala Pro Ala Thr Ser Ala Pro Pro Phe
            130                 135                 140

Tyr Ala Phe Leu Ser Ser Thr Ile Arg Glu Val Arg Cys Ala Asn Arg
145                 150                 155                 160

Gly Cys Gln Arg Leu Val Pro Gln Thr Cys Ser Ala Asp Asp Ser Pro
                165                 170                 175

Cys Gly Tyr Ser Tyr Val Tyr Gly Gly Ala Ala Asn Thr Thr Ala
                180                 185                 190

Gly Leu Leu Ala Val Asp Ala Phe Ala Phe Ala Thr Val Arg Ala Asp
            195                 200                 205

Gly Val Ile Phe Gly Cys Ala Val Ala Thr Glu Gly Asp Ile Gly Gly
            210                 215                 220

Val Ile Gly Leu Gly Arg Gly Glu Leu Ser Pro Val Ser Gln Leu Gln
225                 230                 235                 240

Ile Gly Arg Phe Ser Tyr Tyr Leu Ala Pro Asp Ala Val Asp Val
                245                 250                 255

Gly Ser Phe Ile Leu Phe Leu Asp Asp Ala Lys Pro Arg Thr Ser Arg
                260                 265                 270

Ala Val Ser Thr Pro Leu Val Ala Ser Arg Ala Ser Arg Ser Leu Tyr
            275                 280                 285

Tyr Val Glu Leu Ala Gly Ile Arg Val Asp Gly Glu Asp Leu Ala Ile
            290                 295                 300

Pro Arg Gly Thr Phe Asp Leu Gln Ala Asp Gly Ser Gly Gly Val Val
305                 310                 315                 320

Leu Ser Ile Thr Ile Pro Val Thr Phe Leu Asp Ala Gly Ala Tyr Lys
                325                 330                 335

Val Val Arg Gln Ala Met Ala Ser Lys Ile Glu Leu Arg Ala Ala Asp
            340                 345                 350

Gly Ser Glu Leu Gly Leu Asp Leu Cys Tyr Thr Ser Glu Ser Leu Ala
            355                 360                 365

Thr Ala Lys Val Pro Ser Met Ala Leu Val Phe Ala Gly Gly Ala Val
            370                 375                 380

Met Glu Leu Glu Met Gly Asn Tyr Phe Tyr Met Asp Ser Thr Thr Gly
385                 390                 395                 400

Leu Glu Cys Leu Thr Ile Leu Pro Ser Pro Ala Gly Asp Gly Ser Leu
                405                 410                 415

Leu Gly Ser Leu Ile Gln Val Gly Thr His Met Ile Tyr Asp Ile Ser
                420                 425                 430

Gly Ser Arg Leu Val Phe Glu Ser Leu Glu Gln Ala Pro Pro Pro
            435                 440                 445

Ser Gly Ser Ser Arg Gln Ser Arg Arg Arg Ser Ser Ala Pro
450                 455                 460
```

```
Pro Pro Leu Thr Ser Pro Ala Val Val Ile His Leu Met Leu Val
465                 470                 475                 480

Val Val Tyr Met Phe Leu
            485

<210> SEQ ID NO 13
<211> LENGTH: 471
<212> TYPE: PRT
<213> ORGANISM: Zea mays

<400> SEQUENCE: 13

Met Ala Met Met Ala Cys Asn Asn Thr Arg Pro Arg Lys Leu Ser Leu
1               5                   10                  15

Pro Cys Arg Thr Arg Thr Phe Gln Ala Leu Ile Leu Ser Thr Ala Val
            20                  25                  30

Phe Leu Ala Ala Ser Thr Ala Val Val Gly Lys Glu Pro Gln Pro
        35                  40                  45

Pro Ser Ser Ser Gly Gly Gly Cys His Tyr Arg Phe Glu Leu Thr His
    50                  55                  60

Val Asp Ala Asn Leu Asn Leu Thr Ser Asp Glu Leu Met Arg Arg Ala
65                  70                  75                  80

Tyr Asp Arg Ser Arg Leu Arg Ala Ala Ser Leu Ala Ala Tyr Ser Asp
                85                  90                  95

Gly Arg His Glu Gly Arg Val Ser Ile Pro Asp Ala Ser Tyr Ile Ile
            100                 105                 110

Thr Phe Tyr Leu Gly Asn Gln Arg Pro Glu Asp Asn Ile Ser Ala Val
        115                 120                 125

Val Asp Thr Gly Ser Asp Ile Phe Trp Thr Thr Glu Lys Glu Cys Ser
130                 135                 140

Arg Ser Lys Thr Arg Ser Met Leu Pro Cys Cys Ser Pro Lys Cys Glu
145                 150                 155                 160

Gln Arg Ala Ser Cys Gly Cys Gly Arg Ser Glu Leu Lys Ala Glu Ala
                165                 170                 175

Glu Lys Glu Thr Lys Cys Thr Tyr Ala Ile Ile Tyr Gly Gly Asn Ala
            180                 185                 190

Asn Asp Ser Thr Ala Gly Val Met Tyr Glu Asp Lys Leu Thr Ile Val
        195                 200                 205

Ala Val Ala Ser Lys Ala Val Pro Ser Ser Gln Ser Phe Lys Glu Val
210                 215                 220

Ala Ile Gly Cys Ser Thr Ser Ala Thr Leu Lys Phe Lys Asp Pro Ser
225                 230                 235                 240

Ile Lys Gly Val Phe Gly Leu Gly Arg Ser Ala Thr Ser Leu Pro Arg
                245                 250                 255

Gln Leu Asn Phe Ser Lys Phe Ser Tyr Cys Leu Ser Ser Tyr Gln Glu
            260                 265                 270

Pro Asp Leu Pro Ser Tyr Leu Leu Leu Thr Ala Ala Pro Asp Met Ala
        275                 280                 285

Thr Gly Ala Val Gly Gly Ala Ala Val Ala Thr Thr Ala Leu Gln
290                 295                 300

Pro Asn Ser Asp Tyr Lys Thr Leu Tyr Phe Val His Leu Gln Asn Ile
305                 310                 315                 320

Ser Ile Gly Gly Thr Arg Phe Pro Ala Val Ser Thr Lys Ser Gly Gly
                325                 330                 335

Asn Met Phe Val Asp Thr Gly Ala Ser Phe Thr Arg Leu Glu Gly Thr
            340                 345                 350
```

```
Val Phe Ala Lys Leu Val Thr Glu Leu Asp Arg Ile Met Lys Glu Arg
            355                 360                 365

Lys Tyr Val Lys Glu Gln Pro Gly Arg Asn Asn Gly Gln Ile Cys Tyr
    370                 375                 380

Ser Pro Pro Ser Thr Ala Ala Asp Glu Ser Ser Lys Leu Pro Asp Met
385                 390                 395                 400

Val Leu His Phe Ala Asp Ser Ala Asn Met Val Leu Pro Trp Asp Ser
                405                 410                 415

Tyr Leu Trp Lys Thr Thr Ser Lys Leu Cys Leu Ala Ile Tyr Lys Ser
            420                 425                 430

Asn Ile Lys Gly Gly Ile Ser Val Leu Gly Asn Phe Gln Met Gln Asn
            435                 440                 445

Thr His Met Leu Leu Asp Thr Gly Asn Glu Lys Leu Ser Phe Val Arg
    450                 455                 460

Ala Asp Cys Ser Lys Val Ile
465                 470

<210> SEQ ID NO 14
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atggcctcac cactatactc tgtggtactt ggcttagcaa tagtttctgc cattgttgca      60
ccaacaagct ccacctcaag aggaaccctt cttcatcatg gtcagaaaag gccacaaccc     120
ggccttcgtg ttgatctcga gcaggtcgat tcgggcaaga atttgaccaa atacgagctc     180
atcaaacgtg ctatcaagcg tggggagagg aggatgcgaa gcattaatgc tatgttgcag     240
agctcctccg gtattgaaac tcctgtttat gcggagacg tgaatatct aatgaacgta      300 gcaattggta ctccggatag ttcttttctcg gccattatgg ataccggcag tgatctcatt     360
tggacgcaat gcgagccatg tacgcagtgc ttcagtcaac ctacgcccat tttcaaccca     420
caggactcgt cttccttctc tacccttcct tgcgagagcc agtattgcca agatcttccg     480
agcgaaacct gcaataataa tgaatgccaa tatacatacg gatacggaga cggttccaca     540
acccaaggtt atatggcaac cgagaccttc actttcgaga cgagctccgt gccgaatatc     600
gcgttcggtt gcggggaaga caaccaggga ttcgggcaag caacggggc tggcctgatc      660 gggatgggtt ggggcccgtt atcgcttcct tctcaactcg gcgtgggtca gttctcttac     720
tgcatgacct cctatggaag ctcctcaccc agcactctcg cacttggatc cgcagccagt     780
ggagtgcctg aaggctcccc gagtacgacc ctcatccata gttctttgaa tccaacgtac     840
tattatatta cgctccaagg tataacggtt ggtggcgata tttgggtat ccatcgagt      900 acttttcaac ttcaagacga tggaactggc gggatgataa ttgactccgg acaacgctc      960 acttatcttc cacaagacgc ttacaatgcg gtagcacaag cgttcactga ccagataaat    1020
ctccccaccg tcgatgaatc ctcgagcggc tcagtacgt gcttccagca accgtccgac     1080
ggatcaaccg tgcaagttcc ggagattca atgcagtttg atggtggggt gctgaactta    1140
ggggaacaga atatattgat ctctccagct gaaggggtga tatgcttggc gatgggaagt    1200
tcatcgcagc tgggaatttc cattttggg aatatccagc agcaagaaac gcaggtgctc    1260
tatgaccttc agaatttggc cgtgtcgttc gttcctactc agtgtggtgc gtcgtag      1317
```

```
<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Gly Gln Gln Gln Pro Phe Pro Pro Gln Gln Pro Tyr Pro Gln Pro
1               5                   10                  15

Gln Pro Phe

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Gln Gln Gln Pro Pro Phe Ser Gln Gln Gln Ser Pro Phe Ser
1               5                   10                  15

Gln Gln Gln Gln
            20

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Tyr Tyr Pro Thr Ser Pro Gln Gln
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Gly Gln Gly Gln Gln
```

<210> SEQ ID NO 20
<211> LENGTH: 359
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Gln Ser Ser Ser Gly Ile Glu Thr Pro Val Tyr Ala Gly Asp Gly Glu
1               5                   10                  15

Tyr Leu Met Asn Val Ala Ile Gly Thr Pro Asp Ser Ser Phe Ser Ala
            20                  25                  30

Ile Met Asp Thr Gly Ser Asp Leu Ile Trp Thr Gln Cys Glu Pro Cys
        35                  40                  45

Thr Gln Cys Phe Ser Gln Pro Thr Pro Ile Phe Asn Pro Gln Asp Ser
    50                  55                  60

Ser Ser Phe Ser Thr Leu Pro Cys Glu Ser Gln Tyr Cys Gln Asp Leu
65                  70                  75                  80

Pro Ser Glu Thr Cys Asn Asn Glu Cys Gln Tyr Thr Tyr Gly Tyr
            85                  90                  95

Gly Asp Gly Ser Thr Thr Gln Gly Tyr Met Ala Thr Glu Thr Phe Thr
            100                 105                 110

Phe Glu Thr Ser Ser Val Pro Asn Ile Ala Phe Gly Cys Gly Glu Asp
        115                 120                 125

Asn Gln Gly Phe Gly Gln Gly Asn Gly Ala Gly Leu Ile Gly Met Gly
    130                 135                 140

Trp Gly Pro Leu Ser Leu Pro Ser Gln Leu Gly Val Gly Gln Phe Ser
145                 150                 155                 160

Tyr Cys Met Thr Ser Tyr Gly Ser Ser Pro Ser Thr Leu Ala Leu
            165                 170                 175

Gly Ser Ala Ala Ser Gly Val Pro Glu Gly Ser Pro Ser Thr Thr Leu
            180                 185                 190

Ile His Ser Ser Leu Asn Pro Thr Tyr Tyr Ile Thr Leu Gln Gly
        195                 200                 205

Ile Thr Val Gly Gly Asp Asn Leu Gly Ile Pro Ser Ser Thr Phe Gln
    210                 215                 220

Leu Gln Asp Asp Gly Thr Gly Gly Met Ile Ile Asp Ser Gly Thr Thr
225                 230                 235                 240

Leu Thr Tyr Leu Pro Gln Asp Ala Tyr Asn Ala Val Ala Gln Ala Phe
            245                 250                 255

Thr Asp Gln Ile Asn Leu Pro Thr Val Asp Glu Ser Ser Ser Gly Leu
            260                 265                 270

Ser Thr Cys Phe Gln Gln Pro Ser Asp Gly Ser Thr Val Gln Val Pro
        275                 280                 285

Glu Ile Ser Met Gln Phe Asp Gly Gly Val Leu Asn Leu Gly Glu Gln
    290                 295                 300

Asn Ile Leu Ile Ser Pro Ala Glu Gly Val Ile Cys Leu Ala Met Gly
305                 310                 315                 320

Ser Ser Ser Gln Leu Gly Ile Ser Ile Phe Gly Asn Ile Gln Gln
            325                 330                 335

Glu Thr Gln Val Leu Tyr Asp Leu Gln Asn Leu Ala Val Ser Phe Val
            340                 345                 350
```

```
Pro Thr Gln Cys Gly Ala Ser
        355

<210> SEQ ID NO 21
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asn Gly Pro Ser Gly Val Glu Thr Ser Val Tyr Ala Gly Asp Gly Glu
1               5                   10                  15

Tyr Leu Met Asn Leu Ser Ile Gly Thr Pro Ala Gln Pro Phe Ser Ala
            20                  25                  30

Ile Met Asp Thr Gly Ser Asp Leu Ile Trp Thr Gln Cys Gln Pro Cys
        35                  40                  45

Thr Gln Cys Phe Asn Gln Ser Thr Pro Ile Phe Asn Pro Gln Gly Ser
    50                  55                  60

Ser Ser Phe Ser Thr Leu Pro Cys Ser Ser Gln Leu Cys Gln Ala Leu
65                  70                  75                  80

Ser Ser Pro Thr Cys Ser Asn Asn Phe Cys Gln Tyr Thr Tyr Gly Tyr
                85                  90                  95

Gly Asp Gly Ser Glu Thr Gln Gly Ser Met Gly Thr Glu Thr Leu Thr
            100                 105                 110

Phe Gly Ser Val Ser Ile Pro Asn Ile Thr Phe Gly Cys Gly Glu Asn
        115                 120                 125

Asn Gln Gly Phe Gly Gln Gly Asn Gly Ala Gly Leu Val Gly Met Gly
    130                 135                 140

Arg Gly Pro Leu Ser Leu Pro Ser Gln Leu Asp Val Thr Lys Phe Ser
145                 150                 155                 160

Tyr Cys Met Thr Pro Ile Gly Ser Ser Thr Pro Ser Asn Leu Leu Leu
                165                 170                 175

Gly Ser Leu Ala Asn Ser Val Thr Ala Gly Ser Pro Asn Thr Thr Leu
            180                 185                 190

Ile Gln Ser Ser Gln Ile Pro Thr Phe Tyr Tyr Ile Thr Leu Asn Gly
        195                 200                 205

Leu Ser Val Gly Ser Thr Arg Leu Pro Ile Asp Pro Ser Ala Phe Ala
    210                 215                 220

Leu Asn Ser Asn Asn Gly Thr Gly Ile Ile Ile Asp Ser Gly Thr
225                 230                 235                 240

Thr Leu Thr Tyr Phe Val Asn Asn Ala Tyr Gln Ser Val Arg Gln Glu
                245                 250                 255

Phe Ile Ser Gln Ile Asn Leu Pro Val Val Asn Gly Ser Ser Ser Gly
            260                 265                 270

Phe Asp Leu Cys Phe Gln Thr Pro Ser Asp Pro Ser Asn Leu Gln Ile
        275                 280                 285

Pro Thr Phe Val Met His Phe Asp Gly Gly Asp Leu Glu Leu Pro Ser
    290                 295                 300

Glu Asn Tyr Phe Ile Ser Pro Ser Asn Gly Leu Ile Cys Leu Ala Met
305                 310                 315                 320

Gly Ser Ser Ser Gln Gly Met Ser Ile Phe Gly Asn Ile Gln Gln Gln
                325                 330                 335

Asn Met Leu Val Val Tyr Asp Thr Gly Asn Ser Val Val Ser Phe Ala
            340                 345                 350
```

Ser Ala Gln Cys Gly Ala Ser
        355

<210> SEQ ID NO 22
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gattacgcca agcttcattc ccgttgggat ctacgcattg                              40

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acgacaactc agatgggaag cgg                                                23

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Pro Leu Ser Leu Pro Ser Gln Leu Asp Val Thr Lys
1               5                   10

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Ser Tyr Val Arg
1               5

<210> SEQ ID NO 27

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Leu Gln Leu Gln Pro Phe Pro Gln Pro
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Gln Leu Gln Pro Phe Pro Gln Pro
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gln Pro Tyr Pro Gln Gln Pro
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Ala Asn Thr Asn His Gln Tyr Ala
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Ala Asn Thr Asn His Gln Tyr Ala Val
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32
```

```
Ser Ala Asn Thr Asn His Gln Tyr Ala Val Ile
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Ala Asn Thr Asn His Gln Tyr Ala Val Ile Ala
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Ala Asn Thr Asn His Gln Tyr Ala Val Ile Ala Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ile Trp Glu Pro Asn Leu Lys Asn Pro Asn Gly Asp
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Trp Glu Pro Asn Leu Lys Asn Pro Asn Gly Asp Phe
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ile Trp Glu Pro Asn Leu Lys Asn Pro Asn Gly Asp Phe Ser Leu
1               5                   10                  15

<210> SEQ ID NO 38
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 38

Asn Leu Lys Asn Pro Asn Gly Asp Phe
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Trp Ile Ser Ala Gly Ser Gly Ser Ser Leu
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Trp Ile Ser Ala Gly Ser Gly Ser Ser Leu
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Trp Ile Ser Ala Gly Ser Gly Ser Ser Leu Asn Thr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Ser Ala Gly Ser Gly Ser Ser Leu Asn Thr
1               5                   10

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Glu Ala Gly Trp Gln Val Tyr Pro Gly Arg Thr Gly Asp Ser Gln
1               5                   10                  15

Pro Arg Phe
```

```
<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Gly Trp Gln Val Tyr Pro Gly Arg Thr Gly Asp Ser Gln Pro Arg
1               5                   10                  15
Phe

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Gln Val Tyr Pro Gly Arg Thr Gly Asp Ser Gln Pro Arg Phe
1               5                   10                  15

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Val Tyr Pro Gly Arg Thr Gly Asp Ser Gln Pro
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Val Tyr Pro Gly Arg Thr Gly Asp Ser Gln Pro Arg Phe
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Arg Thr Gly Asp Ser Gln Pro Arg Phe
1               5                   10

<210> SEQ ID NO 49
<211> LENGTH: 9
<212> TYPE: PRT
<213> ORGANISM: Artificial Sequence
<220> FEATURE:
```

<223> OTHER INFORMATION: Description of Artificial Sequence: Synthetic
       peptide

<400> SEQUENCE: 49

Phe Ile Tyr Trp Thr Ala Asp Gly Tyr
1               5

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 50

Phe Ile Tyr Trp Thr Ala Asp Gly Tyr Thr Ser Thr Gly Cys
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 51

Pro Gly Phe Val Gln Thr Asn Asn Tyr
1               5

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 52

Met Ala Leu Gln Pro Ser Val Tyr Gly Gly Gln Gln
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 53

Ala Leu Gln Pro Ser Val Tyr Gly Gly Gln Gln
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 54

Leu Gln Pro Ser Val Tyr Gly Gly Gln Gln
1               5                   10

```
<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn Glu Ser Ile Gln Arg Asp Pro Ala Thr Gly Asn Trp
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Ile Gln Arg Asp Pro Ala Thr Gly Asn Trp
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Ile Gln Arg Asp Pro Ala Thr Gly Asn Trp Trp
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Ile Gln Arg Asp Pro Ala Thr Gly Asn Trp Trp Leu
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ile Gln Arg Asp Pro Ala Thr Gly Asn Trp
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60
```

```
Ile Gln Arg Asp Pro Ala Thr Gly Asn Trp Trp
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Trp Gly Thr Val Val Gly Tyr Trp Pro Ala
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Gly Thr Val Val Gly Tyr Trp Pro Ala Ser
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Trp Gly Thr Val Val Gly Tyr Trp Pro Ala Ser Ile
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Thr Val Val Gly Tyr Trp Pro Ala Ser Ile
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Ile Tyr Asn Ser Ile Thr Asn Gly Ala Asp
1               5                   10

<210> SEQ ID NO 66
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 66

Ile Tyr Asn Ser Ile Thr Asn Gly Ala Asp
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Tyr Asn Ser Ile Thr Asn Gly Ala Asp
1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Thr Val Glu Trp Gly Gly Glu Ile Tyr Asp
1               5                   10

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Val Glu Trp Gly Gly Glu Ile Tyr Asp Ser Ser Gly Thr Gly Gly
1               5                   10                  15

Phe

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Trp Gly Gly Glu Ile Tyr Asp Ser Ser Gly Thr Gly Gly Phe
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Tyr Asp Ser Ser Gly Thr Gly Gly Phe
```

```
<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Tyr Asp Ser Ser Gly Thr Gly Gly Phe His Thr Thr Thr Gln
1               5                   10                  15

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Val Arg Asp Leu Gln
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Val Arg Asp Leu Gln Cys
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Val Arg Asp Leu Gln Cys Val Asp
1               5

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Val Asp Thr Tyr Gly Asn Val Ile Ser Pro
1               5                   10

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 77

Val Asp Thr Tyr Gly Asn Val Ile Ser Pro Thr Ala Asn Ser Phe
1               5                   10                  15

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Ala Asn Ser Phe Gln Gly Ile Ala Pro Ala Pro
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Ala Asn Ser Phe Gln Gly Ile Ala Pro Ala Pro Asn Cys
1               5                   10

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Ala Asn Ser Phe Gln Gly Ile Ala Pro Ala Pro Asn Cys Tyr
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Ala Asn Ser Phe Gln Gly Ile Ala Pro Ala Pro Asn Cys Tyr Asn
1               5                   10                  15

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Ala Asn Ser Phe Gln Gly Ile Ala Pro Ala Pro Asn Cys Tyr Asn
1               5                   10                  15

Tyr

```
<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Gly Ile Ala Pro Ala Pro Asn Cys
1               5

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Gly Ile Ala Pro Ala Pro Asn Cys Tyr
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Gly Ile Ala Pro Ala Pro Asn Cys Tyr Asn
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asn Tyr Gln Phe Gln Gln Gly Ser Ser Glu
1               5                   10

<210> SEQ ID NO 87
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Ser Gly Gly Phe Glu Leu Gln Pro Arg Asp Gly Gly Pro Arg Val
1               5                   10                  15

Ala Leu Ala Pro Gly Glu Thr Val Ile Gly Arg Gly Pro Leu Leu Gly
            20                  25                  30

Ile Thr Asp Lys Arg Val Ser Arg Arg His Ala Ile Leu Glu Val Ala
        35                  40                  45

Gly Gly Gln Leu Arg Ile Lys Pro Ile His Thr Asn Pro Cys Phe Tyr
    50                  55                  60
```

```
Gln Ser Ser Glu Lys Ser Gln Leu Leu Pro Leu Lys Pro Asn Leu Trp
 65                  70                  75                  80

Cys Tyr Leu Asn Pro Gly Asp Ser Phe Ser Leu Leu Val Asp Lys Tyr
                 85                  90                  95

Ile Phe Arg Ile Leu Ser Ile Pro Ser Glu Val Glu Met Gln Cys Thr
            100                 105                 110

Leu Arg Asn Ser Gln Val Leu Asp Glu Asp Asn Ile Leu Asn Glu Thr
            115                 120                 125

Pro Lys Ser Pro Val Ile Asn Leu Pro His Glu Thr Thr Gly Ala Ser
            130                 135                 140

Gln Leu Glu Gly Ser Thr Glu Ile Ala Lys Thr Gln Met Thr Pro Thr
145                 150                 155                 160

Asn Ser Val Ser Phe Leu Gly Glu Asn Arg Asp Cys Asn Lys Gln Gln
                165                 170                 175

Pro Ile Leu Ala Glu Arg Lys Arg Ile Leu Pro Thr Trp Met Leu Ala
            180                 185                 190

Glu His Leu Ser Asp Gln Asn Leu Ser Val Pro Ala Ile Ser Gly Gly
            195                 200                 205

Asn Val Ile Gln Gly Ser Gly Lys Glu Ile Cys Lys Asp Lys Ser
210                 215                 220

Gln Leu Asn Thr Thr Gln Gln Gly Arg Arg Gln Leu Ile Ser Ser Gly
225                 230                 235                 240

Ser Ser Glu Asn Thr Ser Ala Glu Gln Asp Thr Gly Glu Glu Cys Lys
                245                 250                 255

Asn Thr Asp Gln Glu Glu Ser Thr Ile Ser Ser Lys Glu Met Pro Gln
            260                 265                 270

Ser Phe Ser Ala Ile Thr Leu Ser Asn Thr Glu Met Asn Asn Ile Lys
            275                 280                 285

Thr Asn Ala Gln Arg Asn Lys Leu Pro Ile Glu Glu Leu Gly Lys Val
            290                 295                 300

Ser Lys His Lys Ile Ala Thr Lys Arg Thr Pro His Lys Glu Asp Glu
305                 310                 315                 320

Ala Met Ser Cys Ser Glu Asn Cys Ser Ser Ala Gln Gly Asp Ser Leu
                325                 330                 335

Gln Asp Glu Ser Gln Gly Ser His Ser Glu Ser Ser Ser Asn Pro Ser
            340                 345                 350

Asn Pro Glu Thr Leu His Ala Lys Ala Thr Asp Ser Val Leu Gln Gly
            355                 360                 365

Ser Glu Gly Asn Lys Val Lys Arg Thr Ser Cys Met Tyr Gly Ala Asn
370                 375                 380

Cys Tyr Arg Lys Asn Pro Val His Phe Gln His Phe Ser His Pro Gly
385                 390                 395                 400

Asp Ser Asp Tyr Gly Gly Val Gln Ile Val Gly Gln Asp Glu Thr Asp
                405                 410                 415

Asp Arg Pro Glu Cys Pro Tyr Gly Pro Ser Cys Tyr Arg Lys Asn Pro
            420                 425                 430

Gln His Lys Ile Glu Tyr Arg His Asn Thr Leu Pro Val Arg Asn Val
            435                 440                 445

Leu Asp Glu Asp Asn Asp Asn Val Gly Gln Pro Asn Glu Tyr Asp Leu
            450                 455                 460

Asn Asp Ser Phe Leu Asp Asp Glu Glu Asp Tyr Glu Pro Thr Asp
465                 470                 475                 480

Glu Asp Ser Asp Trp Glu Pro Gly Lys Glu Asp Glu Glu Lys Glu Asp
```

```
                    485                 490                 495
Val Glu Glu Leu Leu Lys Glu Ala Lys Arg Phe Met Lys Arg Lys
            500                 505                 510
```

<210> SEQ ID NO 88
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln
            20                  25                  30
```

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

```
Gln Leu Pro Tyr Pro Gln Pro Gln Pro Phe
1               5                   10
```

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Phe Pro Gln Pro Gln Leu Pro Tyr Pro Gln
1               5                   10
```

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Gln Leu Pro Tyr Pro Gln Pro
1               5
```

<210> SEQ ID NO 92
<211> LENGTH: 307
<212> TYPE: PRT
<213> ORGANISM: Triticum aestivum

<400> SEQUENCE: 92

```
Met Lys Thr Phe Leu Ile Leu Ala Leu Leu Ala Ile Val Ala Thr Thr
1               5                   10                  15

Ala Arg Ile Ala Val Arg Val Pro Val Pro Gln Leu Gln Pro Gln Asn
            20                  25                  30

Pro Ser Gln Gln Gln Pro Gln Glu Gln Val Pro Leu Val Gln Gln Gln
```

```
                35                  40                  45
Gln Phe Pro Gly Gln Gln Pro Phe Pro Pro Gln Gln Pro Tyr Pro
                50                  55                  60

Gln Pro Gln Pro Phe Pro Ser Gln Gln Pro Tyr Leu Gln Leu Gln Pro
65                  70                  75                  80

Phe Pro Gln Pro Gln Leu Pro Tyr Pro Gln Pro Gln Leu Pro Tyr Pro
                85                  90                  95

Gln Pro Gln Leu Pro Tyr Pro Gln Pro Gln Pro Phe Arg Pro Gln Gln
                100                 105                 110

Pro Tyr Pro Gln Ser Gln Pro Gln Tyr Ser Gln Pro Gln Gln Pro Ile
            115                 120                 125

Ser Gln Gln Gln Gln Gln Gln Gln Gln Gln Gln Gln Lys Gln Gln
130                 135                 140

Gln Gln Gln Gln Gln Gln Ile Leu Gln Gln Ile Leu Gln Gln Leu
145                 150                 155                 160

Ile Pro Cys Arg Asp Val Val Leu Gln Gln His Ser Ile Ala Tyr Gly
                165                 170                 175

Ser Ser Gln Val Leu Gln Gln Ser Thr Tyr Gln Leu Val Gln Gln Leu
                180                 185                 190

Cys Cys Gln Gln Leu Trp Gln Ile Pro Glu Gln Ser Arg Cys Gln Ala
            195                 200                 205

Ile His Asn Val Val His Ala Ile Ile Leu His Gln Gln Gln Gln
            210                 215                 220

Gln Gln Gln Gln Gln Gln Pro Leu Ser Gln Val Ser Phe Gln Gln
225                 230                 235                 240

Pro Gln Gln Gln Tyr Pro Ser Gly Gln Gly Ser Phe Gln Pro Ser Gln
                245                 250                 255

Gln Asn Pro Gln Ala Gln Gly Ser Val Gln Pro Gln Gln Leu Pro Gln
                260                 265                 270

Phe Glu Glu Ile Arg Asn Leu Ala Leu Glu Thr Leu Pro Ala Met Cys
            275                 280                 285

Asn Val Tyr Ile Pro Pro Tyr Cys Thr Ile Ala Pro Val Gly Ile Phe
            290                 295                 300

Gly Thr Asn
305

<210> SEQ ID NO 93
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Tyr Leu Gln Leu Gln Pro Phe Pro Gln Pro Gln Leu Pro Tyr Pro Gln
1               5                   10                  15

Pro Gln Leu Pro Tyr Pro Gln Pro Gln Leu Pro Tyr Pro Gln Pro Gln
            20                  25                  30

Pro Phe

<210> SEQ ID NO 94
<211> LENGTH: 26
<212> TYPE: PRT
<213> ORGANISM: Artificial Sequence
<220> FEATURE:
<223> OTHER INFORMATION: Description of Artificial Sequence: Synthetic
```

```
      peptide

<400> SEQUENCE: 94

Phe Leu Gln Pro Gln Gln Pro Phe Pro Gln Gln Pro Gln Gln Pro Tyr
1               5                   10                  15

Pro Gln Gln Pro Gln Gln Pro Phe Pro Gln
            20                  25
```